(12) United States Patent
Noe et al.

(10) Patent No.: US 10,470,881 B2
(45) Date of Patent: Nov. 12, 2019

(54) REPLACEMENT MITRAL VALVES

(71) Applicant: Cephea Valve Technologies, Inc., San Jose, CA (US)

(72) Inventors: Spencer Noe, Santa Cruz, CA (US); Dan Wallace, Santa Cruz, CA (US); Jonathan Oakden, Santa Cruz, CA (US)

(73) Assignee: Cephea Valve Technologies, Inc., San Jose, CA (US)

( * ) Notice: Subject to any disclaimer, the term of this patent is extended or adjusted under 35 U.S.C. 154(b) by 0 days.

(21) Appl. No.: 15/908,701

(22) Filed: Feb. 28, 2018

(65) Prior Publication Data
US 2018/0206983 A1 Jul. 26, 2018
US 2019/0083241 A9 Mar. 21, 2019

Related U.S. Application Data

(63) Continuation of application No. PCT/US2018/014902, filed on Jan. 23, 2018, and a
(Continued)

(51) Int. Cl.
*A61F 2/24* (2006.01)
*A61F 2/82* (2013.01)

(52) U.S. Cl.
CPC .......... *A61F 2/2418* (2013.01); *A61F 2/2409* (2013.01); *A61F 2/2412* (2013.01);
(Continued)

(58) Field of Classification Search
CPC .... A61F 2/07; A61F 2/848; A61F 2/89; A61F 2/2418; A61F 2/2445; A61F 2220/0016; A61F 2002/075; A61F 2230/001
See application file for complete search history.

(56) References Cited

U.S. PATENT DOCUMENTS 3,334,629 A 8/1967 Cohn
3,409,013 A 11/1968 Henry
(Continued)

FOREIGN PATENT DOCUMENTS

CA 2859666 A1 6/2013
CN 1338951 A 3/2002
(Continued)

OTHER PUBLICATIONS

Andersen et al.; Transluminal implantation of artificial heart valves. Description of a new expandable aortic valve and initial results with implantation by catheter technique in closed chest pigs; Euro. Heart J.; 13 (5): 704-708; May 1992.
(Continued)

*Primary Examiner* — Christopher D. Prone
*Assistant Examiner* — Tiffany P Shipmon
(74) *Attorney, Agent, or Firm* — Lerner, David, Littenberg, Krumholz & Mentlik, LLP

(57) ABSTRACT

A prosthetic mitral valve includes an anchor assembly, a strut frame, and a plurality of replacement leaflets secured to the annular strut frame. The anchor assembly includes a ventricular anchor, an atrial anchor, and a central portion therebetween. The ventricular anchor and the atrial anchor are configured to flare radially outwards relative to the central portion. The annular strut frame is disposed radially within the anchor assembly and is attached to the anchor assembly. The central portion is configured to align with a native valve orifice and the ventricular anchor and the atrial anchor are configured to compress native cardiac tissue therebetween.

28 Claims, 76 Drawing Sheets

Related U.S. Application Data continuation-in-part of application No. 15/688,673, filed on Aug. 28, 2017, which is a continuation of application No. 15/669,805, filed on Aug. 4, 2017, now Pat. No. 10,143,552, which is a continuation of application No. PCT/US2016/032550, filed on May 13, 2016.

(60) Provisional application No. 62/513,877, filed on Jun. 1, 2017, provisional application No. 62/449,498, filed on Jan. 23, 2017, provisional application No. 62/259,565, filed on Nov. 24, 2015, provisional application No. 62/161,743, filed on May 14, 2015.

(52) U.S. Cl.
CPC .......... *A61F 2/2445* (2013.01); *A61F 2/2427* (2013.01); *A61F 2002/825* (2013.01); *A61F 2220/0008* (2013.01); *A61F 2220/0016* (2013.01); *A61F 2220/0041* (2013.01); *A61F 2230/001* (2013.01); *A61F 2230/0006* (2013.01); *A61F 2230/0054* (2013.01); *A61F 2230/0065* (2013.01); *A61F 2250/006* (2013.01); *A61F 2250/0018* (2013.01); *A61F 2250/0069* (2013.01)

(56) References Cited

U.S. PATENT DOCUMENTS

| | | |
|---|---|---|
| 3,540,431 A | 11/1970 | Mobin-Uddin |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,056,854 A | 11/1977 | Boretos et al. |
| 4,106,129 A | 8/1978 | Carpentier et al. |
| 4,233,690 A | 11/1980 | Akins |
| 4,291,420 A | 9/1981 | Reul |
| 4,326,306 A | 4/1982 | Poler |
| 4,423,809 A | 1/1984 | Mazzocco |
| 4,425,908 A | 1/1984 | Simon |
| 4,501,030 A | 2/1985 | Lane |
| 4,531,943 A | 7/1985 | Van Tassel et al. |
| 4,580,568 A | 4/1986 | Gianturco |
| 4,602,911 A | 7/1986 | Ahmadi et al. |
| 4,610,688 A | 9/1986 | Silvestrini et al. |
| 4,617,932 A | 10/1986 | Kornberg |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,710,192 A | 12/1987 | Liotta et al. |
| 4,733,665 A | 3/1988 | Palmaz |
| 4,755,181 A | 7/1988 | Igoe |
| 4,796,629 A | 1/1989 | Grayzel |
| 4,819,751 A | 4/1989 | Shimada et al. |
| 4,834,755 A | 5/1989 | Silvestrini et al. |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,909,252 A | 3/1990 | Goldberger |
| 4,917,102 A | 4/1990 | Miller et al. |
| 4,927,426 A | 5/1990 | Dretler |
| 4,986,830 A | 1/1991 | Owens et al. |
| 4,994,077 A | 2/1991 | Dobben |
| 5,002,556 A | 3/1991 | Ishida et al. |
| 5,002,559 A | 3/1991 | Tower |
| 5,064,435 A | 11/1991 | Porter |
| 5,161,547 A | 11/1992 | Tower |
| 5,163,953 A | 11/1992 | Vince |
| 5,209,741 A | 5/1993 | Spaeth |
| 5,258,023 A | 11/1993 | Reger |
| 5,258,042 A | 11/1993 | Mehta |
| 5,332,402 A | 7/1994 | Teitelbaum |
| 5,336,258 A | 8/1994 | Quintero et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,405,377 A * | 4/1995 | Cragg ........................ A61F 2/88 606/191 |
| 5,411,552 A | 5/1995 | Andersen et al. |
| 5,425,762 A | 6/1995 | Muller |
| 5,431,676 A | 7/1995 | Dubrul et al. |
| 5,443,495 A | 8/1995 | Buscemi et al. |
| 5,443,499 A | 8/1995 | Schmitt |
| 5,476,506 A | 12/1995 | Lunn |
| 5,476,510 A | 12/1995 | Eberhardt et al. |
| 5,480,423 A | 1/1996 | Ravenscroft et al. |
| 5,507,767 A | 4/1996 | Maeda et al. |
| 5,534,007 A | 7/1996 | St. Germain et al. |
| 5,545,133 A | 8/1996 | Burns et al. |
| 5,545,211 A | 8/1996 | An et al. |
| 5,549,665 A | 8/1996 | Vesely et al. |
| 5,554,183 A | 9/1996 | Nazari |
| 5,554,185 A | 9/1996 | Block et al. |
| 5,571,215 A | 11/1996 | Sterman et al. |
| 5,573,520 A | 11/1996 | Schwartz et al. |
| 5,575,818 A | 11/1996 | Pinchuk |
| 5,645,559 A | 7/1997 | Hachtman et al. |
| 5,662,671 A | 9/1997 | Barbut et al. |
| 5,667,523 A | 9/1997 | Bynon et al. |
| 5,674,277 A | 10/1997 | Freitag |
| 5,693,083 A | 12/1997 | Baker et al. |
| 5,695,498 A | 12/1997 | Tower |
| 5,713,953 A | 2/1998 | Vallana et al. |
| 5,716,370 A | 2/1998 | Williamson et al. |
| 5,720,391 A | 2/1998 | Dohm et al. |
| 5,725,552 A | 3/1998 | Kotula et al. |
| 5,733,325 A | 3/1998 | Robinson et al. |
| 5,735,842 A | 4/1998 | Krueger et al. |
| 5,769,812 A | 6/1998 | Stevens et al. |
| 5,807,405 A | 9/1998 | Vanney et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,064 A | 10/1998 | Taheri |
| 5,843,158 A | 12/1998 | Lenker et al. |
| 5,855,597 A | 1/1999 | Jayaraman |
| 5,855,601 A | 1/1999 | Bessler et al. |
| 5,860,966 A | 1/1999 | Tower |
| 5,861,024 A | 1/1999 | Rashidi |
| 5,861,028 A | 1/1999 | Angell |
| 5,868,783 A | 2/1999 | Tower |
| 5,876,448 A | 3/1999 | Thompson et al. |
| 5,885,228 A | 3/1999 | Rosenman et al. |
| 5,888,201 A | 3/1999 | Stinson et al. |
| 5,891,191 A | 4/1999 | Stinson |
| 5,895,399 A | 4/1999 | Barbut et al. |
| 5,907,893 A | 6/1999 | Zadno-Azizi et al. |
| 5,911,734 A | 6/1999 | Tsugita et al. |
| 5,925,063 A | 7/1999 | Khosravi |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,957,973 A | 9/1999 | Quiachon et al. |
| 5,968,070 A | 10/1999 | Bley et al. |
| 5,984,957 A | 11/1999 | Laptewicz et al. |
| 5,984,959 A | 11/1999 | Robertson et al. |
| 5,984,973 A | 11/1999 | Girard et al. |
| 5,993,469 A | 11/1999 | McKenzie et al. |
| 5,997,557 A | 12/1999 | Barbut et al. |
| 6,010,522 A | 1/2000 | Barbut et al. |

(56) References Cited

U.S. PATENT DOCUMENTS

| | | |
|---|---|---|
| 6,022,370 A | 2/2000 | Tower |
| 6,027,525 A | 2/2000 | Suh et al. |
| 6,042,598 A | 3/2000 | Tsugita et al. |
| 6,042,607 A | 3/2000 | Williamson et al. |
| 6,093,203 A | 7/2000 | Uflacker |
| 6,113,612 A | 9/2000 | Swanson et al. |
| 6,123,723 A | 9/2000 | Konya et al. |
| 6,142,987 A | 11/2000 | Tsugita |
| 6,162,245 A | 12/2000 | Jayaraman |
| 6,165,209 A | 12/2000 | Patterson et al. |
| 6,168,579 B1 | 1/2001 | Tsugita |
| 6,171,327 B1 | 1/2001 | Daniel et al. |
| 6,174,322 B1 | 1/2001 | Schneidt |
| 6,179,859 B1 | 1/2001 | Bates et al. |
| 6,187,016 B1 | 2/2001 | Hedges et al. |
| 6,197,053 B1 | 3/2001 | Cosgrove et al. |
| 6,200,336 B1 | 3/2001 | Pavcnik et al. |
| 6,206,909 B1 | 3/2001 | Hanada et al. |
| 6,214,036 B1 | 4/2001 | Letendre et al. |
| 6,221,006 B1 | 4/2001 | Dubrul et al. |
| 6,221,096 B1 | 4/2001 | Aiba et al. |
| 6,231,544 B1 | 5/2001 | Tsugita et al. |
| 6,231,551 B1 | 5/2001 | Barbut |
| 6,241,757 B1 | 6/2001 | An et al. |
| 6,245,102 B1 | 6/2001 | Jayaraman |
| 6,251,135 B1 | 6/2001 | Stinson et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,309,417 B1 | 10/2001 | Spence et al. |
| 6,312,465 B1 | 11/2001 | Griffin et al. |
| 6,319,281 B1 | 11/2001 | Patel |
| 6,336,934 B1 | 1/2002 | Gilson et al. |
| 6,336,937 B1 | 1/2002 | Vonesh et al. |
| 6,338,735 B1 | 1/2002 | Stevens |
| 6,348,063 B1 | 2/2002 | Yassour et al. |
| 6,352,708 B1 | 3/2002 | Duran et al. |
| 6,361,545 B1 | 3/2002 | Macoviak et al. |
| 6,371,970 B1 | 4/2002 | Khosravi et al. |
| 6,371,983 B1 | 4/2002 | Lane |
| 6,379,368 B1 | 4/2002 | Corcoran et al. |
| 6,379,383 B1 | 4/2002 | Palmaz et al. |
| 6,398,807 B1 | 6/2002 | Chouinard et al. |
| 6,409,750 B1 | 6/2002 | Hyodoh et al. |
| 6,411,552 B1 | 6/2002 | Chiba |
| 6,416,510 B1 | 7/2002 | Altman et al. |
| 6,419,696 B1 | 7/2002 | Ortiz et al. |
| 6,425,916 B1 | 7/2002 | Garrison et al. |
| 6,440,152 B1 | 8/2002 | Gainor et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,468,303 B1 | 10/2002 | Amplatz et al. |
| 6,475,239 B1 | 11/2002 | Campbell et al. |
| 6,482,228 B1 | 11/2002 | Norred |
| 6,485,502 B2 | 11/2002 | Don Michael et al. |
| 6,494,909 B2 | 12/2002 | Greenhalgh |
| 6,503,272 B2 | 1/2003 | Duerig et al. |
| 6,527,800 B1 | 3/2003 | McGuckin et al. |
| 6,540,768 B1 | 4/2003 | Diaz et al. |
| 6,562,058 B2 | 5/2003 | Seguin et al. |
| 6,592,546 B1 | 7/2003 | Barbut et al. |
| 6,592,614 B2 | 7/2003 | Lenker et al. |
| 6,610,077 B1 | 8/2003 | Hancock et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,518 B2 | 9/2003 | Thompson et al. |
| 6,635,068 B1 | 10/2003 | Dubrul et al. |
| 6,635,079 B2 | 10/2003 | Unsworth et al. |
| 6,652,571 B1 | 11/2003 | White et al. |
| 6,656,206 B2 | 12/2003 | Corcoran et al. |
| 6,663,588 B2 | 12/2003 | DuBois et al. |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,698 B2 | 1/2004 | McGuckin et al. |
| 6,682,558 B2 | 1/2004 | Tu et al. |
| 6,682,559 B2 | 1/2004 | Myers et al. |
| 6,689,144 B2 | 2/2004 | Gerberding |
| 6,689,164 B1 | 2/2004 | Seguin |
| 6,692,512 B2 | 2/2004 | Jang |
| 6,695,864 B2 | 2/2004 | Macoviak et al. |
| 6,695,865 B2 | 2/2004 | Boyle et al. |
| 6,702,851 B1 | 3/2004 | Chinn et al. |
| 6,712,836 B1 | 3/2004 | Berg et al. |
| 6,712,842 B1 | 3/2004 | Gifford et al. |
| 6,712,843 B2 | 3/2004 | Elliott |
| 6,714,842 B1 | 3/2004 | Ito |
| 6,723,122 B2 | 4/2004 | Yang et al. |
| 6,730,118 B2 | 5/2004 | Spenser et al. |
| 6,730,377 B2 | 5/2004 | Wang |
| 6,733,525 B2 | 5/2004 | Yang et al. |
| 6,752,828 B2 | 6/2004 | Thornton |
| 6,758,855 B2 | 7/2004 | Fulton et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,773,454 B2 | 8/2004 | Wholey et al. |
| 6,776,791 B1 | 8/2004 | Stallings et al. |
| 6,790,218 B2 | 9/2004 | Jayaraman |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,814,746 B2 | 11/2004 | Thompson et al. |
| 6,821,297 B2 | 11/2004 | Snyders |
| 6,837,901 B2 | 1/2005 | Rabkin et al. |
| 6,843,802 B1 | 1/2005 | Villalobos et al. |
| 6,849,085 B2 | 2/2005 | Marton |
| 6,863,668 B2 | 3/2005 | Gillespie et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,220 B2 | 4/2005 | Edwin et al. |
| 6,887,266 B2 | 5/2005 | Williams et al. |
| 6,890,340 B2 | 5/2005 | Duane |
| 6,893,459 B1 | 5/2005 | Macoviak |
| 6,893,460 B2 | 5/2005 | Spenser et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,037 B2 | 6/2005 | Gainor et al. |
| 6,913,614 B2 | 7/2005 | Marino et al. |
| 6,921,397 B2 | 7/2005 | Corcoran et al. |
| 6,936,058 B2 | 8/2005 | Forde et al. |
| 6,936,067 B2 | 8/2005 | Buchanan |
| 6,945,997 B2 | 9/2005 | Huynh et al. |
| 6,951,571 B1 | 10/2005 | Srivastava |
| 6,953,332 B1 | 10/2005 | Kurk et al. |
| 6,960,220 B2 | 11/2005 | Marino et al. |
| 6,960,224 B2 | 11/2005 | Marino et al. |
| 6,974,464 B2 | 12/2005 | Quijano et al. |
| 6,974,476 B2 | 12/2005 | McGuckin et al. |
| 6,979,350 B2 | 12/2005 | Moll et al. |
| 6,984,242 B2 | 1/2006 | Campbell et al. |
| 7,011,681 B2 | 3/2006 | Vesely |
| 7,018,406 B2 | 3/2006 | Seguin et al. |
| 7,025,791 B2 | 4/2006 | Levine et al. |
| 7,037,331 B2 | 5/2006 | Mitelberg et al. |
| 7,077,861 B2 | 7/2006 | Spence |
| 7,087,072 B2 | 8/2006 | Marino et al. |
| 7,115,135 B2 | 10/2006 | Corcoran et al. |
| 7,122,020 B2 | 10/2006 | Mogul |
| 7,144,410 B2 | 12/2006 | Marino et al. |
| 7,166,097 B2 | 1/2007 | Barbut |
| 7,175,653 B2 | 2/2007 | Gaber |
| 7,175,654 B2 | 2/2007 | Bonsignore et al. |
| 7,189,258 B2 | 3/2007 | Johnson et al. |
| 7,191,018 B2 | 3/2007 | Gielen et al. |

(56) References Cited

U.S. PATENT DOCUMENTS

| | | |
|---|---|---|
| 7,192,435 B2 | 3/2007 | Corcoran et al. |
| 7,201,772 B2 | 4/2007 | Schwammenthal et al. |
| 7,235,093 B2 | 6/2007 | Gregorich |
| 7,261,732 B2 | 8/2007 | Justino |
| 7,320,704 B2 | 1/2008 | Lashinski et al. |
| 7,329,279 B2 | 2/2008 | Haug et al. |
| 7,374,560 B2 | 5/2008 | Ressemann et al. |
| 7,381,219 B2 | 6/2008 | Salahieh et al. |
| 7,402,171 B2 | 7/2008 | Osborne et al. |
| 7,413,563 B2 | 8/2008 | Corcoran et al. |
| 7,445,631 B2 | 11/2008 | Salahieh et al. |
| 7,455,689 B2 | 11/2008 | Johnson |
| 7,566,336 B2 | 7/2009 | Corcoran et al. |
| 7,582,104 B2 | 9/2009 | Corcoran et al. |
| 7,591,848 B2 | 9/2009 | Allen |
| 7,625,364 B2 | 12/2009 | Corcoran et al. |
| 7,632,298 B2 | 12/2009 | Hijlkema et al. |
| 7,658,748 B2 | 2/2010 | Marino et al. |
| 7,691,115 B2 | 4/2010 | Corcoran et al. |
| 7,712,606 B2 | 5/2010 | Salahieh et al. |
| 7,722,666 B2 | 5/2010 | LaFontaine |
| 7,748,389 B2 | 7/2010 | Salahieh et al. |
| 7,749,238 B2 | 7/2010 | Corcoran et al. |
| 7,780,725 B2 | 8/2010 | Haug et al. |
| 7,803,184 B2 | 9/2010 | McGuckin et al. |
| 7,803,186 B1 | 9/2010 | Li et al. |
| 7,824,442 B2 | 11/2010 | Salahieh et al. |
| 7,824,443 B2 | 11/2010 | Salahieh et al. |
| 7,896,915 B2 | 3/2011 | Guyenot et al. |
| 7,905,901 B2 | 3/2011 | Corcoran et al. |
| 7,927,351 B2 | 4/2011 | Corcoran et al. |
| 7,972,361 B2 | 7/2011 | Corcoran et al. |
| 8,043,368 B2 | 10/2011 | Crabtree |
| 8,057,540 B2 | 11/2011 | Letac et al. |
| 8,092,520 B2 | 1/2012 | Quadri |
| 8,167,935 B2 | 5/2012 | McGuckin et al. |
| 8,236,049 B2 | 8/2012 | Rowe et al. |
| 8,317,858 B2 * | 11/2012 | Straubinger .......... A61F 2/2418 623/1.15 |
| 8,366,741 B2 | 2/2013 | Chin et al. |
| 8,398,708 B2 | 3/2013 | Meiri et al. |
| 8,425,593 B2 | 4/2013 | Braido et al. |
| 8,444,689 B2 | 5/2013 | Zhang |
| 8,449,599 B2 | 5/2013 | Chau et al. |
| 8,551,132 B2 | 10/2013 | Eskridge et al. |
| 8,551,161 B2 | 10/2013 | Dolan |
| 8,562,672 B2 | 10/2013 | Bonhoeffer et al. |
| 8,568,475 B2 | 10/2013 | Nguyen et al. |
| 8,579,964 B2 | 11/2013 | Lane et al. |
| 8,579,966 B2 | 11/2013 | Seguin et al. |
| 8,623,074 B2 | 1/2014 | Ryan |
| 8,628,566 B2 | 1/2014 | Eberhardt et al. |
| 8,673,000 B2 | 3/2014 | Tabor et al. |
| 8,685,080 B2 | 4/2014 | White |
| 8,721,708 B2 | 5/2014 | Sèguin et al. |
| 8,728,155 B2 | 5/2014 | Montorfano et al. |
| 8,740,962 B2 | 6/2014 | Finch et al. |
| 8,795,356 B2 | 8/2014 | Quadri et al. |
| 8,801,779 B2 | 8/2014 | Seguin et al. |
| 8,845,722 B2 | 9/2014 | Gabbay |
| 8,852,272 B2 | 10/2014 | Gross et al. |
| 8,870,948 B1 | 10/2014 | Erzberger et al. |
| 8,894,702 B2 | 11/2014 | Quadri et al. |
| 8,911,455 B2 | 12/2014 | Quadri et al. |
| 8,956,404 B2 | 2/2015 | Börtlein et al. |
| 8,986,375 B2 | 3/2015 | Garde et al. |
| 8,998,976 B2 | 4/2015 | Gregg et al. |
| 9,011,527 B2 | 4/2015 | Li et al. |
| 9,017,399 B2 | 4/2015 | Gross et al. |
| 9,023,074 B2 | 5/2015 | Theobald et al. |
| 9,023,100 B2 | 5/2015 | Quadri et al. |
| 9,034,032 B2 | 5/2015 | McLean et al. |
| 9,039,757 B2 | 5/2015 | McLean et al. |
| 9,060,857 B2 | 6/2015 | Nguyen et al. |
| 9,101,467 B2 | 8/2015 | Eberhardt et al. |
| 9,125,740 B2 | 9/2015 | Morriss et al. |
| 9,132,009 B2 | 9/2015 | Hacohen et al. |
| 9,155,617 B2 | 10/2015 | Carpentier et al. |
| 9,168,130 B2 | 10/2015 | Straubinger et al. |
| 9,168,131 B2 | 10/2015 | Yohanan et al. |
| 9,232,994 B2 | 1/2016 | Miller |
| 9,387,071 B2 | 7/2016 | Tuval et al. |
| 9,393,110 B2 | 7/2016 | Levi et al. |
| 9,393,112 B2 | 7/2016 | Tuval et al. |
| 9,414,852 B2 | 8/2016 | Gifford et al. |
| 9,414,913 B2 | 8/2016 | Beith et al. |
| 9,421,083 B2 | 8/2016 | Eidenschink et al. |
| 9,421,098 B2 | 8/2016 | Gifford et al. |
| 9,439,757 B2 | 9/2016 | Granada et al. |
| 9,474,605 B2 | 10/2016 | Rowe et al. |
| 9,474,609 B2 | 10/2016 | Haverkost et al. |
| 9,480,556 B2 | 11/2016 | Revuelta et al. |
| 9,480,558 B2 | 11/2016 | Destefano |
| 9,480,563 B2 | 11/2016 | Li |
| 9,486,306 B2 | 11/2016 | Tegels et al. |
| 9,492,273 B2 | 11/2016 | Granada et al. |
| 9,498,330 B2 | 11/2016 | Solem |
| 9,504,564 B2 | 11/2016 | Nguyen et al. |
| 9,504,568 B2 | 11/2016 | Ryan et al. |
| 9,510,943 B2 | 12/2016 | Mesana et al. |
| 9,554,899 B2 | 1/2017 | Granada et al. |
| 9,561,103 B2 | 2/2017 | Granada et al. |
| 9,579,198 B2 | 2/2017 | Deem et al. |
| 9,655,722 B2 | 5/2017 | Morriss et al. |
| 9,883,941 B2 | 2/2018 | Hastings et al. |
| 9,949,824 B2 | 4/2018 | Bonhoeffer et al. |
| 10,004,601 B2 | 6/2018 | Tuval et al. |
| 10,143,552 B2 | 12/2018 | Wallace et al. |
| 2001/0007956 A1 | 7/2001 | Letac et al. |
| 2001/0039450 A1 | 11/2001 | Pavcnik et al. |
| 2001/0041928 A1 | 11/2001 | Pavcnik et al. |
| 2001/0041930 A1 | 11/2001 | Globerman et al. |
| 2001/0044652 A1 | 11/2001 | Moore |
| 2001/0044656 A1 | 11/2001 | Williamson et al. |
| 2002/0002396 A1 | 1/2002 | Fulkerson |
| 2002/0010489 A1 | 1/2002 | Grayzel et al. |
| 2002/0026233 A1 | 2/2002 | Shaknovich |
| 2002/0029981 A1 | 3/2002 | Nigam |
| 2002/0032481 A1 | 3/2002 | Gabbay |
| 2002/0055769 A1 | 5/2002 | Wang |
| 2002/0062135 A1 | 5/2002 | Mazzocchi et al. |
| 2002/0082609 A1 | 6/2002 | Green |
| 2002/0095173 A1 | 7/2002 | Mazzocchi et al. |
| 2002/0120328 A1 | 8/2002 | Pathak et al. |
| 2002/0161392 A1 | 10/2002 | Dubrul |
| 2002/0161394 A1 | 10/2002 | Macoviak et al. |
| 2002/0177766 A1 | 11/2002 | Mogul |
| 2002/0183781 A1 | 12/2002 | Casey et al. |
| 2002/0188341 A1 | 12/2002 | Elliott |
| 2002/0188344 A1 | 12/2002 | Bolea et al. |
| 2003/0023303 A1 | 1/2003 | Palmaz et al. |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0050694 A1 | 3/2003 | Yang et al. |
| 2003/0055495 A1 | 3/2003 | Pease et al. |
| 2003/0060844 A1 | 3/2003 | Borillo et al. |
| 2003/0070944 A1 | 4/2003 | Nigam |
| 2003/0074011 A1 | 4/2003 | Gilboa et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0130729 A1 | 7/2003 | Paniagua et al. |
| 2003/0135257 A1 | 7/2003 | Taheri |
| 2003/0144732 A1 | 7/2003 | Cosgrove et al. |
| 2003/0149476 A1 | 8/2003 | Damm et al. |
| 2003/0149477 A1 | 8/2003 | Gabbay |
| 2003/0149478 A1 | 8/2003 | Figulla et al. |
| 2003/0176884 A1 | 9/2003 | Berrada et al. |
| 2003/0181850 A1 | 9/2003 | Diamond et al. |
| 2003/0187495 A1 | 10/2003 | Cully et al. |
| 2003/0199971 A1 | 10/2003 | Tower et al. |

(56) References Cited

U.S. PATENT DOCUMENTS

| | | |
|---|---|---|
| 2003/0208224 A1 | 11/2003 | Broome |
| 2003/0212429 A1 | 11/2003 | Keegan et al. |
| 2003/0212454 A1 | 11/2003 | Scott et al. |
| 2003/0216774 A1 | 11/2003 | Larson |
| 2003/0225421 A1 | 12/2003 | Peavey et al. |
| 2003/0225445 A1 | 12/2003 | Derus et al. |
| 2003/0229390 A1 | 12/2003 | Ashton et al. |
| 2003/0233117 A1 | 12/2003 | Adams et al. |
| 2004/0034411 A1 | 2/2004 | Quijano et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0060563 A1 | 4/2004 | Rapacki et al. |
| 2004/0082904 A1 | 4/2004 | Houde et al. |
| 2004/0082967 A1 | 4/2004 | Broome et al. |
| 2004/0087982 A1 | 5/2004 | Eskuri |
| 2004/0093016 A1 | 5/2004 | Root et al. |
| 2004/0098022 A1 | 5/2004 | Barone |
| 2004/0098099 A1 | 5/2004 | McCullagh et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0127849 A1 | 7/2004 | Kantor |
| 2004/0127936 A1 | 7/2004 | Salahieh et al. |
| 2004/0127979 A1 | 7/2004 | Wilson et al. |
| 2004/0133232 A1 | 7/2004 | Rosenbluth et al. |
| 2004/0133274 A1 | 7/2004 | Webler et al. |
| 2004/0138694 A1 | 7/2004 | Tran et al. |
| 2004/0143294 A1 | 7/2004 | Corcoran et al. |
| 2004/0148021 A1 | 7/2004 | Cartledge et al. |
| 2004/0153094 A1 | 8/2004 | Dunfee et al. |
| 2004/0158277 A1 | 8/2004 | Lowe et al. |
| 2004/0167565 A1 | 8/2004 | Beulke et al. |
| 2004/0181140 A1 | 9/2004 | Falwell et al. |
| 2004/0186563 A1 | 9/2004 | Lobbi |
| 2004/0204755 A1 | 10/2004 | Robin |
| 2004/0215331 A1 | 10/2004 | Chew et al. |
| 2004/0215339 A1 | 10/2004 | Drasler et al. |
| 2004/0220655 A1 | 11/2004 | Swanson et al. |
| 2004/0225321 A1 | 11/2004 | Krolik et al. |
| 2004/0225354 A1 | 11/2004 | Allen et al. |
| 2004/0254636 A1 | 12/2004 | Flagle et al. |
| 2005/0033402 A1 | 2/2005 | Cully et al. |
| 2005/0038383 A1 | 2/2005 | Kelley et al. |
| 2005/0070934 A1 | 3/2005 | Tanaka et al. |
| 2005/0075662 A1 | 4/2005 | Pedersen et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0090846 A1 | 4/2005 | Pedersen et al. |
| 2005/0096692 A1 | 5/2005 | Linder et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0100580 A1 | 5/2005 | Osborne et al. |
| 2005/0107822 A1 | 5/2005 | WasDyke |
| 2005/0113910 A1 | 5/2005 | Paniagua et al. |
| 2005/0137686 A1 | 6/2005 | Salahieh et al. |
| 2005/0137687 A1* | 6/2005 | Salahieh ............ A61F 2/2418 623/2.11 |
| 2005/0137688 A1 | 6/2005 | Salahieh et al. |
| 2005/0137689 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137696 A1 | 6/2005 | Salahieh et al. |
| 2005/0137697 A1 | 6/2005 | Salahieh et al. |
| 2005/0137701 A1 | 6/2005 | Salahieh et al. |
| 2005/0143809 A1 | 6/2005 | Salahieh et al. |
| 2005/0165352 A1 | 7/2005 | Henry et al. |
| 2005/0182486 A1 | 8/2005 | Gabbay |
| 2005/0197694 A1 | 9/2005 | Pai et al. |
| 2005/0197695 A1 | 9/2005 | Stacchino et al. |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0209580 A1 | 9/2005 | Freyman |
| 2005/0228472 A1 | 10/2005 | Case et al. |
| 2005/0251250 A1 | 11/2005 | Verhoeven et al. |
| 2005/0251251 A1 | 11/2005 | Cribier |
| 2005/0261759 A1 | 11/2005 | Lambrecht et al. |
| 2005/0267560 A1 | 12/2005 | Bates |
| 2005/0283962 A1 | 12/2005 | Boudjemline |
| 2005/0288766 A1 | 12/2005 | Plain et al. |
| 2006/0004439 A1 | 1/2006 | Spenser et al. |
| 2006/0004442 A1 | 1/2006 | Spenser et al. |
| 2006/0015168 A1 | 1/2006 | Gunderson |
| 2006/0058872 A1 | 3/2006 | Salahieh et al. |
| 2006/0116717 A1 | 6/2006 | Marino et al. |
| 2006/0155312 A1 | 7/2006 | Levine et al. |
| 2006/0161249 A1 | 7/2006 | Realyvasquez et al. |
| 2006/0190030 A1 | 8/2006 | To et al. |
| 2006/0195183 A1 | 8/2006 | Navia et al. |
| 2006/0235510 A1 | 10/2006 | Johnson et al. |
| 2006/0247680 A1 | 11/2006 | Amplatz et al. |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259137 A1 | 11/2006 | Artof et al. |
| 2006/0265045 A1 | 11/2006 | Shiu et al. |
| 2006/0271166 A1 | 11/2006 | Thill et al. |
| 2006/0287668 A1 | 12/2006 | Fawzi et al. |
| 2007/0016286 A1 | 1/2007 | Herrmann et al. |
| 2007/0055340 A1 | 3/2007 | Pryor |
| 2007/0088431 A1 | 4/2007 | Bourang et al. |
| 2007/0100440 A1 | 5/2007 | Figulla et al. |
| 2007/0112355 A1 | 5/2007 | Salahieh et al. |
| 2007/0118214 A1 | 5/2007 | Salahieh et al. |
| 2007/0203503 A1 | 8/2007 | Salahieh et al. |
| 2007/0203575 A1 | 8/2007 | Forster et al. |
| 2007/0244552 A1 | 10/2007 | Salahieh et al. |
| 2007/0255389 A1 | 11/2007 | Oberti et al. |
| 2007/0265656 A1 | 11/2007 | Amplatz et al. |
| 2007/0276324 A1 | 11/2007 | Laduca et al. |
| 2007/0288089 A1 | 12/2007 | Gurskis et al. |
| 2008/0015619 A1 | 1/2008 | Figulla et al. |
| 2008/0033543 A1 | 2/2008 | Gurskis et al. |
| 2008/0082165 A1 | 4/2008 | Wilson et al. |
| 2008/0140189 A1 | 6/2008 | Nguyen et al. |
| 2008/0140191 A1 | 6/2008 | Mathis et al. |
| 2008/0167682 A1 | 7/2008 | Corcoran et al. |
| 2008/0177381 A1 | 7/2008 | Navia et al. |
| 2008/0188928 A1 | 8/2008 | Salahieh et al. |
| 2008/0208328 A1 | 8/2008 | Antocci et al. |
| 2008/0208332 A1 | 8/2008 | Lamphere et al. |
| 2008/0221672 A1 | 9/2008 | Lamphere et al. |
| 2008/0234797 A1 | 9/2008 | Styrc |
| 2008/0288054 A1 | 11/2008 | Pulnev et al. |
| 2009/0005863 A1 | 1/2009 | Goetz et al. |
| 2009/0036768 A1 | 2/2009 | Seehusen et al. |
| 2009/0062841 A1 | 3/2009 | Amplatz et al. |
| 2009/0082803 A1 | 3/2009 | Adams et al. |
| 2009/0171456 A1 | 7/2009 | Kveen et al. |
| 2009/0182405 A1 | 7/2009 | Arnault De La Menardiere et al. |
| 2009/0192585 A1 | 7/2009 | Bloom et al. |
| 2009/0222076 A1 | 9/2009 | Figulla et al. |
| 2009/0254165 A1 | 10/2009 | Tabor et al. |
| 2009/0264759 A1 | 10/2009 | Byrd |
| 2009/0287290 A1 | 11/2009 | Macaulay et al. |
| 2009/0306768 A1 | 12/2009 | Quadri |
| 2010/0036479 A1 | 2/2010 | Hill et al. |
| 2010/0049313 A1 | 2/2010 | Alon et al. |
| 2010/0094314 A1 | 4/2010 | Hernlund et al. |
| 2010/0114308 A1 | 5/2010 | Maschke |
| 2010/0121434 A1 | 5/2010 | Paul et al. |
| 2010/0161036 A1 | 6/2010 | Pintor et al. |
| 2010/0185277 A1 | 7/2010 | Braido et al. |
| 2010/0219092 A1 | 9/2010 | Salahieh et al. |
| 2010/0268204 A1 | 10/2010 | Tieu et al. |
| 2010/0280495 A1 | 11/2010 | Paul et al. |

(56) References Cited

U.S. PATENT DOCUMENTS

| | | |
|---|---|---|
| 2010/0284724 A1 | 11/2010 | Cardia |
| 2010/0298931 A1 | 11/2010 | Quadri et al. |
| 2010/0312333 A1 | 12/2010 | Navia et al. |
| 2011/0004296 A1 | 1/2011 | Lutter et al. |
| 2011/0022157 A1 | 1/2011 | Essinger et al. |
| 2011/0034987 A1 | 2/2011 | Kennedy |
| 2011/0166636 A1* | 7/2011 | Rowe .................... A61F 2/2418 623/1.11 |
| 2011/0218619 A1 | 9/2011 | Benichou et al. |
| 2011/0245911 A1 | 10/2011 | Quill et al. |
| 2011/0257723 A1 | 10/2011 | McNamara |
| 2011/0264198 A1 | 10/2011 | Murray et al. |
| 2011/0295363 A1 | 12/2011 | Girard et al. |
| 2011/0301702 A1 | 12/2011 | Rust et al. |
| 2012/0016464 A1 | 1/2012 | Seguin |
| 2012/0059458 A1 | 3/2012 | Buchbinder et al. |
| 2012/0078360 A1 | 3/2012 | Rafiee |
| 2012/0101572 A1 | 4/2012 | Kovalsky et al. |
| 2012/0158129 A1 | 6/2012 | Duffy et al. |
| 2012/0197283 A1 | 8/2012 | Marchand et al. |
| 2012/0197391 A1 | 8/2012 | Alkhatib et al. |
| 2013/0041447 A1 | 2/2013 | Erb et al. |
| 2013/0041458 A1 | 2/2013 | Lashinski et al. |
| 2013/0253643 A1 | 9/2013 | Rolando et al. |
| 2013/0261737 A1 | 10/2013 | Costello |
| 2013/0282110 A1 | 10/2013 | Schweich, Jr. et al. |
| 2013/0282114 A1 | 10/2013 | Schweich, Jr. et al. |
| 2013/0304197 A1 | 11/2013 | Buchbinder et al. |
| 2013/0310923 A1 | 11/2013 | Kheradvar et al. |
| 2013/0331931 A1 | 12/2013 | Gregg et al. |
| 2014/0005771 A1 | 1/2014 | Braido et al. |
| 2014/0005775 A1 | 1/2014 | Alkhatib et al. |
| 2014/0005778 A1 | 1/2014 | Buchbinder et al. |
| 2014/0012368 A1 | 1/2014 | Sugimoto et al. |
| 2014/0012374 A1 | 1/2014 | Rankin |
| 2014/0052237 A1 | 2/2014 | Lane et al. |
| 2014/0052241 A1 | 2/2014 | Harks et al. |
| 2014/0052244 A1 | 2/2014 | Rolando et al. |
| 2014/0067048 A1 | 3/2014 | Chau et al. |
| 2014/0081383 A1 | 3/2014 | Eberhardt et al. |
| 2014/0107665 A1 | 4/2014 | Shellenberger et al. |
| 2014/0128726 A1 | 5/2014 | Quill et al. |
| 2014/0180391 A1 | 6/2014 | Dagan et al. |
| 2014/0214157 A1 | 7/2014 | Bortlein et al. |
| 2014/0214159 A1 | 7/2014 | Vidlund et al. |
| 2014/0222136 A1 | 8/2014 | Geist et al. |
| 2014/0236278 A1 | 8/2014 | Argentine et al. |
| 2014/0243954 A1 | 8/2014 | Shannon |
| 2014/0249622 A1 | 9/2014 | Carmi et al. |
| 2014/0257476 A1 | 9/2014 | Montorfano et al. |
| 2014/0277390 A1* | 9/2014 | Ratz .................... A61F 2/2418 623/1.26 |
| 2014/0277563 A1 | 9/2014 | White |
| 2014/0324164 A1 | 10/2014 | Gross et al. |
| 2014/0330368 A1 | 11/2014 | Gloss et al. |
| 2014/0379076 A1 | 12/2014 | Vidlund et al. |
| 2015/0039083 A1 | 2/2015 | Rafiee |
| 2015/0045881 A1 | 2/2015 | Lim |
| 2015/0066141 A1 | 3/2015 | Braido et al. |
| 2015/0094802 A1 | 4/2015 | Buchbinder et al. |
| 2015/0112430 A1 | 4/2015 | Creaven et al. |
| 2015/0119637 A1 | 4/2015 | Alvarez et al. |
| 2015/0135506 A1 | 5/2015 | White |
| 2015/0142100 A1 | 5/2015 | Morriss et al. |
| 2015/0157457 A1 | 6/2015 | Hacohen |
| 2015/0173897 A1 | 6/2015 | Raanani et al. |
| 2015/0223773 A1 | 8/2015 | John et al. |
| 2015/0302634 A1 | 10/2015 | Florent et al. |
| 2015/0351903 A1 | 12/2015 | Morriss et al. |
| 2015/0351904 A1 | 12/2015 | Cooper et al. |
| 2016/0038280 A1 | 2/2016 | Morriss et al. |
| 2016/0089234 A1 | 3/2016 | Gifford |
| 2016/0151153 A1 | 6/2016 | Sandstrom et al. |
| 2016/0158000 A1 | 6/2016 | Granada et al. |
| 2016/0158003 A1 | 6/2016 | Wallace et al. |
| 2016/0166384 A1 | 6/2016 | Olson et al. |
| 2016/0310267 A1* | 10/2016 | Zeng .................... A61F 2/2418 |
| 2016/0310269 A1 | 10/2016 | Braido et al. |
| 2017/0035569 A1 | 2/2017 | Deem et al. |
| 2017/0042675 A1 | 2/2017 | Freudenthal |
| 2017/0049571 A1 | 2/2017 | Gifford |
| 2017/0209261 A1 | 7/2017 | Bortlein et al. |
| 2017/0209269 A1 | 7/2017 | Conklin |
| 2017/0231762 A1 | 8/2017 | Quadri et al. |
| 2017/0245991 A1 | 8/2017 | Granada et al. |
| 2017/0325941 A1 | 11/2017 | Wallace et al. |
| 2017/0325948 A1 | 11/2017 | Wallace et al. |
| 2017/0354499 A1 | 12/2017 | Granada et al. |
| 2018/0000580 A1 | 1/2018 | Wallace et al. |
| 2018/0056043 A1 | 3/2018 | von Oepen et al. |
| 2018/0092744 A1 | 4/2018 | von Oepen et al. |
| 2018/0110622 A1 | 4/2018 | Gregg et al. |
| 2018/0206983 A1 | 7/2018 | Noe et al. |
| 2018/0206984 A1 | 7/2018 | Noe et al. |
| 2018/0206985 A1 | 7/2018 | Noe et al. |
| 2018/0206986 A1 | 7/2018 | Noe et al. |
| 2018/0296325 A1 | 10/2018 | McLean |
| 2018/0296335 A1 | 10/2018 | Miyashiro |
| 2018/0296339 A1 | 10/2018 | McLean |
| 2018/0296341 A1 | 10/2018 | Noe et al. |

FOREIGN PATENT DOCUMENTS

| | | |
|---|---|---|
| EP | 0409929 B1 | 4/1997 |
| EP | 1057459 A1 | 12/2000 |
| EP | 1057460 A1 | 12/2000 |
| EP | 0937439 B1 | 9/2003 |
| EP | 1340473 A2 | 9/2003 |
| EP | 1356793 A2 | 10/2003 |
| EP | 1042045 B1 | 5/2004 |
| EP | 0819013 B1 | 6/2004 |
| EP | 1229864 B1 | 4/2005 |
| EP | 1430853 A2 | 6/2005 |
| EP | 1059894 B1 | 7/2005 |
| EP | 1078610 B1 | 8/2005 |
| EP | 1469797 B1 | 11/2005 |
| EP | 1600121 A1 | 11/2005 |
| EP | 1616531 A2 | 1/2006 |
| EP | 1819304 A2 | 6/2006 |
| EP | 1849440 A1 | 10/2007 |
| EP | 2654624 A1 | 10/2013 |
| WO | WO95/04556 A2 | 2/1995 |
| WO | WO95/29640 A1 | 11/1995 |
| WO | WO96/14032 A1 | 5/1996 |
| WO | WO96/24306 A1 | 8/1996 |
| WO | WO98/36790 A1 | 8/1998 |
| WO | WO98/57599 A2 | 12/1998 |
| WO | WO99/44542 A2 | 9/1999 |
| WO | WO00/09059 A2 | 2/2000 |
| WO | WO00/44308 A2 | 8/2000 |
| WO | WO00/44313 A1 | 8/2000 |
| WO | WO00/67661 A2 | 11/2000 |
| WO | WO01/05331 A1 | 1/2001 |
| WO | WO01/35870 A1 | 5/2001 |
| WO | WO01/64137 A1 | 9/2001 |
| WO | WO02/36048 A1 | 5/2002 |
| WO | WO02/41789 A2 | 5/2002 |
| WO | WO02/100297 A2 | 12/2002 |
| WO | WO03/003943 A2 | 1/2003 |
| WO | WO03/003949 A2 | 1/2003 |
| WO | WO03/011195 A2 | 2/2003 |
| WO | WO03/030776 A2 | 4/2003 |
| WO | WO03/015851 A1 | 11/2003 |
| WO | WO03/094797 A1 | 11/2003 |
| WO | WO2004/014256 A1 | 2/2004 |
| WO | WO2004/019811 A2 | 3/2004 |
| WO | WO2004/026117 A2 | 4/2004 |
| WO | WO2004/041126 A1 | 5/2004 |
| WO | WO2004/047681 A1 | 6/2004 |
| WO | WO2004/066876 A1 | 8/2004 |
| WO | WO2004/082536 A1 | 9/2004 |
| WO | WO2005/037361 A2 | 4/2005 |
| WO | WO2005/084595 A1 | 9/2005 |
| WO | WO2005/087140 A1 | 9/2005 |

(56) References Cited

FOREIGN PATENT DOCUMENTS

| WO | WO2009/072122 A1 | 6/2009 |
|---|---|---|
| WO | WO2009/108615 A1 | 9/2009 |
| WO | WO2009/132187 A1 | 10/2009 |
| WO | WO2009/137755 A2 | 11/2009 |
| WO | WO2010/057262 A1 | 5/2010 |
| WO | WO2010/141847 A1 | 12/2010 |
| WO | WO2011/057087 A1 | 5/2011 |
| WO | WO2011/081997 A1 | 7/2011 |
| WO | WO2012/161786 A1 | 11/2012 |
| WO | WO2013/158608 A1 | 10/2013 |
| WO | WO2013/158613 A1 | 10/2013 |
| WO | WO2014/121280 A2 | 8/2014 |
| WO | WO2014/144247 A1 | 9/2014 |
| WO | WO2015/127283 A1 | 8/2015 |
| WO | WO2016/168609 A1 | 10/2016 |
| WO | WO2016/183523 A1 | 11/2016 |
| WO | WO2017/035002 A1 | 3/2017 |
| WO | WO2017/035434 A1 | 3/2017 |
| WO | WO2017/122109 A1 | 7/2017 |
| WO | WO2017/167759 A1 | 10/2017 |
| WO | WO2017/218877 A1 | 12/2017 |
| WO | 2019023385 A1 | 1/2019 |

OTHER PUBLICATIONS

Atwood et al.; Insertion of Heart Valves by Catheterization; Project Supervised by Prof. S. Muftu of Northeastern University, May 2002: pp. 36-40.
Bodnar et al. Replacement Cardiac Valves; (Chapter 13) Extinct cardiac valve prostheses. Pergamon Publishing Corporation. New York, Aug. 1991: pp. 307-322.
Boudjemline et al. Percutaneous implantation of a biological valve in the aorta to treat aortic valve insufficiency—a sheep study.f Med Sci. Monit; Apr. 2002; vol. 8, No. 4: BR113-116.
Boudjemline et al. "Percutaneous implantation of a valve in the descending aorta in lambs." Euro. Heart J; Jul. 2002; 23: 1045-1049.
Boudjemline et al. "Percutaneous pulmonary valve replacement in a large right ventricular outflow tract: an experimental study." Journal of the Americal College of Cardiology; Mar. 2004; vol. 43(6): 1082-1087.
Boudjemline et al. "Percutaneous valve insertion: A new approach?" J. of Thoracic and Cardio. Surg; Mar. 2003; 125(3): 741-743.
Boudjemline et al. "Steps Toward Percutaneous Aortic Valve Replacement." Circulation; Feb. 2002; 105: 775-778.
Cribier et al. "Early Experience with Percutaneous Transcatheter Implantation of Heart Valve Prosthesis for the Treatment of End-Stage Inoperable Patients with Calcific Aortic Stenosis." J. of Am. Coll. of Cardio; Feb. 2004; 43 (4): 698-703.
Cribier et al. "Percutaneous Transcatheter Implantation of an Aortic Valve Prosthesis for Calcific Aortic Stenosis: First Human Case Description." Circulation; Dec. 2002; 106: 3006-3008.
Cribier et al. "Percutaneous Transcatheter Implantation of an Aortic Valve Prosthesis for Calcific Aortic Stenosis: First Human Case." (slide presentation); TCT 2002 (conference); 16 pgs.; Washington D.C.; Sep. 24-28, 2002.
Ferrari et al. "Percutaneous transvascular aortic valve replacement with self expanding stent-valve device." Poster from the presentation given at SMIT 2000, 12th International Conference. 1 pg. Sep. 5, 2000.
Hijazi "Transcatheter Valve Replacement: A New Era of Percutaneous Cardiac Intervention Begins." J. of Am. College of Cardio; Mar. 2004; 43(6): 1088-1089.

Huber et al. "Do valved stents compromise coronary flow?" European Journal of Cardio-thoracic Surgery; May 2004; vol. 25: 754-759.
Knudsen et al. "Catheter-implanted prosthetic heart valves." Int'l J. of Art. Organs; May 1993; 16(5): 253-262.
Kort et al. "Minimally invasive aortic valve replacement: Echocardiographic and clinical results." Am. Heart J; Sep. 2001; 142(3): 476-481.
Love et al. fThe Autogenous Tissue Heart Valve: Current Stat.f Journal of Cardiac Surgery; Dec. 1991; 6(4): 499-507.
Lutter et al. "Percutaneous aortic valve replacement: An experimental study. I. Studies on implantation." J. of Thoracic and Cardio. Surg; Apr. 2002; 123(4): 768-776.
Moulopoulos et al. "Catheter-Mounted Aortic Valves." Annals of Thoracic Surg; May 1971; 11(5): 423-430.
Paniagua et al. "Percutaneous heart valve in the chronic in vitro testing model." Circulation; Sep. 2002; 106: e51-e52.
Paniagua et al. Heart Watch (2004). Texas Heart Institute. Spring Mar. 2004 Edition: 8 pages.
Pavcnik et al. "Percutaneous bioprosthetic veno valve: A long-term study in sheep." J. of Vascular Surg; Mar. 2002; 35(3): 598-603.
Phillips et al. "A Temporary Catheter-Tip Aortic Valve: Hemodynamic Effects on Experimental Acute Aortic Insufficiency." Annals of Thoracic Surg; Feb. 1976; 21(2): 134-136.
Sochman et al. "Percutaneous Transcatheter Aortic Disc Valve Prosthesis Implantation: A Feasibility Study." Cardiovasc. Intervent. Radiol; Sep.-Oct. 2000; 23: 384-388.
Solvay; Novel revivent(tm) Myocardial anchoring system from bioVentrix uses solvay's zeniva® PEEK in tether component; 3 pages retrieved from the internet (http://www.solvay.com/en/media/press_release/20131205-novel-revivent-myocardial-anchoring-system-bioventrix-uses-zenivapeek.html); (Press Release); on Aug. 10, 2017.
Stuart, M. "In Heart Valves, A Brave, New Non-Surgical World." Start-Up; Feb. 2004: 9-17.
Vahanian et al. "Percutaneous Approaches to Valvular Disease." Circulation; Apr. 2004; 109: 1572-1579.
Van Herwerden et al., "Percutaneous valve implantation: back to the future?" Euro. Heart J; Sep. 2002; 23(18): 1415-1416.
Zhou et al. "Self-expandable valved stent of large size: off-bypass implantation in pulmonary position." Eur. J. Cardiothorac; Aug. 2003; 24: 212-216.
Gregg et al.; U.S. Appl. No. 15/573,555 entitled "Cardiac valve delivery devices and systems," filed Nov. 13, 2017.
Noe et al.; U.S. Appl. No. 15/909,610 entitled "Replacement mitral valves," filed Mar. 1, 2018.
Noe et al.; U.S. Appl. No. 15/909,881 entitled "Replacement mitral vlves," filed Mar. 1, 2018.
Noe et al.; U.S. Appl. No. 15/910,484 entitled "Replacement mitral valves," filed Mar. 2, 2018.
Boudjemline et al. "Percutaneous pulmonary valve replacement in a large right ventricular outflow tract: an experimental study." Journal of the American College of Cardiology; Mar. 2004; vol. 43(6): 1082-1087.
Wallace et al., U.S. Appl. No. 16/310,499 entitled "Cardiac valve delivery devices and systems," filed Dec. 17, 2018.
Noe et al.; U.S. Appl. No. 15/908,701 entitled "Replacement mitral valves," filed Feb. 28, 2018.
Wallace et al.; U.S. Appl. No. 15/669,788 entitled "Replacement cardiac valves and methods of use and manufacture," filed Aug. 4, 2017.
Granada et al.; U.S. Appl. No. 15/688,701 entitled "System and method for cardiac valve repair and replacement," filed Aug. 28, 2017.

\* cited by examiner

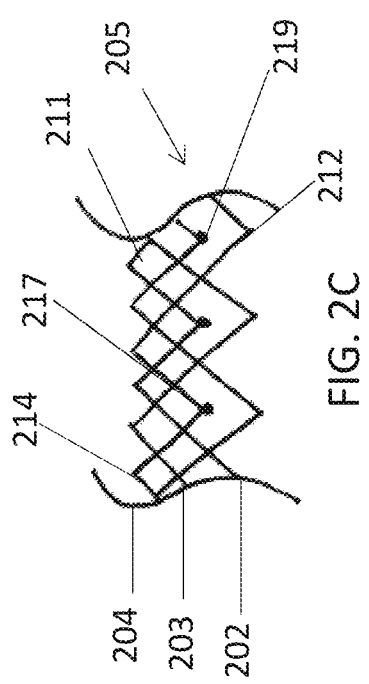

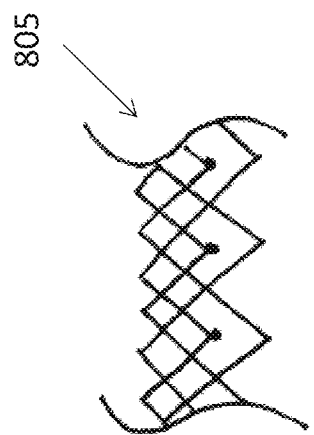

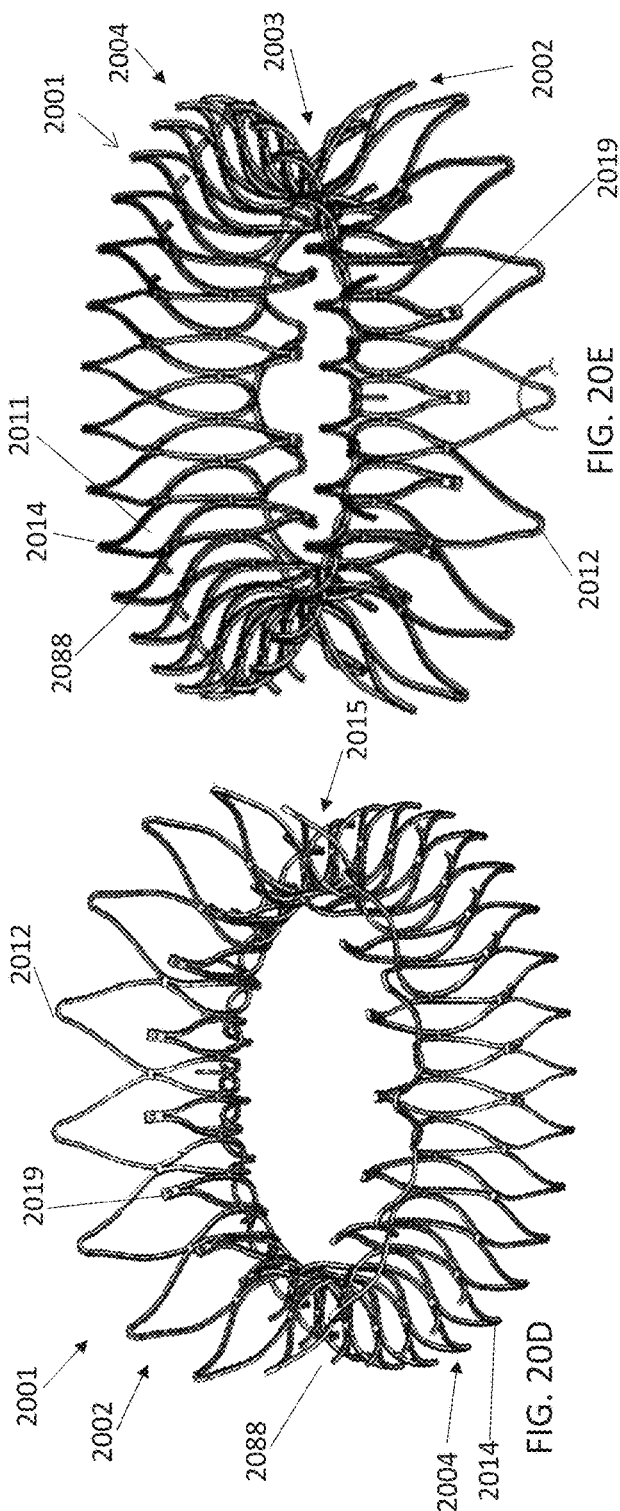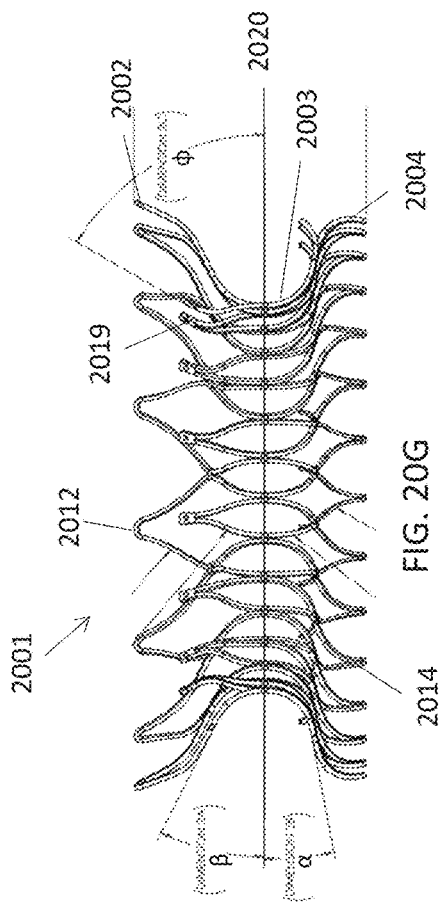
FIG. 20E
FIG. 20G
FIG. 20D

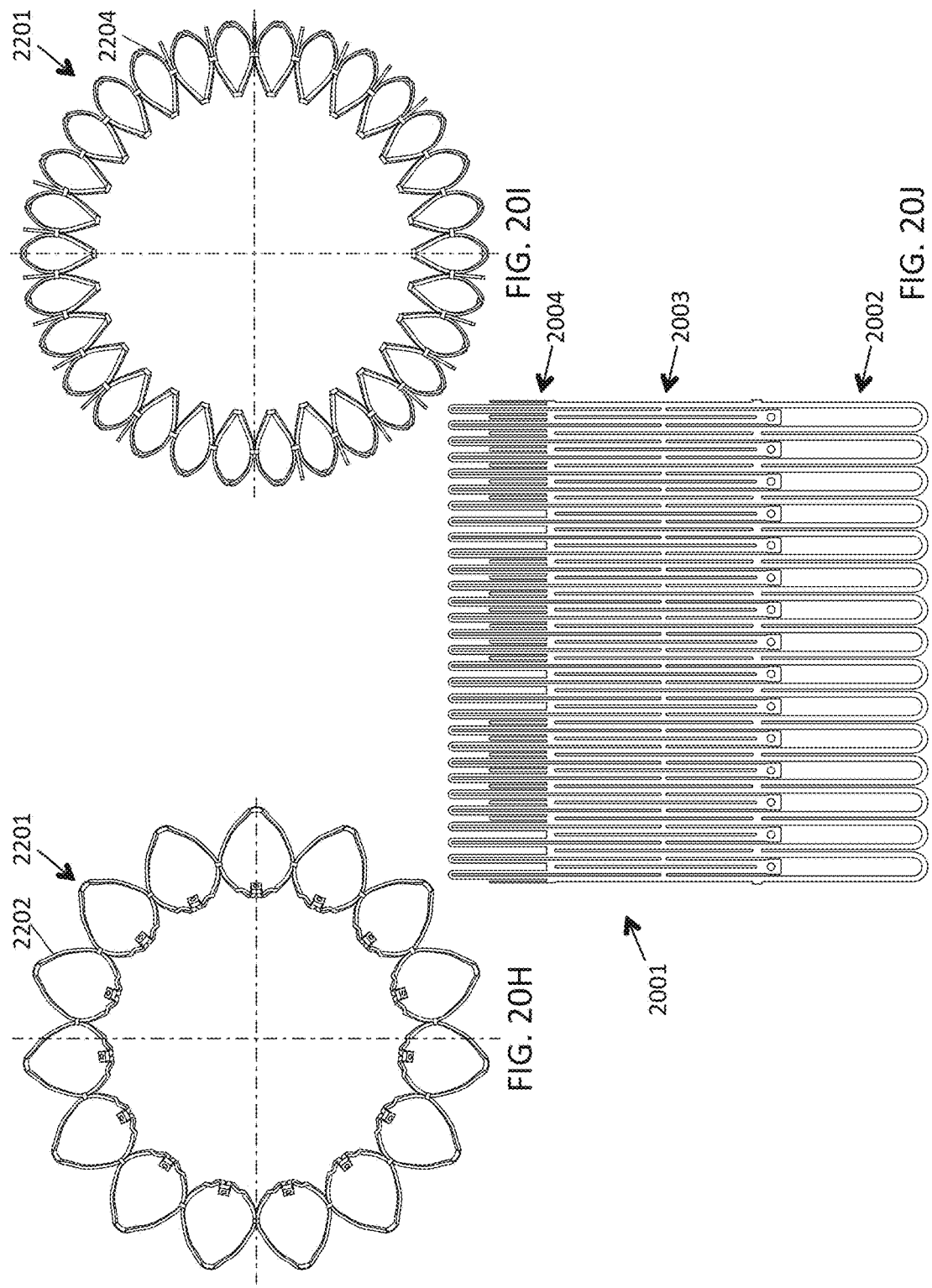

INFLOW

OUTFLOW

REPLACEMENT MITRAL VALVES

CROSS REFERENCE TO RELATED APPLICATIONS

This application is a continuation of International Patent Application No. PCT/US2018/14902, filed Jan. 23, 2018, titled "REPLACEMENT MITRAL VALVES", which claims priority to U.S. Provisional Application No. 62/513,877, filed Jun. 1, 2017 and to U.S. Provisional Patent Application No. 62/449,498, filed Jan. 23, 2017, and titled "REPLACEMENT MITRAL VALVES," the entireties of which are incorporated by reference herein.

This application is also a continuation-in-part of U.S. patent application Ser. No. 15/688,673, filed Aug. 28, 2017, titled "REPLACEMENT MITRAL VALVES," now U.S. Patent Application Publication No. 2018-0000580, which is a continuation of U.S. patent application Ser. No. 15/669,805, filed Aug. 4, 2017, titled "REPLACEMENT MITRAL VALVES," now U.S. Patent Application Publication No. 2017-0325948, which is a continuation of International Patent Application No. PCT/US2016/032550, filed May 13, 2016, titled "REPLACEMENT MITRAL VALVES," which claims priority to U.S. Provisional Patent Application No. 62/259,565, filed Nov. 24, 2015, titled "REPLACEMENT MITRAL VALVES," and U.S. Provisional Patent Application No. 62/161,743, filed May 14, 2015, and titled "REPLACEMENT MITRAL VALVES."

This application may also be related to U.S. patent application Ser. No. 14/170,388, filed Jan. 31, 2014, titled "SYSTEM AND METHOD FOR CARDIAC VALVE REPAIR AND REPLACEMENT," now U.S. Pat. No. 8,870,948, and to U.S. patent application Ser. No. 14/677,320, filed Apr. 2, 2015, titled "REPLACEMENT CARDIAC VALVES AND METHODS OF USE AND MANUFACTURE," the entireties of which are incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND

The mitral valve lies between the left atrium and the left ventricle of the heart. Various diseases can affect the function of the mitral valve, including degenerative mitral valve disease and mitral valve prolapse. These diseases can cause mitral stenosis, in which the valve fails to open fully and thereby obstructs blood flow, and/or mitral insufficiency, in which the mitral valve is incompetent and blood flows passively in the wrong direction.

Many patients with heart disease, including those with mitral valve problems, are intolerant of the trauma associated with open-heart surgery. Age or advanced illness may have impaired the patient's ability to recover from the injury of an open-heart procedure. Additionally, the high costs associated with open-heart surgery and extra-corporeal perfusion can make such procedures prohibitive.

Patients in need of cardiac valve repair or cardiac valve replacement can be served by minimally invasive surgical techniques. In many minimally invasive procedures, small devices are manipulated within the patient's body under visualization from a live imaging source like ultrasound, fluoroscopy, or endoscopy. Minimally invasive cardiac procedures are inherently less traumatic than open procedures and may be performed without extra-corporeal perfusion, which carries a significant risk of procedural complications.

Minimally invasive aortic valve replacement devices, such as the Medtronic Corevalve or the Edwards Sapien, deliver aortic valve prostheses through small tubes which may be positioned within the heart through the aorta via the femoral artery or through the apex of the heart. However, the mitral valve differs from the aortic valve in that the shape and anatomy immediately surrounding the valve varies greatly from one side of the valve to the other. Moreover, current cardiac valve prostheses are not designed to function effectively within the mitral valve. Further, current cardiac valve prostheses delivered via a minimally invasive device are often difficult to place correctly within the native valve, difficult to match in size to the native valve, and difficult to retrieve and replace if initially placed incorrectly.

These and other deficiencies in existing approaches are described herein.

SUMMARY OF THE DISCLOSURE

In general, in one embodiment, a prosthetic mitral valve includes an anchor assembly, a strut frame, and a plurality of replacement leaflets secured to the annular strut frame. The anchor assembly includes a ventricular anchor, an atrial anchor, and a central portion therebetween. The ventricular anchor and the atrial anchor are configured to flare radially outwards relative to the central portion. The annular strut frame is disposed radially within the anchor assembly and is attached to the anchor assembly at a plurality of attachment locations that are positioned between the central portion and an atrial-most edge of the anchor assembly. The central portion is configured to align with a native valve orifice and the ventricular anchor and the atrial anchor are configured to compress native cardiac tissue therebetween.

This and other embodiments can include one or more of the following features. An atrial end of the strut frame can be attached to the anchor assembly. Atrial tips of the strut frame can be attached to the anchor assembly. An atrial end of the strut frame can be flared radially outwards. A flare of the strut frame can be configured to substantially conform to a flare of the atrial anchor. A ventricular end of the strut frame can be spaced away from the anchor assembly. The ventricular end of the strut frame can be spaced away from the anchor assembly by a radial distance of 1-15 mm. The anchor assembly and the strut frame can be configured to self-expand from a constrained configuration to an expanded configuration. The strut frame can be attached to the anchor assembly with a plurality of rivets. Each of the plurality of attachment locations can be radially aligned with tips of the atrial anchor. The plurality of attachment locations can each be part of the anchor assembly that extends further radially inwards than a remaining portion of the anchor assembly. The anchor assembly can comprise a plurality of diamond-shaped cells. The plurality of attachment locations can be positioned at a mid-point of the outermost atrial diamond-shaped cells. The strut frame can include a plurality of linear struts and v-shaped connectors therebetween. The anchor assembly can form a substantially hour-glass shape.

In general, in one embodiment, a prosthetic mitral valve includes an anchor assembly, an annular strut frame, and a plurality of replacement leaflets secured to the annular strut frame. The anchor assembly includes a ventricular anchor, an atrial anchor, and a central portion therebetween. The ventricular anchor and the atrial anchor are configured to flare radially outwards relative to the central portion. Further, the anchor assembly comprises a plurality of diamond-shaped cells. The annular strut frame is disposed radially within the anchor assembly and is attached to the anchor assembly at a plurality of attachment locations that are positioned at a mid-point of the outermost atrial diamond-shaped cells between the central portion and an atrial-most edge of the anchor assembly.

This and other embodiments can include one or more of the following features. An atrial end of the strut frame can be attached to the anchor assembly. Atrial tips of the strut frame can be attached to the anchor assembly. An atrial end of the strut frame can be flared radially outwards. A flare of the strut frame can be configured to substantially conform to a flare of the atrial anchor. A ventricular end of the strut frame can be spaced away from the anchor assembly. The ventricular end of the strut frame can be spaced away from the anchor assembly by a radial distance of 1-15 mm. The anchor assembly and the strut frame can be configured to self-expand from a constrained configuration to an expanded configuration. The strut frame can be attached to the anchor assembly with a plurality of rivets. Each of the plurality of attachment locations can be radially aligned with tips of the atrial anchor. The plurality of attachment locations can each be part of the anchor assembly that extends further radially inwards than a remaining portion of the anchor assembly. The strut frame can include a plurality of linear struts and v-shaped connectors therebetween. The anchor assembly can form a substantially hour-glass shape.

In general, in one embodiment, a prosthetic mitral valve includes an anchor assembly, an annular strut frame, and a plurality of replacement leaflets secured to the annular strut frame. The anchor assembly further includes a ventricular anchor, an atrial anchor, and a central portion therebetween. The ventricular anchor and the atrial anchor are configured to flare radially outwards relative to the central portion. Further, the atrial anchor includes a plurality of atrial cells and the ventricular anchor includes a plurality of ventricular cells. The annular strut frame is disposed radially within the anchor assembly. A first plurality of the atrial cells are positioned radially inwards relative to a second plurality of the atrial cells such that the first plurality of cells attach the strut frame to the anchor assembly.

This and other embodiments can include one or more of the following features. The central portion can be configured to align with a native valve orifice, and the ventricular anchor and the atrial anchor can be configured to compress native cardiac tissue therebetween. An atrial end of the strut frame can be attached to the anchor assembly. Atrial tips of the strut frame can be attached to the anchor assembly. An atrial end of the strut frame can be flared radially outwards. A flare of the strut frame can be configured to substantially conform to a flare of the atrial anchor. A ventricular end of the strut frame can be spaced away from the anchor assembly. The ventricular end of the strut frame can be spaced away from the anchor assembly by a radial distance of 1-15 mm. The anchor assembly and the strut frame can be configured to self-expand from a constrained configuration to an expanded configuration. The strut frame can be attached to the anchor assembly with a plurality of rivets. The first plurality of atrial cells can end in disconnected apexes. The disconnected apexes can be radially aligned with outer-most tips of the second plurality of atrial cells. The first plurality of atrial cells can be angled at approximately 70-80 degrees relative to the axis that extends through the central portion. The second plurality of atrial cells can be angled at approximately 20-30 degrees relative to the axis that extends through the central portion. The annular strut frame can flare radially outwards at 70-80 degrees relative to the axis that extends through the central portion.

In general, in one embodiment, a prosthetic mitral valve includes an anchor assembly, an annular strut frame, and a plurality of replacement leaflets secured to the annular strut frame. The anchor assembly includes a ventricular anchor, an atrial anchor, and a central portion therebetween. The ventricular anchor and the atrial anchor are configured to flare radially outwards relative to the central portion. Further, the atrial anchor includes a plurality of atrial cells. The annular strut frame is disposed radially within the anchor assembly. A first plurality of the atrial cells are interior disconnected apexes and the second plurality of atrial cells are outermost atrial cells. The first plurality positioned radially inwards relative to a second plurality of the atrial cells such that the first plurality of cells attach the strut frame to the anchor assembly.

This and other embodiments can include one or more of the following features. The central portion can be configured to align with a native valve orifice. The ventricular anchor and the atrial anchor can be configured to compress native cardiac tissue therebetween. An atrial end of the strut frame can be attached to the anchor assembly. Atrial tips of the strut frame can be attached to the anchor assembly. An atrial end of the strut frame can be flared radially outwards. A flare of the strut frame can be configured to substantially conform to a flare of the atrial anchor. A ventricular end of the strut frame can be spaced away from the anchor assembly. The ventricular end of the strut frame can be spaced away from the anchor assembly by a radial distance of 1-15 mm. The anchor assembly and the strut frame can be configured to self-expand from a constrained configuration to an expanded configuration. The strut frame can be attached to the anchor assembly with a plurality of rivets. The disconnected apexes can be radially aligned with outer-most tips of the second plurality of atrial cells. The first plurality of atrial cells can be angled at approximately 70-80 degrees relative to an axis that extends through the central portion. The second plurality of atrial cells can be angled at approximately 20-30 degrees relative to the axis that extends through the central portion. The annular strut frame can flare radially outwards at 70-80 degrees relative to the axis that extends through the central portion.

In general, in one embodiment, a prosthetic mitral valve includes a valve support assembly that includes a ventricular anchor and an atrial anchor. The valve support assembly has a plurality of slots therethrough. The prosthetic mitral valve further includes a plurality of replacement leaflets. Each leaflet has a leaflet arm extending through one of the plurality of slots. The prosthetic mitral valve further includes a plurality of commissure plates. Each commissure plate is circumferentially and axially aligned with one of the plurality of slots to form a commissure attachment mechanism. Each commissure plate further includes a plurality of channels in the sides thereof. The at least one suture is positioned at each commissure attachment mechanism and is wrapped around a portion of the valve support assembly, through the plurality of indents, and around the commissure plate.

This and other embodiments can include one or more of the following features. The valve support assembly can include an anchor assembly that includes the ventricular and atrial anchors and an annular strut frame that includes the plurality of slots. The annular strut frame can be positioned radially within the anchor assembly. The plurality of slots can be in a portion of the strut frame that extends past the anchor assembly in the ventricular direction. The anchor assembly can further include a central portion, and the ventricular and atrial anchors can flare radially outwards relative to the central portion. The plurality of channels can extend from the sides of each commissure plate towards a center of the plate. The plurality of channels can be substantially straight. There can be between 6 and 12 channels in each commissure plate. Each of the slots can be in an axially extending strut. Arms of the leaflets can extend through the plurality of slots. The arms can be further be wound around an outer perimeter of an inner strut frame of the valve support assembly. The plurality of slots can be positioned equidistance around a circumference of the valve support assembly. Each of the plurality of slots can be positioned towards a ventricular end of the valve support assembly. The valve support assembly can be configured to self-expand from a constrained configuration to an expanded configuration. Atrial edges of the leaflets can be sewn around an inner circumference of the valve support assembly. Each of the leaflets further includes a leaflet protector thereon. The leaflet protector can be made of a lubricious fabric and can be configured to protect the respective leaflet from an inner circumference of the valve support assembly.

In general, in one embodiment, a prosthetic mitral valve includes a valve support assembly. The valve support assembly includes an anchor assembly having a ventricular anchor and an atrial anchor and an annular strut frame positioned radially within the anchor assembly. The annular strut frame includes a plurality of slots therethrough. The prosthetic mitral valve further includes a plurality of replacement leaflets. Each leaflet has a leaflet arm extending through one of the plurality of slots. The prosthetic mitral valve further includes a plurality of commissure plates. Each commissure plate is circumferentially and axially aligned with one of the plurality of slots to form a commissure attachment mechanism. Each commissure plate further includes a plurality of channels in the sides thereof.

This and other embodiments can include one or more of the following features. The prosthetic mitral valve can include at least one suture at each commissure attachment mechanism. The at least one suture can be positioned around the strut frame, through the plurality of indents, and around the commissure plate. The plurality of slots can be in a portion of the strut frame that extends past the anchor assembly in the ventricular direction. The anchor assembly can further include a central portion, and the ventricular and atrial anchors can be flared radially outwards relative to the central portion. The plurality of channels can extend from the sides of each commissure plate towards a center of the plate. The plurality of channels can be substantially straight. There can be between 6 and 12 channels in each commissure plate. Each of the slots can be in an axially extending strut. The arms of the leaflets can extend through the plurality of slots. The arms can be further be wound around an outer perimeter of the strut frame. The plurality of slots can be positioned equidistance around a circumference of the strut frame. Each of the plurality of slots can be positioned towards a ventricular end of the strut frame. The valve support assembly can be configured to self-expand from a constrained configuration to an expanded configuration. Atrial edges of the leaflets can be sewn around an inner circumference of the strut frame. Each of the leaflets can further include a leaflet protector thereon. The leaflet protector can be made of a lubricious fabric and can be configured to protect the leaflet from an inner circumference of the valve support assembly.

In general, in one embodiment, a prosthetic mitral valve includes a valve support assembly, a plurality of leaflets secured to the valve support assembly, and a plurality of retention hooks. The valve support assembly includes a ventricular anchor, a central portion, and an atrial anchor. The valve support assembly is configured to self-expand from a collapsed configuration to an expanded configuration. The plurality of retention hooks are attached to the ventricular anchor. Each of the retention hooks curves radially outwards to point in an atrial direction when the valve support assembly is in the expanded configuration. Each retention hook has a ratio of radius of curvature to thickness of between 4:1 and 6:1.

This and other embodiments can include one or more of the following features. Each of the plurality of retention hooks can be configured to point at an angle of 50°-80° relative to a central longitudinal axis of the prosthetic mitral valve. The angle can be approximately 65°. A radius of curvature of each of the plurality of retention hooks can be between 3-5 mm. A thickness of each retention hooks can be between 0.8 mm and 1.6 mm. The plurality of retention hooks can be integral with the valve support assembly. The valve support assembly can include an anchor assembly that further includes the ventricular and atrial anchors and the central portion and an annular strut frame positioned radially within the anchor assembly. The plurality of retention hooks can be attached to the anchor assembly. The central portion can be configured to align with a native valve orifice, and the ventricular anchor and the atrial anchors can be configured to compress native cardiac tissue therebetween. The valve support assembly can include a plurality of diamond-shaped cells. Each of the retention hooks can extend from an apex of an interior diamond-shaped cell. A retention hook can extend from each apex in a circumferential line around the prosthetic mitral valve except at positions closest to leaflet attachment points.

In general, in one embodiment, a prosthetic mitral valve includes a valve support assembly, a plurality of leaflets secured to the valve support assembly, and a plurality of retention hooks. The valve support assembly includes a ventricular anchor, a central portion, and an atrial anchor. Each of the retention hooks is attached to the ventricular anchor and curves radially outwards to point in an atrial direction. Each retention hook has a ratio of radius of curvature to thickness of between 4:1 and 6:1 and points at an angle of 50°-80° relative to a central longitudinal axis of the prosthetic mitral valve.

This and other embodiments can include one or more of the following features. The angle can be approximately 65°. A radius of curvature of each of the plurality of retention hooks can be between 3-5 mm. A thickness of each retention hooks can be between 0.8 mm and 1.6 mm. The plurality of retention hooks can be integral with the valve support assembly. The valve support assembly can include an anchor assembly that further includes the ventricular and atrial anchors and the central portion and an annular strut frame positioned radially within the anchor assembly. The plurality of retention hooks can be attached to the anchor assembly. The central portion can be configured to align with a native valve orifice, and the ventricular anchor and the atrial anchors can be configured to compress native cardiac tissue therebetween. The valve support assembly can include a plurality of diamond-shaped cells. Each of the retention hooks can extend from an apex of an interior diamond-shaped cell. A retention hook can extend from each apex in a circumferential line around the prosthetic mitral valve except at positions closest to leaflet attachment points.

In general, in one embodiment, a replacement mitral valve includes a self-expandable valve support assembly that includes a ventricular anchor, a central portion, and an atrial anchor. The valve support assembly has a self-expanded configuration in which the ventricular anchor and the atrial anchor are flared radially outward relative to the central portion. The atrial anchor has a larger diameter than the ventricular anchor when the valve assembly is in the self-expanded configuration. The replacement mitral valve further includes a plurality of replacement leaflets secured to the valve assembly.

This and other embodiments can include one or more of the following features. The ventricular anchor can have outer diameter of less than 55 mm. The atrial anchor can have diameter that is 3-10% larger than diameter of ventricular anchor. The valve support assembly can include an anchor assembly that includes the central portion and ventricular and atrial anchors. The valve support assembly can further include an annular strut frame positioned radially within the anchor assembly. The anchor assembly can be made of a plurality of diamond-shaped cells joined together. The valve support assembly can be configured to self-expand from a constrained configuration to an expanded configuration. The anchor assembly can be configured to foreshorten when transitioning from the constrained configuration to the expanded configuration. The anchor assembly can be configured to take on an hour-glass shape. Tips of the atrial anchor can point in a ventricular direction. The atrial and ventricular anchors can be configured to compress native cardiac tissue therebetween. The atrial anchor can include a plurality of atrial tips and the ventricular anchor can include a plurality of ventricular tips. There can be more ventricular tips than atrial tips.

In general, in one embodiment, a replacement mitral valve includes a valve support assembly that includes a ventricular anchor, a central portion, and an atrial anchor. The valve support assembly has a self-expanded configuration in which the ventricular anchor and the atrial anchor are flared radially outward relative to the central portion. The atrial anchor has a diameter that is 3-10% larger than a diameter of the ventricular anchor. The replacement mitral valve further includes a plurality of replacement leaflets secured to the valve assembly.

This and other embodiments can include one or more of the following features. The ventricular anchor can have outer diameter of less than 55 mm. The valve support assembly can include an anchor assembly including the central portion and ventricular and atrial anchors. The valve support assembly can further include an annular strut frame positioned radially within the anchor assembly. The anchor assembly can be made of a plurality of diamond-shaped cells joined together. The valve support assembly can be configured to self-expand from a constrained configuration to an expanded configuration. The anchor assembly can be configured to foreshorten when transitioning from the constrained configuration to the expanded configuration. The anchor assembly can be configured to take on an hour-glass shape. Tips of the atrial anchor can point in a ventricular direction. The atrial and ventricular anchors can be configured to compress native cardiac tissue therebetween. The atrial anchor can include a plurality of atrial tips and the ventricular anchor can include a plurality of ventricular tips. There can be more ventricular tips than atrial tips.

In general, in one embodiment, a prosthetic mitral valve includes an anchor assembly that includes a ventricular anchor, an atrial anchor, and a central portion therebetween. The anchor assembly is configured to compress native cardiac tissue between the ventricular anchor and the atrial anchor. An annular strut frame is disposed radially within the anchor assembly and attached thereto. The prosthetic mitral valve further includes a plurality of replacement leaflets secured to the annular strut frame. The anchor assembly and annular strut frame are configured to self expand from a collapsed configuration to an expanded configuration. The anchor assembly is configured to foreshorten along a central axis of the prosthetic mitral valve when expanding from the collapsed configuration to the expanded configuration. The annular strut frame is configured to be substantially non-foreshortening along the central axis when expanding from the collapsed configuration to the expanded configuration.

This and other embodiments can include one or more of the following features. The anchor assembly can include a plurality of diamond-shaped cells. The ventricular anchor can include a plurality of struts and v-shaped connecting members. The ventricular anchor and atrial anchors can flare radially outwards relative to the central portion when in the expanded configuration. The anchor assembly can be configured to foreshorten by 20-30% when self-expanding from the collapsed configuration to the expanded configuration.

In general, in one embodiment, a prosthetic mitral valve includes an anchor assembly that includes a ventricular anchor, an atrial anchor, and a central portion therebetween. The anchor assembly is configured to compress native cardiac tissue between the ventricular anchor and the atrial anchor. An annular strut frame is disposed radially within the anchor assembly such that the annular strut frame is spaced radially away from the central portion of the anchor assembly. The prosthetic mitral valve further includes a plurality of replacement leaflets secured to the annular strut frame.

This and other embodiments can include one or more of the following features. The annular strut frame can be spaced radially away from the central portion by 2-3 mm. The annular strut frame can be flared at an atrial end. Atrial tips of the annular strut frame can be attached to the anchor assembly. A portion of the anchor assembly can be pulled radially inwards relative to a remainder of the anchor assembly so as to attach to the annular strut frame.

In general, in one embodiment, a prosthetic mitral valve includes a valve assembly that includes a ventricular anchor, a central portion, and an atrial anchor. The anchor assembly is configured to expand from a collapsed configuration to an expanded configuration. The atrial anchor includes a plurality of atrial cells forming peaks and valleys around a circumference thereof, and the ventricular anchor includes a plurality of ventricular cells forming peaks and valleys around a circumference thereof. A plurality of replacement leaflets are secured to the valve assembly. A plurality of retention hooks are attached only to the ventricular anchor. Each of the plurality of retention hooks is positioned in a valley between the ventricular cells when the valve assembly is in the expanded configuration.

This and other embodiments can include one or more of the following features. The plurality of retention hooks can curve to point in the atrial direction when the anchor assembly is in the expanded configuration. The valve assembly can be configured to self-expand. The plurality of retention hooks can point at an angle of 50°-80° relative to a central longitudinal axis of the prosthetic mitral valve. The plurality of retention hooks can be positioned in every valley except valleys closest to leaflet attachment points.

In general, in one embodiment, a prosthetic mitral valve includes an anchor assembly that includes a ventricular anchor, a central portion, and an atrial anchor. The anchor assembly configured to expand from a collapsed configuration to an expanded configuration. The atrial anchor includes a plurality of atrial cells at an atrial edge of the atrial anchor, and the ventricular anchor includes a plurality of ventricular cells at a ventricular edge of the ventricular anchor. The number of ventricular cells is divisible by 2, and the number of atrial cells is divisible by 3. An annular strut frame is positioned within the anchor assembly and includes a plurality of struts connected by connection members. Three of the struts include commissure attachment points. The three commissure attachment points are spaced equally around a circumference of the annular strut frame. Three replacement leaflets are secured to the annular strut frame at the commissure attachment points.

This and other embodiments can include one or more of the following features. There can be 30 ventricular cells, 15 atrial cells, and 15 struts. There can be 24 ventricular cells, 12 atrial cells, and 12 struts. There can be more ventricular cells than atrial cells. The number of ventricular cells can also be divisible by 3.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 1A-1B show the mitral valve prosthesis in an expanded configuration. FIG. 1C shows a portion of the expanded anchor assembly in 2D.

FIGS. 2A-2E show another exemplary mitral valve prosthesis. FIGS. 2A-2B show the mitral valve prosthesis in an expanded configuration. FIG. 2C shows a portion of the expanded anchor assembly in 2D. FIG. 2D shows the expanded annular strut frame. FIG. 2E shows a 2D pattern (pre-expanded) for the strut frame.

FIGS. 3A-3B show the mitral valve prosthesis in an expanded configuration. FIG. 3C shows the expanded annular strut frame.

FIGS. 8A-8G show another exemplary mitral valve prosthesis. FIGS. 8A-8C show the mitral valve prosthesis in the expanded configuration. FIGS. 8D-8E show the expanded anchor assembly. FIG. 8F shows a portion of the expanded anchor assembly in 2D. FIG. 8G shows a 2D pattern (pre-expanded) for the anchor assembly.

FIGS. 9A-9C show the anchor assembly in the expanded configuration. FIG. 9D shows a 2D pattern (pre-expanded) for the anchor assembly.

FIG. 11A shows an exemplary commissure plate. FIG. 11B shows a cross-sectional view of leaflets extending between the two commissure plates. FIG. 11C shows a valve assembly having a strut with a series of holes therein for attachment of leaflets to the valve assembly. FIG. 11D shows a cross-sectional view of the leaflets and commissure plates attached to the strut. FIG. 11E shows a close-up of a portion of the strut with holes therein.

FIG. 15A shows a secondary member including a slot. FIG. 15B is a cross-sectional view showing the leaflets passed through the slot of the secondary member and around a strut of the strut frame.

FIG. 15C shows alignment of the secondary member and the strut.

FIG. 18A shows a plate attached to a valve assembly to attach the leaflets thereto. FIG. 18B is a cross-sectional view showing the leaflets attached between the plate and a strut. FIG. 18C is a top view of the exemplary mechanism. FIG. 18D shows the plate positioned over two leaflets and a strut of the valve assembly. FIG. 18E shows the plate attached to the strut frame.

FIG. 20A shows the exemplary mitral valve prosthesis in the expanded configuration. FIGS. 20D-20G show the expanded anchor assembly. FIG. 20H shows the atrial end of the expanded valve prosthesis. FIG. 20I shows the ventricular end of the expanded valve prosthesis. FIG. 20J is a 2D view of the (unexpanded) anchor assembly.

FIGS. 20P-20Q are additional view of the expanded prosthesis without the leaflets or skirt for clarity.

FIG. 27A shows a strut frame with a slot in the strut and a first suture positioned therearound.

27F-27H show placement of the leaflet arms through the slot in the strut frame. FIG. 27Q shows wrapping of the final suture around the plate to attach the leaflets to the strut frame.

FIG. 29A shows the expanded valve assembly with pins therein. FIG. 29B shows a close-up of a pin. FIG. 29C shows slots in the skirt to allow for access to the pins. FIG. 29D shows a 2D (unexpanded) view of the anchor assembly with pins. FIG. 29E shows a close-up of a pin with dimensions.

DETAILED DESCRIPTION

This disclosure includes replacement heart valves (also referred to herein as prosthetic heart valves), methods of manufacturing replacement heart valves, including subassemblies thereof, and methods of using replacement heart valves. This disclosure describes the prostheses in the context of replacement mitral valves, but it is conceivable that the prostheses herein can be used or modified to be used as other replacement heart valves. In some embodiments, the replacement heart valves are self-orienting replacement mitral valves configured to be delivered using minimally invasive techniques.

The replacement heart valves described herein include an anchor assembly that includes an atrial anchor (e.g., configured to be placed on an atrial side of a mitral valve annulus), a ventricular anchor (e.g., configured to be placed on a ventricular side of a mitral valve annulus), and a central portion positioned axially between the atrial and ventricular anchors. The anchor assembly is adapted to collapse to a delivery or collapsed configuration and expand to an expanded configuration. The replacement heart valves also include a strut frame secured to at least one of the central portion, the ventricular anchor, or the atrial anchor for attaching a plurality of replacement leaflets thereto. The strut frame can be configured to deform and collapse as the rest of the anchor assembly is collapsed. The struts of the strut frame extend towards and/or past the ventricular anchor.

The replacement heart valves described herein are configured to be secured in the native valve orifice by sandwiching the cardiac orifice between ventricular and atrial anchors, which are larger in diameter than the valve orifice, by applying an axial compressive force from the anchors, a radial force from the center portion outward against the cardiac orifice, and/or by using hooks or barbs that extend into the tissue of the orifice.

Further, the replacement heart valves described herein can be delivered to a cardiac valve orifice, such as the mitral valve, by using minimally invasive techniques to access the cardiac valve. In some embodiments, the mitral valve prostheses can be delivered through a transatrial route, i.e., by making a small incision in the patient's body and passing the prosthesis through the apex of the heart to, for example, the mitral valve. In other embodiments, the mitral valve prostheses can be delivered through the transseptal route, i.e., through the venous system and into the left atrium via a transseptal puncture. In both the transatrial and transseptal delivery methods, the distal-most anchor can be delivered to the ventricle while the proximal-most anchor can be delivered to the atrium.

Figure 1A:
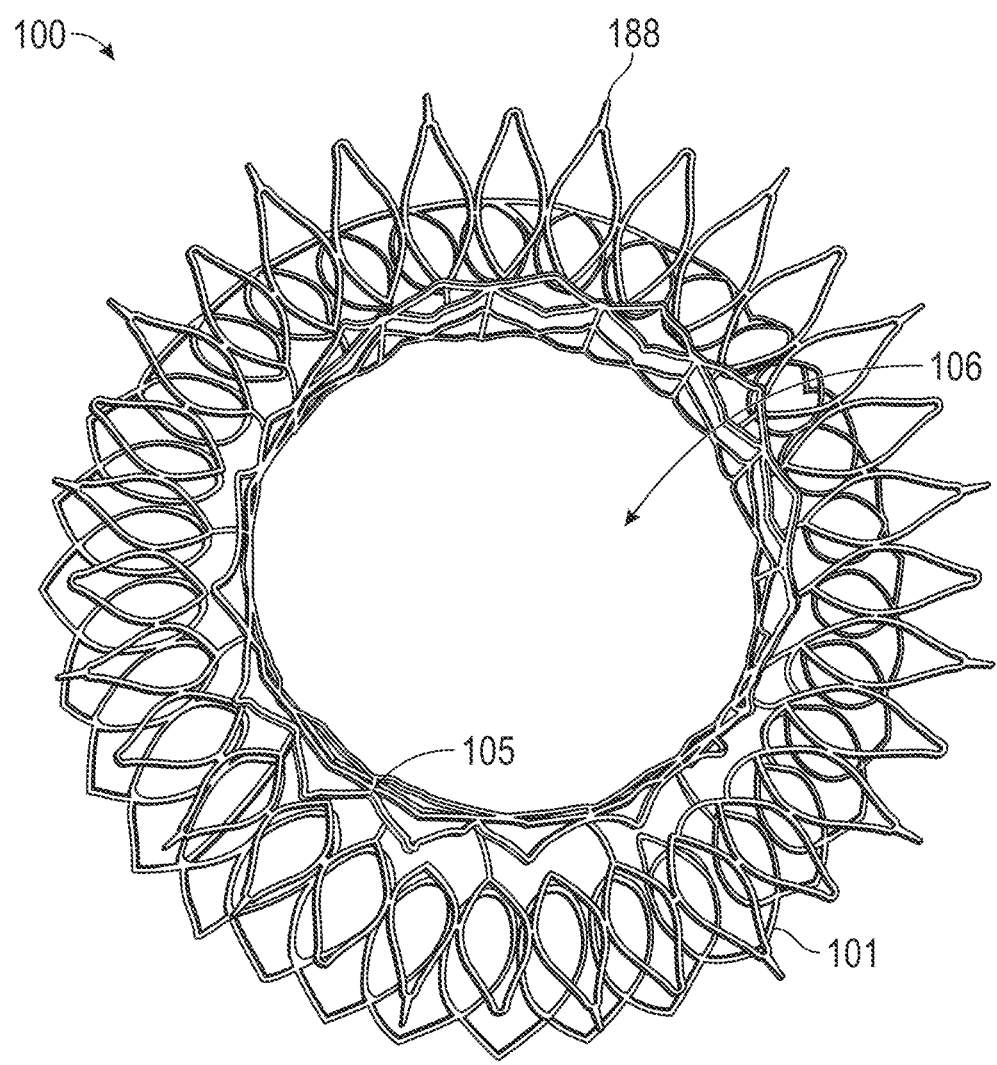
FIGS. 1A-1C show an exemplary mitral valve prosthesis.
Figure 1B:
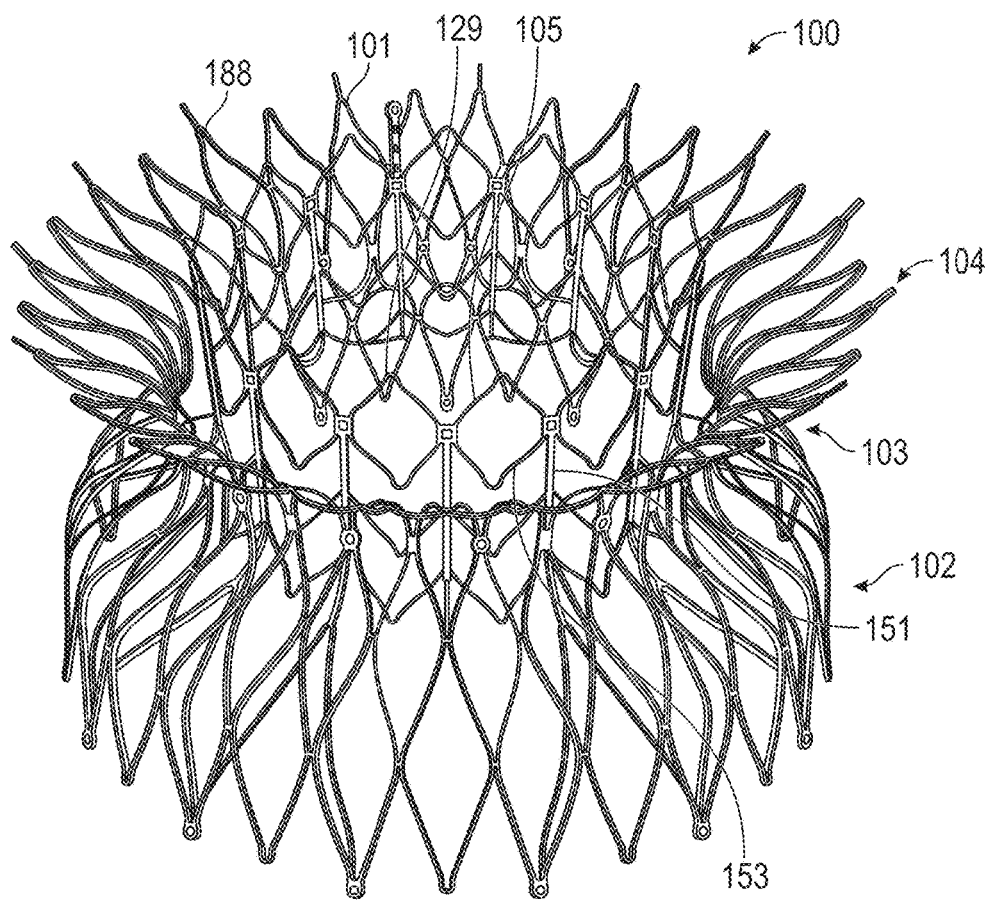
Figure 1C:
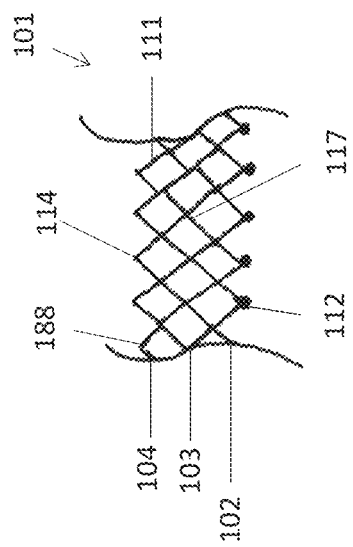

FIGS. 1A-1C show an exemplary mitral valve prosthesis 100 in an expanded configuration. The portion of the replacement valve prosthesis 100 in FIG. 1 may be referred to as a prosthesis subassembly, which includes an anchor assembly 101 and a strut frame 105, but excludes leaflets and any skirts that may be incorporated into the final replacement valve. Anchor assembly 101 includes an atrial anchor 102, a ventricular anchor 104, and a central portion 103 therebetween. In this embodiment, atrial anchor 102 is configured and adapted to be disposed on an atrial side of a mitral valve orifice, and ventricular anchor 104 is configured and adapted to be disposed on a ventricle side of the mitral valve orifice. Further, the central portion 103 can be configured to be situated in the mitral valve orifice. In some embodiments, the central portion 103 has a diameter that is substantially the same size as the native mitral valve annulus (i.e., it is not designed to be larger than the annulus).

In some embodiments, the anchor assembly 101 and/or strut frame 105 can be made of wire, such as a shape memory metal wire (e.g., a nitinol). In other embodiments, the anchor assembly and/or strut frame can be laser cut from one or more tubes, such as a shape memory metal tube (e.g., nitinol). For example, the anchor assembly 101 can be laser cut from a first hypotube while the strut frame 105 can be laser cut from a second hypotube of smaller diameter. The anchor assembly 101 can be cut, for example, from a 9-12 mm diameter tube, such as a 10 mm tube, while the strut frame 105 can be cut, for example, from a 7-9 mm diameter tube, such as an 8 mm tube.

The valve prosthesis 100 can be configured to expand (e.g., self-expand) from a collapsed or constrained (delivery) configuration to an expanded (treatment) configuration. In the expanded configuration shown in FIGS. 1A-1B, the atrial anchor 102 and ventricular anchor 104 extend radially outward from central portion 103, and are considered to flare outward relative to central portion 103. The atrial anchor 102 and ventricular anchor 104 can also be considered flanged relative to central portion 103. The flared configuration of atrial and ventricular anchors 102 and 104 relative to central portion 103 is described in the context of a side view of the anchor assembly, as can be best seen in FIG. 1B. In some embodiments, the flared configuration of the two anchors 102, 104 and the central portion 103 define a general hour-glass shape in a side view of the anchor assembly 101. That is, the anchors 102, 104 can be flared outwards relative to the central portion 103 and then curved or bent to point at least partially back in the axial direction. It should be understood, however, that an hour-glass configuration is not limited to symmetrical configuration.

The anchor assembly 101 can be configured to expand circumferentially and foreshorten axially as the valve prosthesis 100 expands from the collapsed delivery configuration to the expanded treatment configuration. For example, as shown in FIGS. 1A-1C, the anchor assembly 101 can be made of a plurality of cells 111 that are each configured to expand circumferentially and foreshorten axially upon expansion of the anchor assembly 101. As shown best in FIG. 1C, the cells 111 can each be diamond-shaped. Further, the cells 111 can be interconnected and configured such that every diamond apex 117 is connected to another diamond apex 117 except at the atrial or ventricular tips 112, 114 of the assembly 101. The anchor assembly 101 can include, for example, three circumferential rows of diamond cells 111. For example, the atrial anchor 102 can comprises one row of diamond-shaped cells 111 extending circumferentially, the central portion 103 can comprise one row of diamond-shaped cells 111 extending circumferentially, and the ventricular anchor 104 can comprise one row of diamond-shaped cells extending circumferentially 111.

The strut frame 105 can be configured to expand circumferentially, but maintain the same axial dimension (i.e., be non-foreshortening) as the valve prosthesis 100 expands from the collapsed delivery configuration to the expanded treatment configuration. By being non-foreshortening, the strut frame 105 can advantageously ensure that less strain is placed on the leaflets during delivery and/or packing. Thus, while the anchor assembly 101 is designed to be foreshortening, the strut frame 105 is designed so as to be substantially non-foreshortening. As can be best seen in FIG. 1B, the strut frame 105 can include a plurality of longitudinally extending struts 151 and interconnecting v-shaped members 153. Further, in some embodiments, and again as shown in FIGS. 1A-1B, the strut frame 105 can have fewer v-shaped members 151 extending circumferentially around the diameter thereof than the cells 111 of the anchor assembly 101, such as half the number. Further, the strut frame 105 can flare at radially outwards at the atrial end, e.g., to conform to the flare of the atrial anchor 102.

The strut frame 105 and the anchor assembly 101 can be coupled together with coupling members, such as rivets. In some embodiments, and as shown in FIGS. 1A-1B, the atrial tips 129 of the strut frame 105 can be coupled to the atrial tips 112 of the anchor assembly 101. Where there are fewer v-shaped members 151 in the strut frame 105 than cells 111 in the anchor assembly 101 (as shown in FIG. 1B), the strut frame 105 can attach to every other atrial tip 112 on the anchor assembly 101.

The radially inner surfaces of strut frame 105 can substantially define the perimeter of a central opening 106. Replacement leaflets, which are not shown in FIGS. 1A-1B for clarity, can be secured to the strut frame 105 and can be disposed at least partially in the central opening 106. The leaflets are configured to control blood flow therethrough.

In some embodiments, the valve 100 can include hooks 188 or barbs to help anchor the assembly in the mitral valve orifice. As shown in FIGS. 1A-1C, in one embodiment, the hooks 188 can be on the ventricular most tips 114 of the ventricular anchor 104.

FIGS. 2A-2E show another exemplary valve prosthesis 200. The valve prosthesis 200 is similar to valve prosthesis 100 and can include many of the same features as valve prosthesis 100, such as an anchor assembly 201 (having atrial anchor 202, a ventricular anchor 204, and a central portion 203) and a strut frame 205. In contrast to the prosthesis 100, the cells 211 of the anchor 201 are not connected together at every interior apex 217. Rather, the middle row of cells 211 can be disconnected at every other atrial apex 219 at the atrial side. As a result, there can be fewer atrial tips 212 than ventricular tips 214, and the atrial-most cells can be truncated or v-shaped (i.e., straddling each disconnected apex 219 and corresponding diamond-shaped cell). For example, there can be 15 atrial tips 212 (and 15 v-shaped cells 211 at the atrial end) and 30 ventricular tips 214 (and 30 diamond-shaped cells at the ventricular end). Advantageously, because the atrial tips 212 are larger/wider than the ventricular tips 214, the atrial tips 212 can be more flexible to allow the atrial anchor 202 to conform to the tissue. The atrial apexes 219 can be radially aligned with the atrial tips 212 and can be positioned approximately mid-way along the diamond-shaped cells at the atrial tips 212 along the central longitudinal axis (as noted above, the outermost cells can also be considered v-shaped, particularly in 2D, as the inner cell and apex 219 sit within the outer larger diamond, making it a v-shape).

Figure 2A:
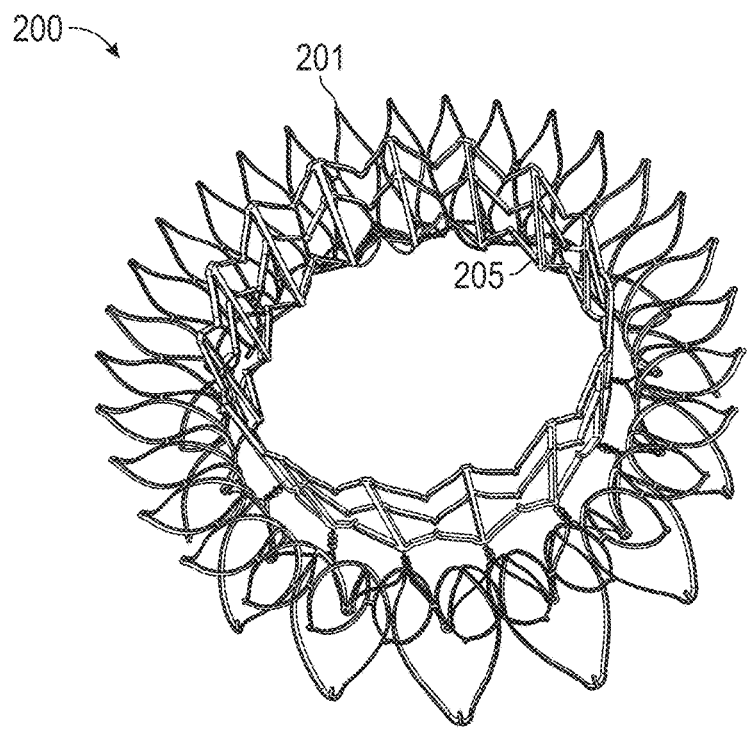
Figure 2B:
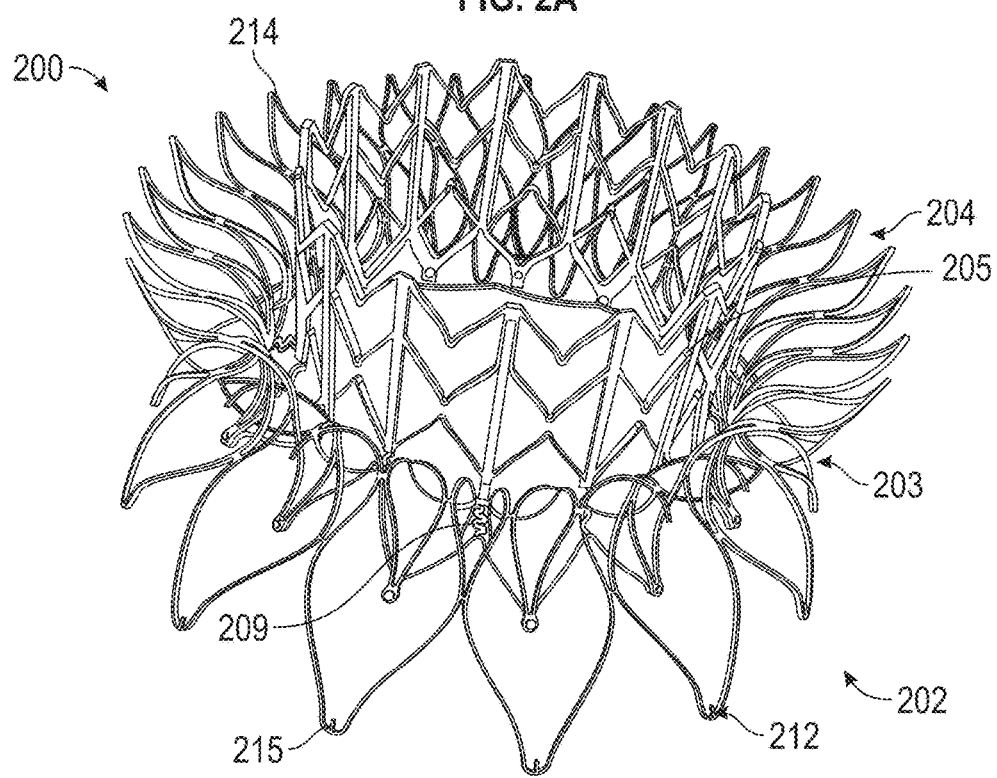

In some embodiments, each of the atrial apexes 219 can have a rivet hole therein for connection to the atrial tips 229 of the strut frame 205. Further, in some embodiments (and as shown in FIGS. 2A and 2B), the atrial apexes 219 can all be bent slightly radially inwards towards the strut frame 205 (e.g., further radially inwards than the rest of the anchor assembly 201 so as to meet the strut frame 205). The atrial apexes 219 can be radially aligned with the atrial tips 212 of the atrial anchor 202. Further, the apexes 219, when bent radially inwards, can effectively act as an integrated suspension, holding the central portion 203 and ventricular anchor 204 radially outwards relative to, and spatially separated from, the strut frame 205. For example, the ventricular anchor 204 can be separated from the strut frame 205 by a radial distance of, for example, 1-15 mm, such as 2-11 mm, such as approximately 3 mm. Further, the central portion 203 can be separated from the strut frame 205 by a radial distance of, for example, 2-3 mm. This separation of the ventricular anchor 204 and/or the central portion 203 can advantageously isolate the leaflets from the anchor assembly 201 on the ventricular side where the greatest amount of distortion is placed on the anchor assembly 201.

Further, in this embodiment, the strut frame 205 and anchor assembly 201 can be attached at a central point of the atrial anchor 202 (i.e., at apexes 219) rather than at the outer-most or atrial-most tips 212 of the atrial anchor 202. By attaching the inner strut frame 205 to the anchor assembly 201 at a mid-point of the atrial anchor 202 rather than at the atrial tips 212, less torque or torsion is applied to the strut frame 205 as the atrial anchor 202 conforms to the tissue, thereby helping to ensure that the leaflets maintain their required position.

Figure 2D:
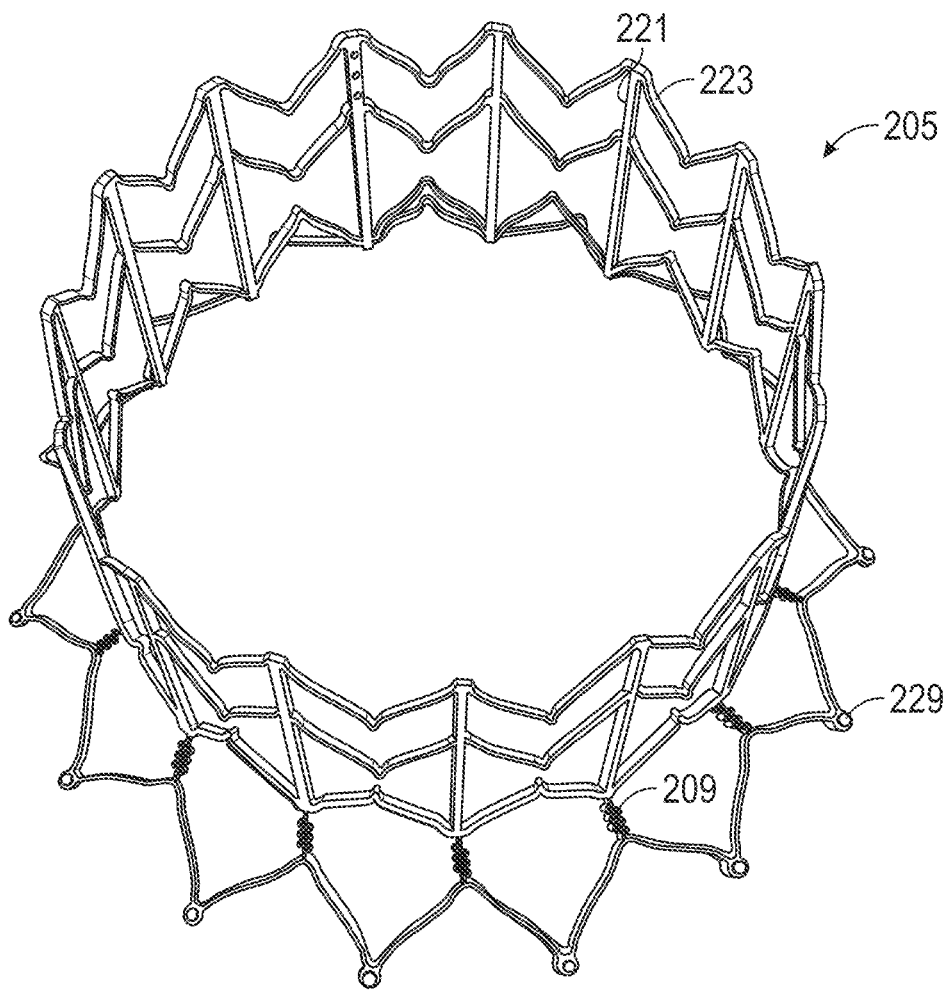
Figure 2E:
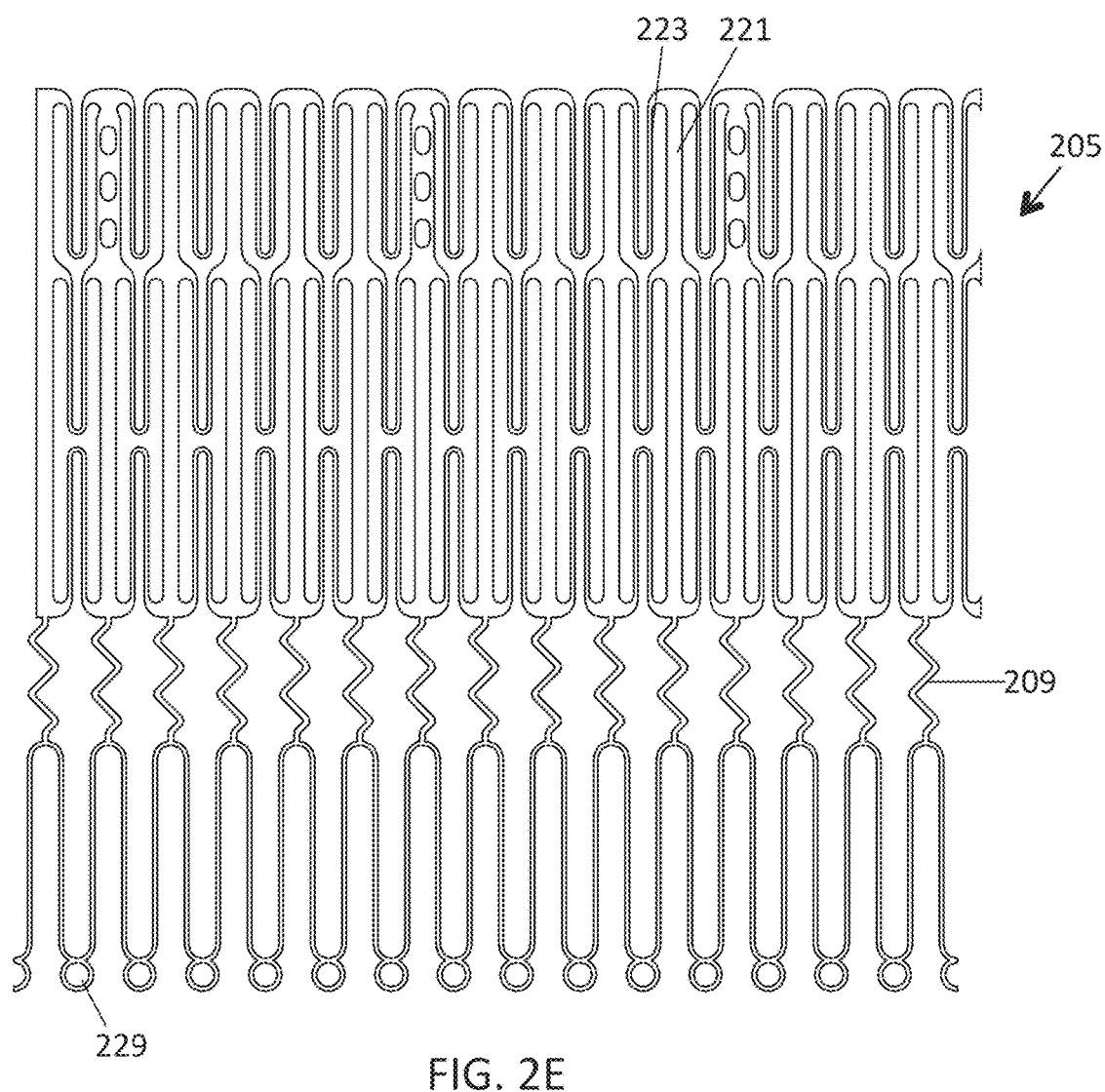

As shown best in FIGS. 2D and 2E, the strut frame 205 can include a plurality of struts 221 and v-shaped members 223 (so as to be substantially non-foreshortening as described with respect to strut frame 105). In this embodiment, there are four v-shaped members 223 extending axially between each pair of struts 221. The two ventricular-most v-shaped members 223 and the atrial-most v-shaped member 223 all point in the atrial direction. The last v-shaped member 223 points in the ventricular direction. Having a v-shaped member 223 that points in the ventricular direction can add to the stiffness of the strut frame 205. Additionally, having the last v-shaped member 223 point towards the atrium reduces the length of the struts and reduces the number of vertices that are pointed into the ventricle (to reduce trauma to the ventricle). The atrial tips 229 of the strut frame 205 can be formed by the vertex of the "V" shape. Each atrial tip 229 can include a rivet hole therein for connection to the anchor assembly 201. Further, the strut frame 205 can include a flare at the atrial end thereof to enable the strut frame to meet the apexes 219 and/or to conform to the flare of the atrial anchor 202. Further, in some embodiments (and as shown in FIG. 2D), the flare at the atrial end of the strut frame 205 can include relatively flexible members 209 or zig-zag features therein.

The flexible members 209 can be configured to allow the atrial flare to easily fold up during packing/delivery.

In some embodiments, the number of ventricular cells or ventricular tips 214 in valve 200 (or any valve described herein) can be divisible by both 2 and 3. For example, there can be 18, 24, or 30 ventricular cells or tips 214. Because the number of ventricular tips 214 is divisible by 2, there can be half as many atrial tips 212. Further, by having the number of cells divisible by 3, the three attachment points for the three leaflets (e.g., struts 221a,b,c) of the strut frame 205 can be even spaced around the circumference of the central opening 206. Increasing the number of ventricular tips/cells (e.g., from 18 cells to 30 cells) in any given design means that the total amount of required circumferential expansion of each individual cell decreases, thereby allowing the longitudinal lengths of the cells to be shorter, decreasing the overall length of the packed assembly (i.e., during delivery). In some embodiments, the cells have a length of between 4 and 6 mm and a width of between 0.2 and 0.4 mm when collapsed, e.g., before expansion. With these dimensions, the packed assembly can be, for example, 30-40 mm, such as 32-35 mm. Further, in some embodiments, the cell dimensions are chosen such that the ratio of width to length yields no more than 8-10% sheathing strain when the anchor assembly is retracted into the catheter for delivery.

Figure 3A:
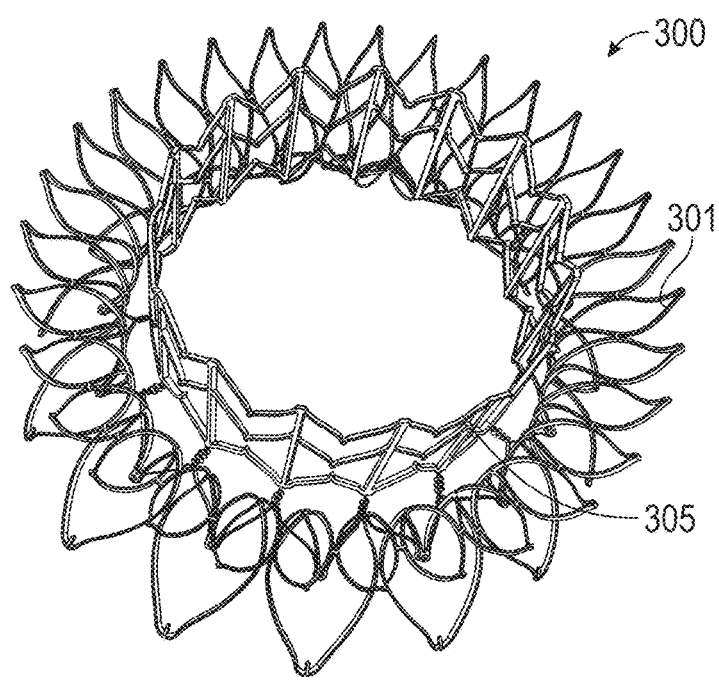
FIG. 3A-3C show another exemplary mitral valve prosthesis.
Figure 3B:
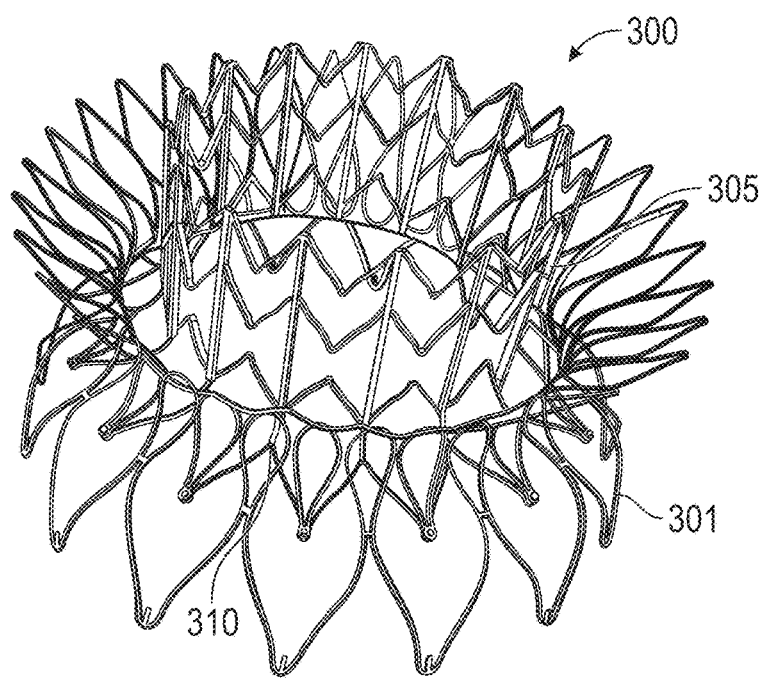
Figure 3C:
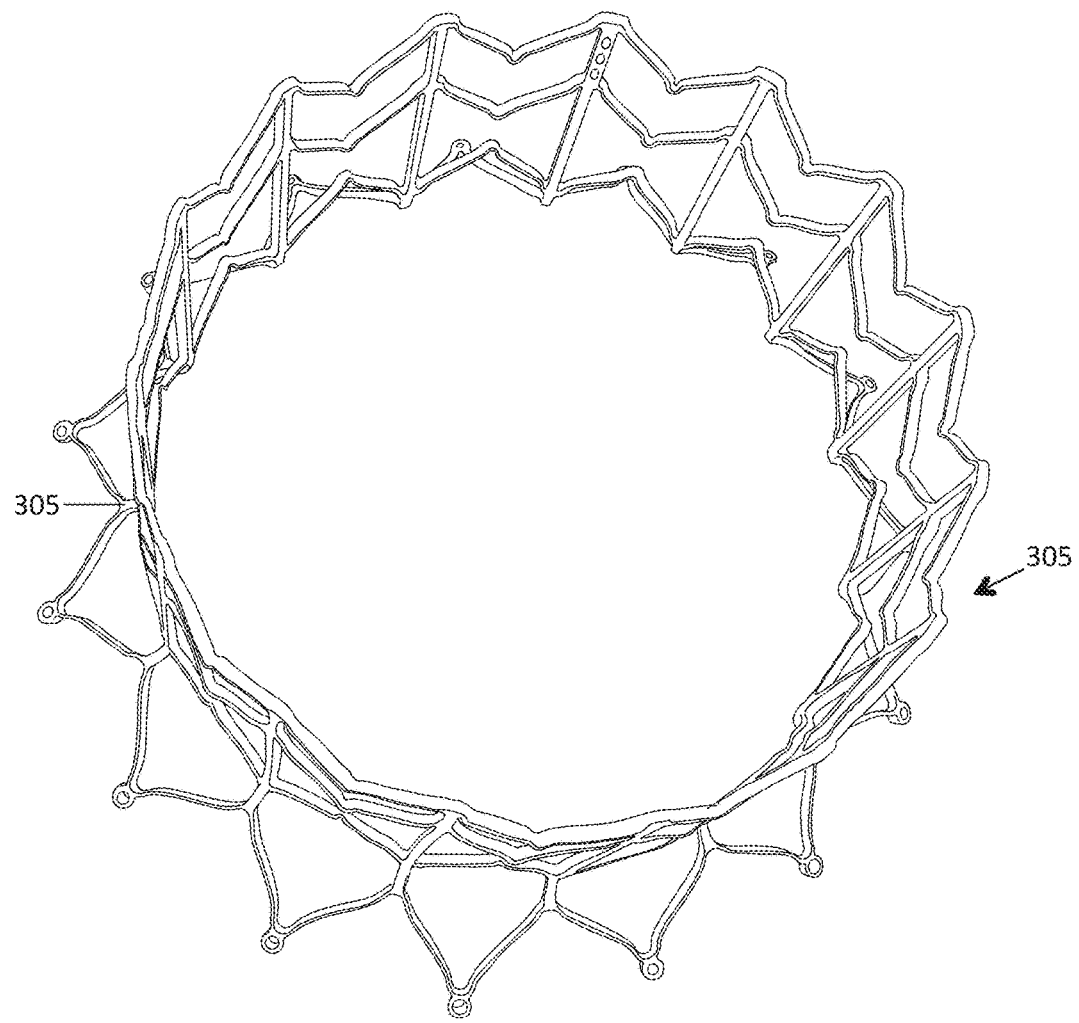

FIGS. 3A-3C show another exemplary valve prosthesis 300. Valve prosthesis 300 is similar to valve prosthesis 200 (with anchor assembly 301 similar to assembly 201). The strut frame 305, however, includes reduced thickness members 310 in the atrial flare rather than flexible members 209. The reduced thickness members 310 can have a smaller diameter than the rest of the strut frame 305. The reduced thickness members 310, similar to the flexible members 209, can allow for easier bending at the flare of the strut frame 305, thereby permitting easy packing.

Figure 4A:
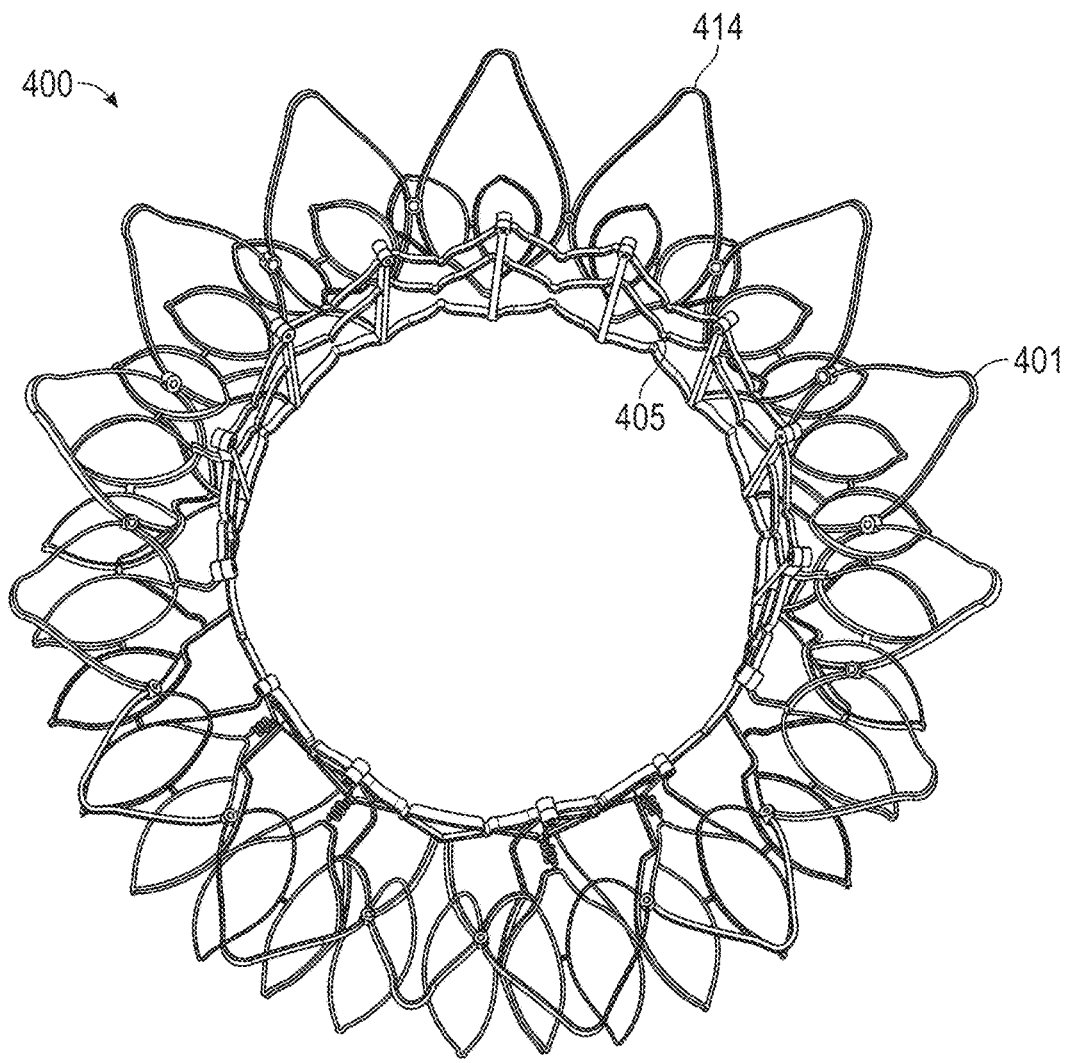
FIGS. 4A-4C show another exemplary mitral valve prosthesis in an expanded configuration.
Figure 4B:
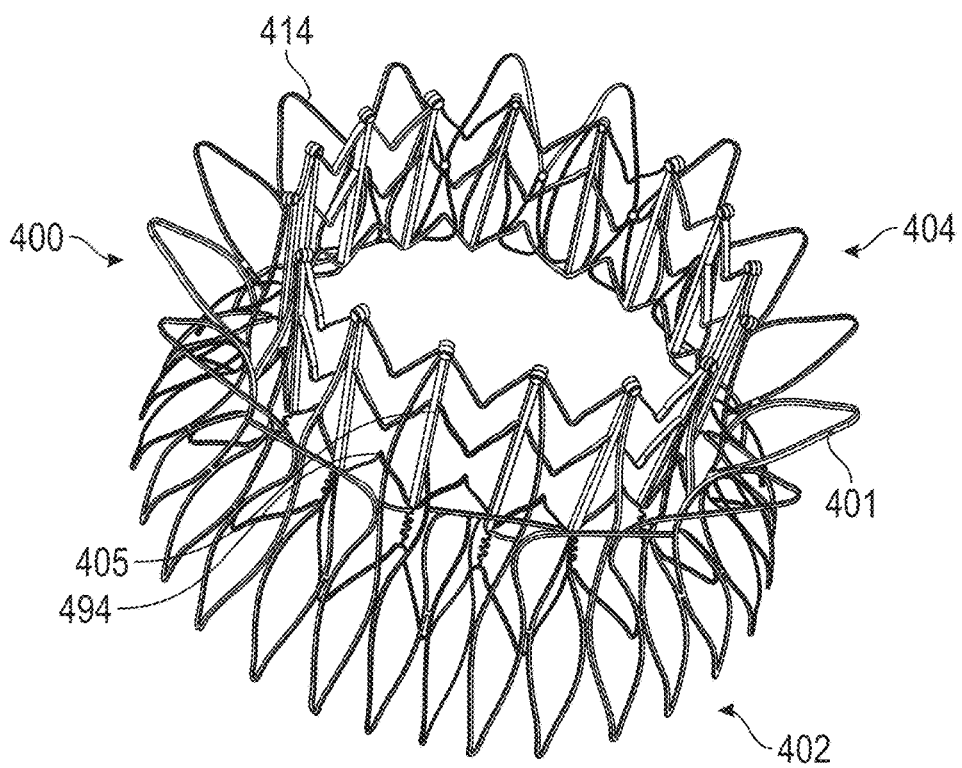
Figure 4C:
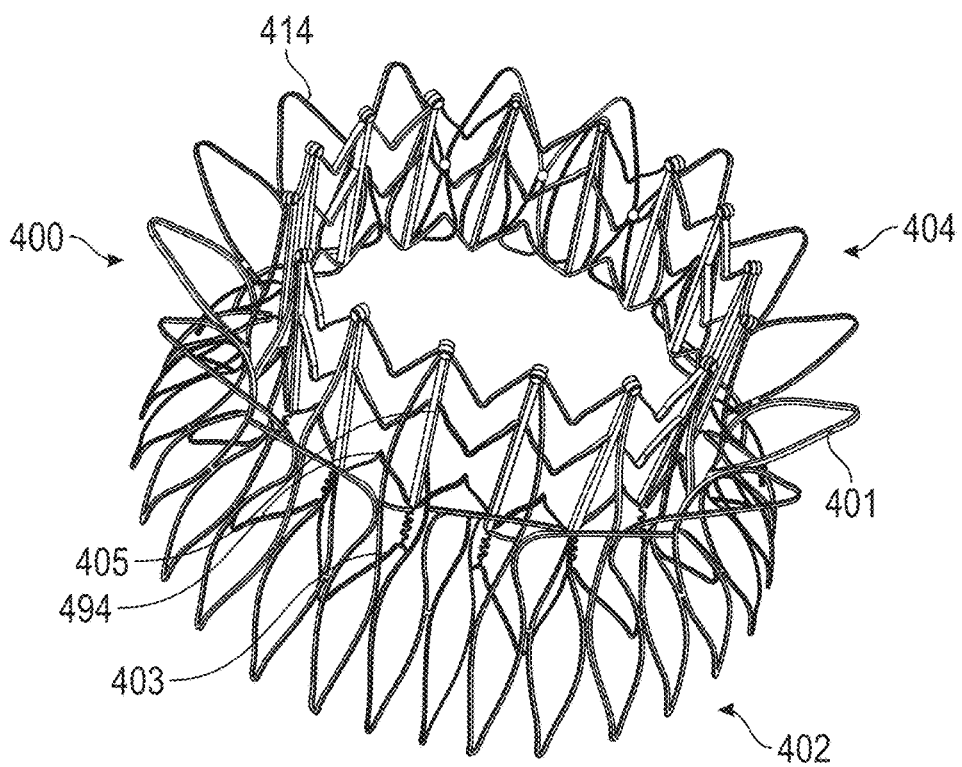

FIGS. 4A-4C show another exemplary valve prosthesis 400. The valve 400 is similar to valves 100-300 except that the attachment point between the strut frame 405 and the anchor assembly 401 is at the ventricular end of the strut frame 405. To connect the anchor assembly 401 to the ventricular end of the strut frame 405, connecting members 494 extend from the anchor assembly 401 (e.g., from the central portion 403 or the ventricular anchor 404) to the ventricular tips of the strut frame 405. The connecting members 494 can be integral, for example, with the anchor assembly 401 and then riveted to the strut frame 405. In some embodiments, as shown in FIGS. 4A-4C, the connecting members 414 can be a single longitudinal member. In other embodiments, the connecting members 494 can be cells or tips 414 of the ventricular anchor 404 that are pulled radially inwards (e.g., every other tip 414 of the ventricular anchor 404 can be pulled inwards). Further, in some embodiments, an additional layer of cells can be coupled or riveted to the ventricular anchor 404 to tune the rigidity thereof. As shown in FIGS. 4A-4C, the atrial end of the strut frame 405 can still be flared at an angle, e.g., to substantially confirm to the flare of the atrial anchor 402 of the anchor assembly 401.

FIGS. 8A-8G show another exemplary valve prosthesis 800 including valve assembly 801 and strut frame 805. Valve prosthesis 800 is similar to valve prosthesis 200 except that valve prosthesis 800 has a greater curvature on the flare of the ventricular anchor 804, which can help improve retention force in some embodiments. For example, the ventricular anchor 804 can flare at an initial angle of 5°-15°, such as 10°, relative to a horizontal plane through the central portion 803 (and/or 75°-95°, such as 80°, relative to a central axis through the prosthesis 800). Additionally, the anchor assembly 801 includes a plurality of barbs or hooks 888 extending from the ventricular anchor 804. Positioning the hooks on the ventricular anchor 804 advantageously helps hold the prosthesis in place, as the ventricular side of the mitral valve undergoes the highest pressure. The hooks 888 are positioned in the valleys between the ventricular tips 814. Further, each hook 888, when the anchor assembly 801 is in the expanded configuration, is curved backwards to point at least partially in the atrial direction.

Figure 20A:
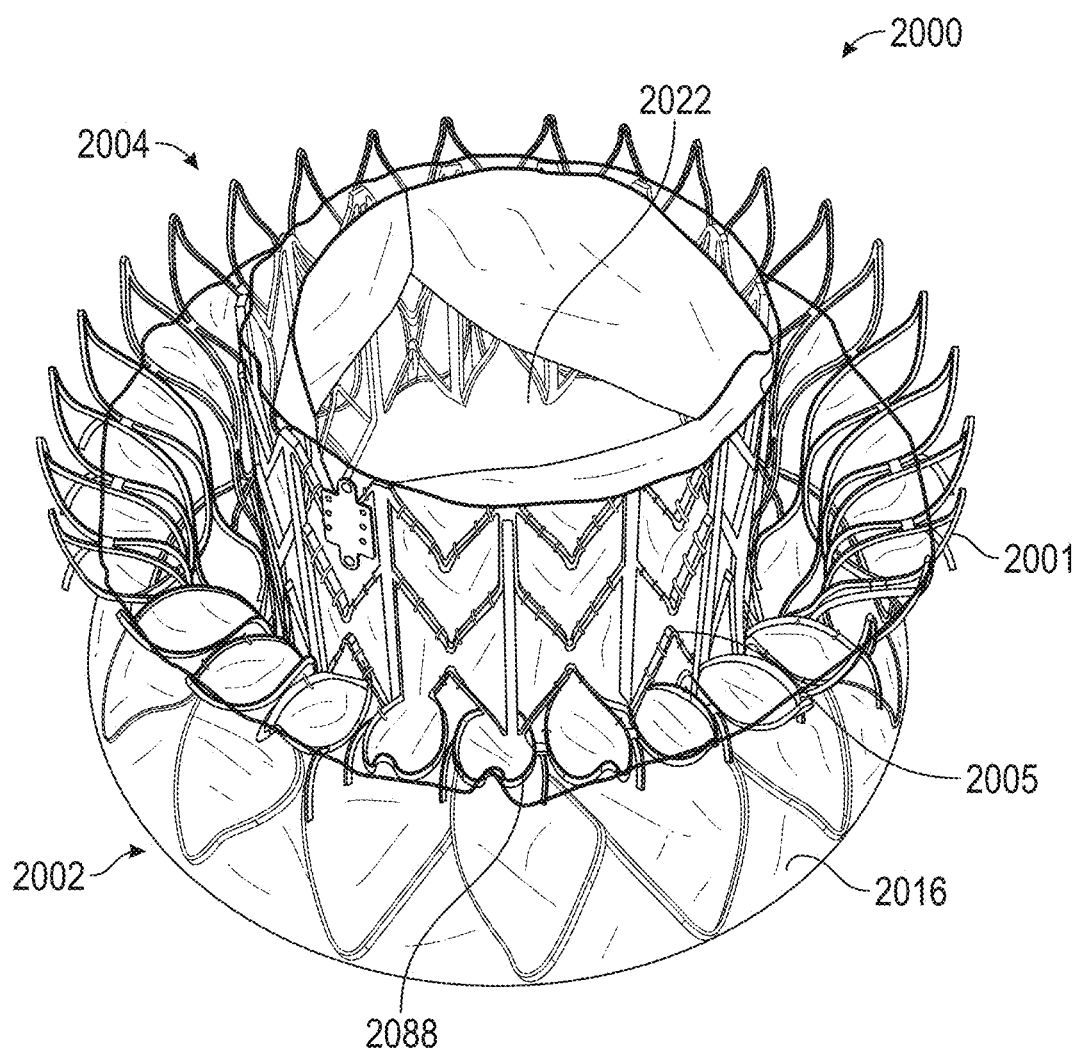
FIGS. 20A-20Q show another exemplary mitral valve prosthesis.
Figure 20B:
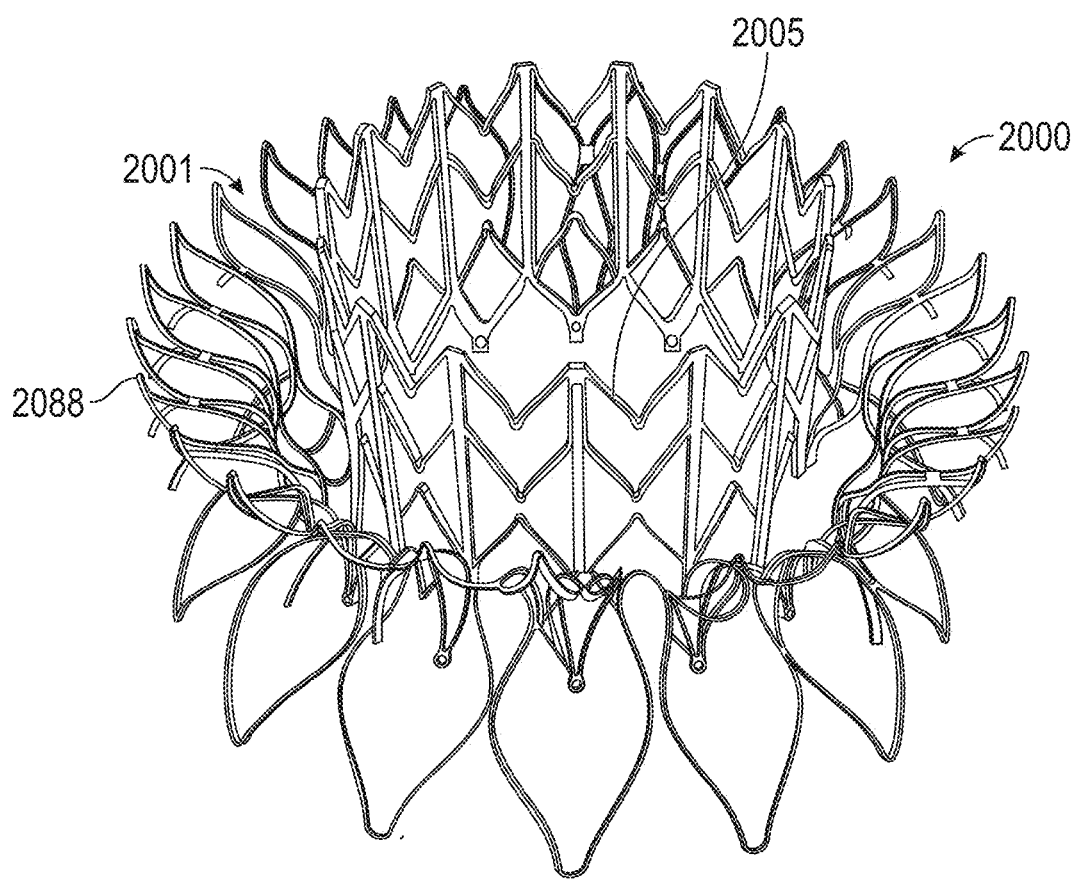
FIGS. 20B-20C show the expanded prosthesis without the leaflets or skirt for clarity.
Figure 20C:
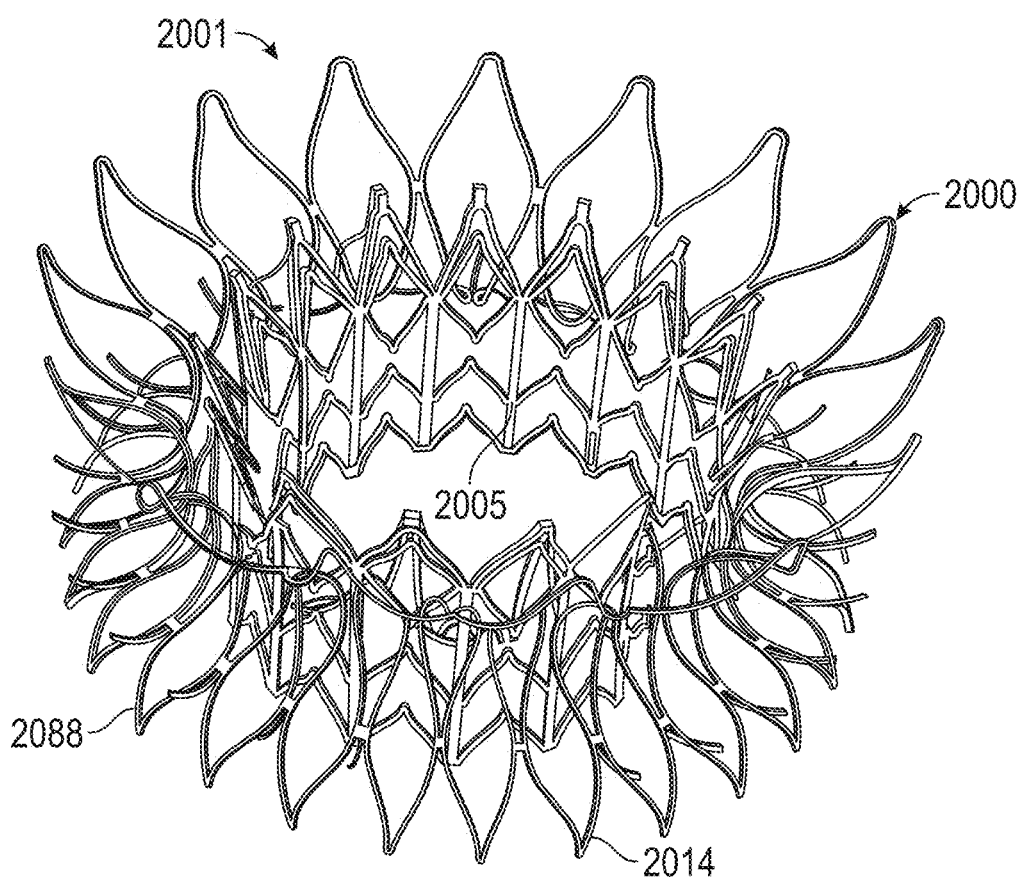
Figure 20F:
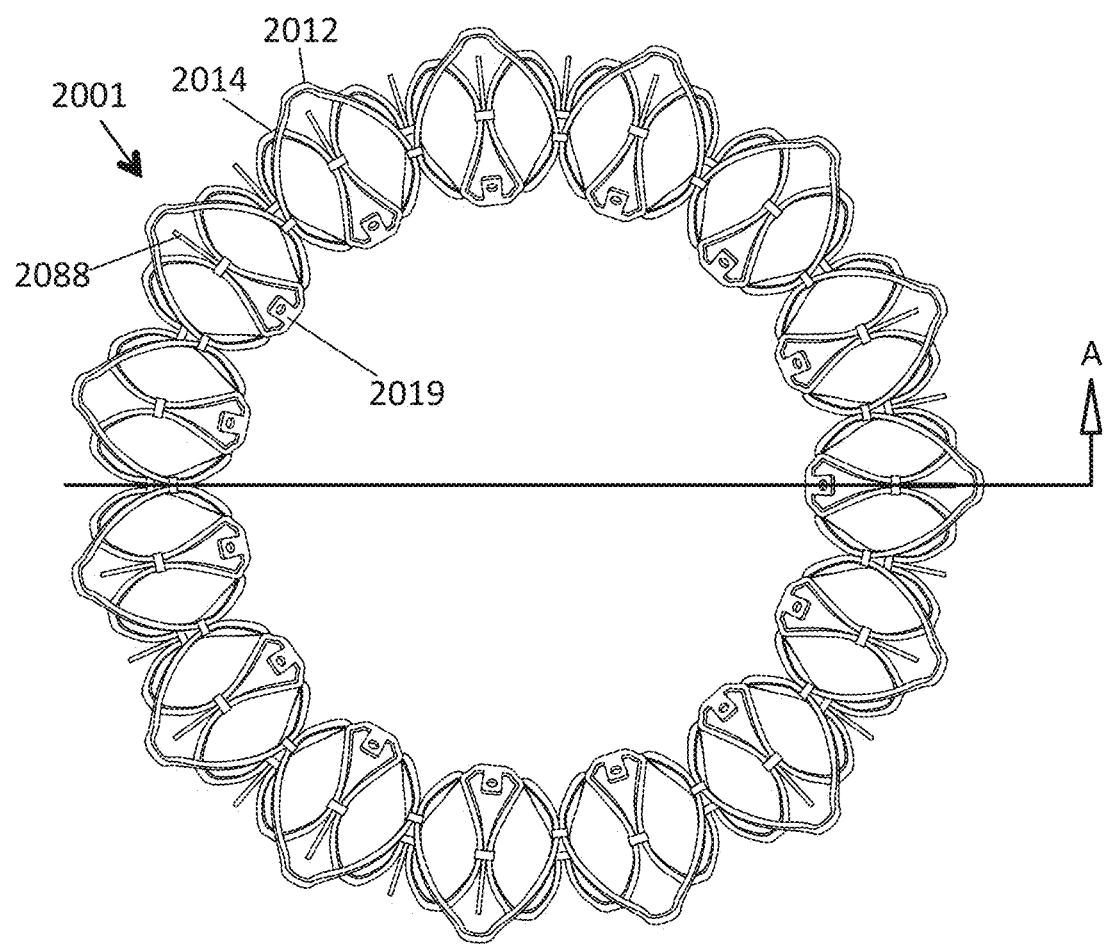
Figure 20K:
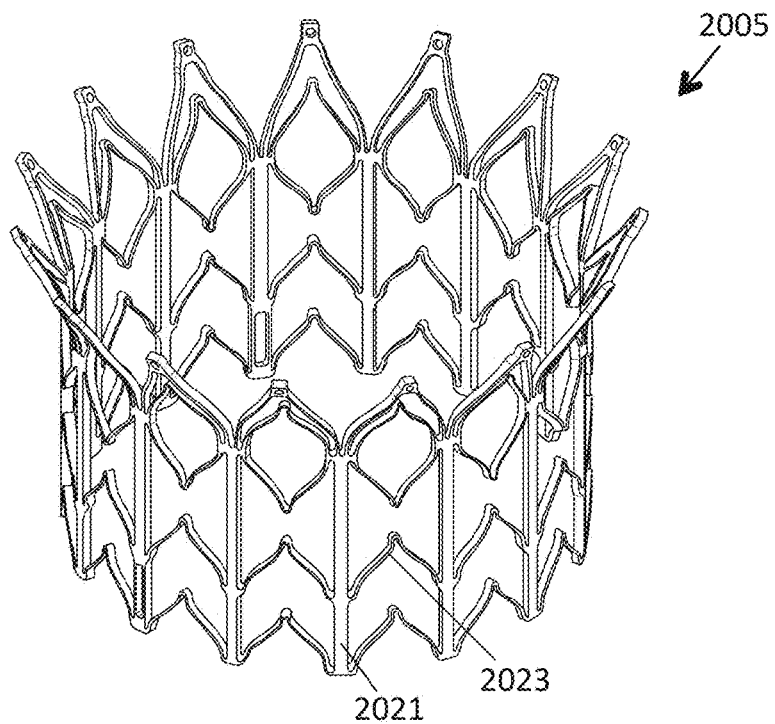
FIG. 20K shows the expanded strut frame.
Figure 20L:
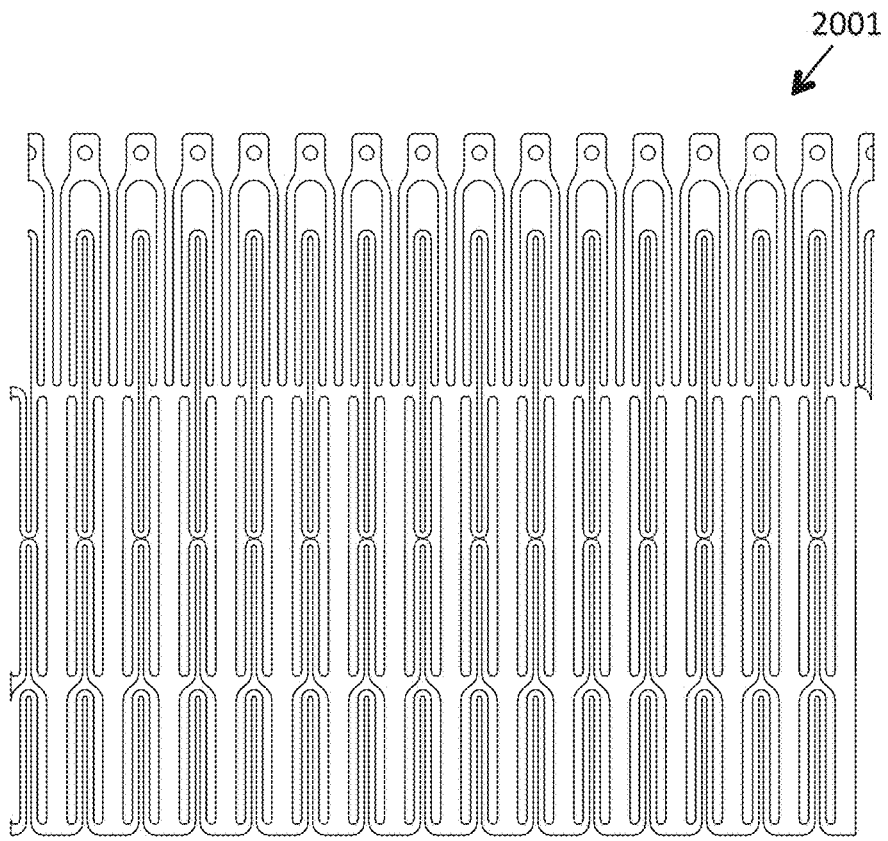
FIG. 20L is a 2D view of the (unexpanded) strut frame.
Figure 20M:
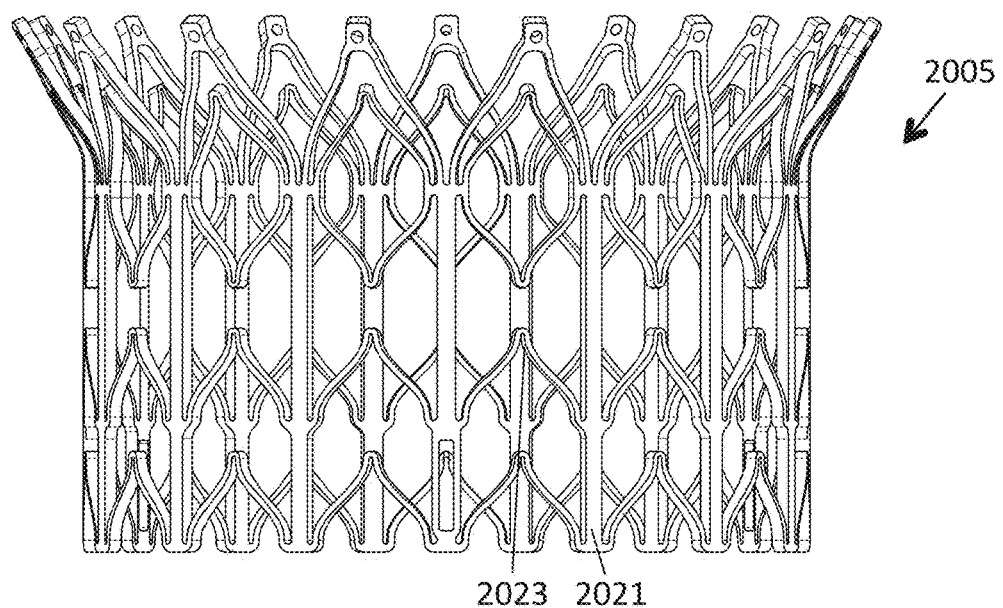
FIG. 20M is a side view of the strut frame.
Figure 20N:
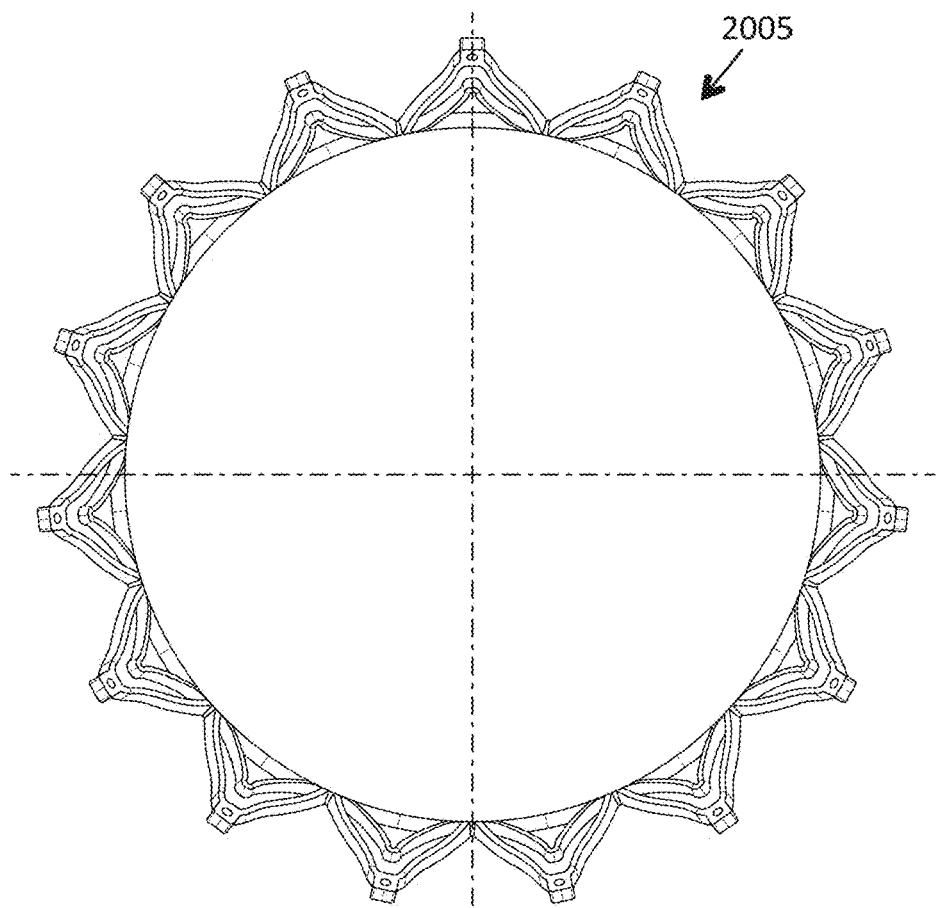
FIG. 20N is a top (atrial) view of the strut frame.
Figure 20P:
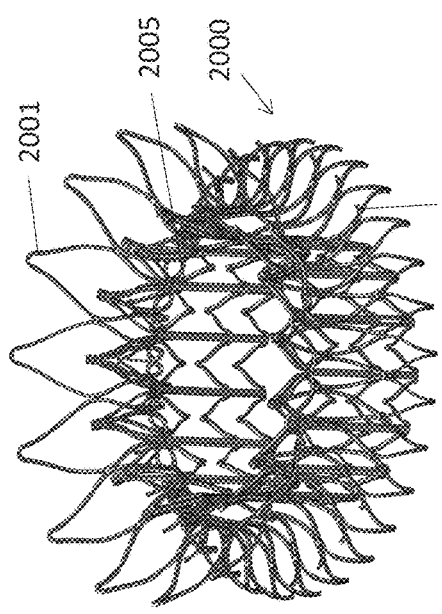
Figure 20O:
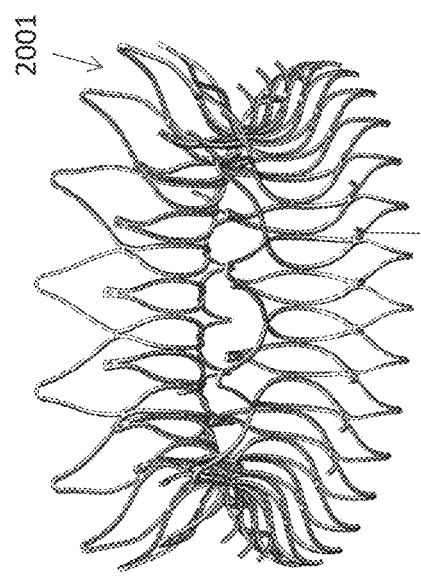
FIG. 20O is another view of the expanded anchor assembly.
Figure 20Q:
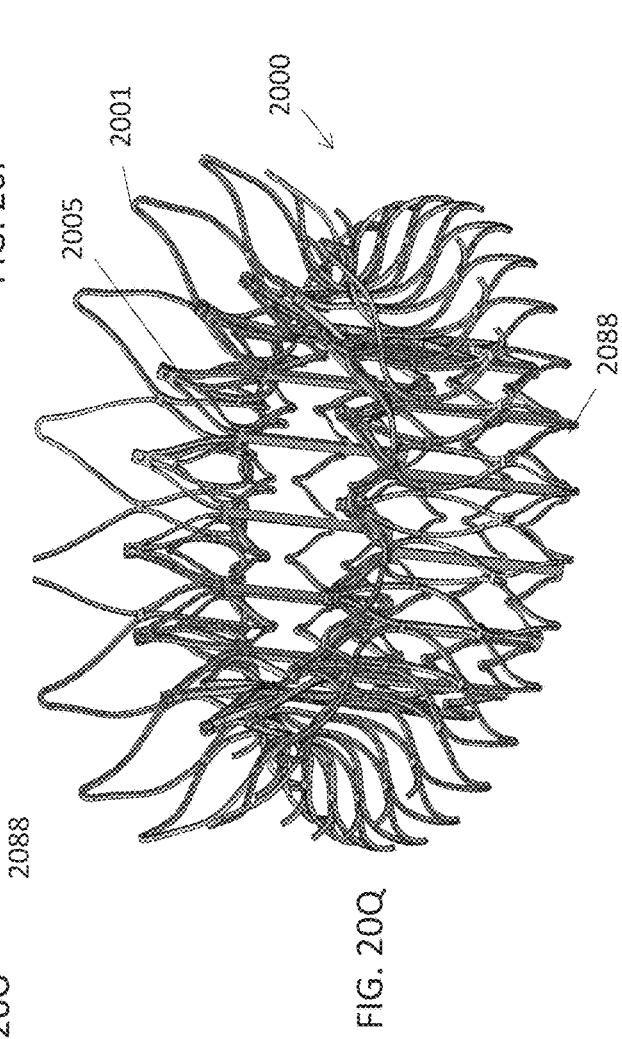

FIGS. 20A-20Q show another exemplary valve prosthesis 2000 including a valve assembly 2001 and a strut frame 2005. Prosthesis 2000 is similar to valve prosthesis 800 except that that the tips 2014 of the ventricular anchor 2004, after flaring radially outwards at the angle of 5-15° relative to the horizontal plane 2020, can curve away from the horizontal axis 2020 to point substantially in the axial (ventricular) direction, such as at an angle of 60-70°, such as 67° relative to the horizontal plane 2020. The curvatures of the two portions can be between 2 mm and 8 mm, respectively. Similarly, the atrial anchor 2002 can extend at an initial angle of 20°-30°, such as approximately 26°, relative to the horizontal plane 2020 through the central portion 2003. The tips 2012 of the atrial cells can then curve away from the axis 2020 to point more in the axial (atrial) direction, such as at an angle of 60-70°, such as 67° relative to the horizontal plane 2020. The curvatures of the two portions can be between 2 mm and 8 mm, respectively. Further, the atrial apexes 2019 with the rivet holes therein can extend at an angle of approximately 50-70°, such as 60° relative to the axis 2020, to meet and affix to the strut frame 2050. Similarly, the atrial tips 2029 of the strut frame 2005 can flare out at approximately 70°-80° relative to the horizontal axis 2020 so as to substantially conform to the flare of the atrial apexes 2019. There can be 30 atrial cells along a single circumference and only 15 ventricular cells.

Further, as is best shown in FIGS. 20K-20N, the strut frame 2005 is different from the strut frame 805 in that the strut frame 2205 does not include flexible members (e.g., zig-zag features) in the flare at the atrial end of the strut frame 2005. Rather, the connecting member on the anchoring structure can be made more compliant. Like strut frame 205, the strut frame 2005 includes a plurality of struts 2021 and v-shaped member 2023 so as to be non-foreshortening. In strut frame 2005, however, there are five v-shaped members 2023 extending between each pair of struts 2021 rather than four. The extra v-shaped member 2023 is positioned proximate to the atrial-most v-shaped member 2023 and extends from the struts 2023 in the atrial direction. The extra v-shaped member can advantageously add circumferential strength to the strut frame 2005. The strut frame 2005 can further include one or more slots 2733 in the struts 2021 to allow for attachment of leaflets, as described below.

The anchor assembly 2001 also includes barbs or hooks 2088 that, similar to hooks 888, are positioned between the ventricular tips 2014 in the valleys and are curved backwards towards the atrial end. Further, in some embodiments, and as shown at FIGS. 20O-20Q, the hooks 2088 can be positioned between every ventricular cell 2011 (e.g., in the valleys) except those valleys closest to the commissure attachment points. At those points, one or more (such as three) of the hooks 2088 can be removed so as to prevent interference with the commissures and/or leaflets when the prosthesis is in the collapsed configuration.

Figure 28:
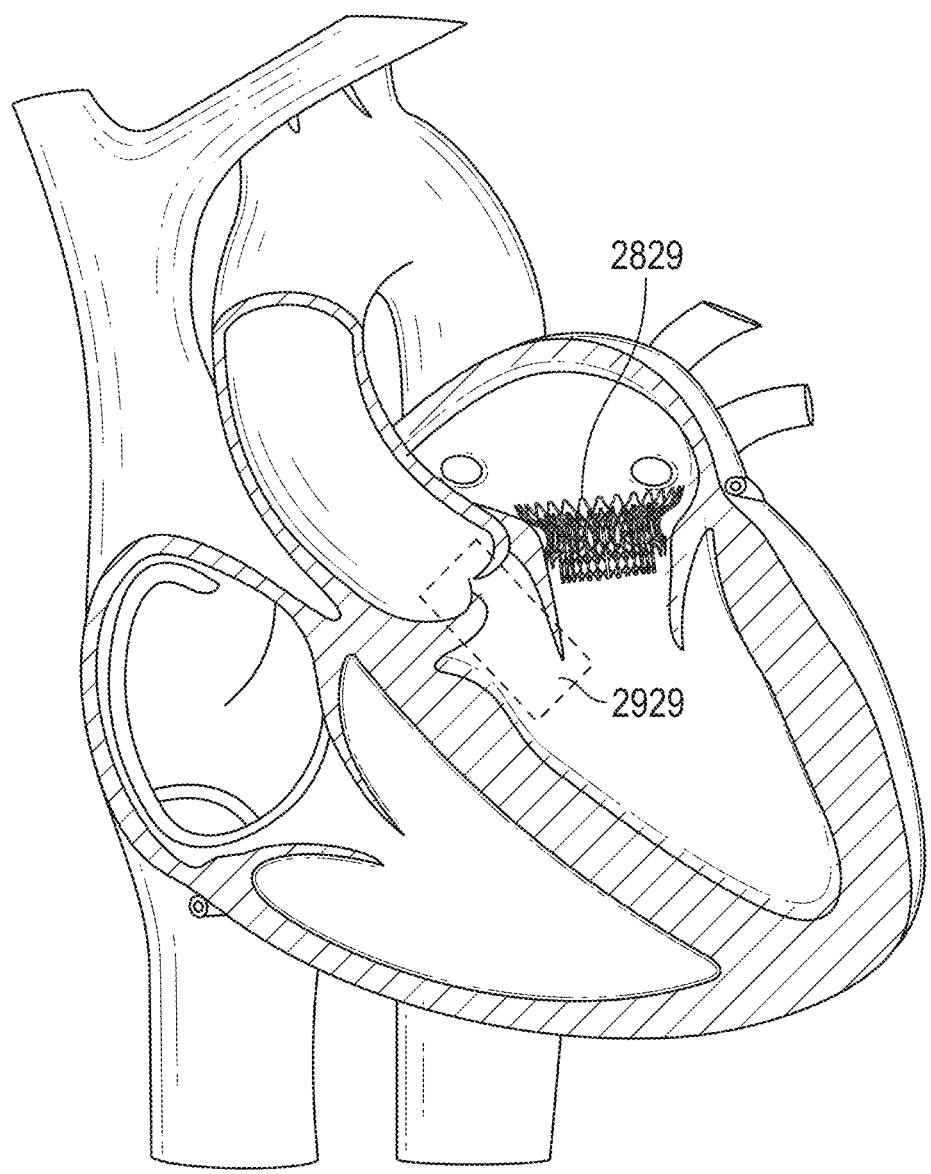
FIG. 28 shows placement of an exemplary valve prosthesis in the native mitral valve orifice.

In some embodiments, such as for the anchor assembly 2000, the atrial anchor 2002 can have a larger diameter than the ventricular anchor 2004. Having a larger atrial anchor 2002 than a ventricular anchor 2004 allows the anchors 2002, 2004 to grip tissue while preventing the ventricular anchor 2004 from impeding flow to the aortic valve. That is, as shown in FIG. 28, if the ventricular anchor is too large, then the Left Ventricular Outflow Tract (LVOT) 2828 may be obstructed and restrict flow through the adjacent aortic valve 2829. In some embodiments, for example, the atrial anchor 2002 can have a diameter that is 3-10% larger than the diameter of the ventricular anchor 2004. The ventricular anchor 2004 can thus be less than 55 mm, such as less than or equal to 54 mm, such as less than or equal to 52 mm.

Figure 24A:
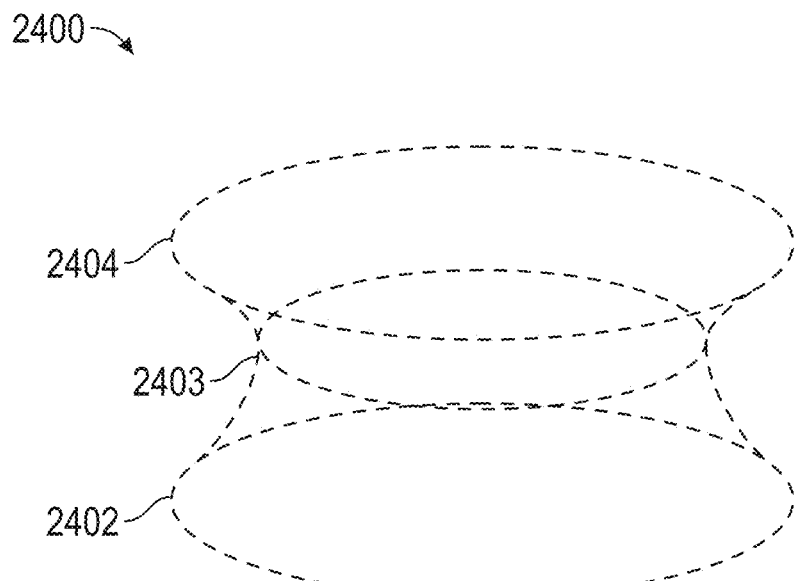
FIGS. 24A-24C show an exemplary mitral valve prosthesis with a first set of dimensions.
Figure 24B:
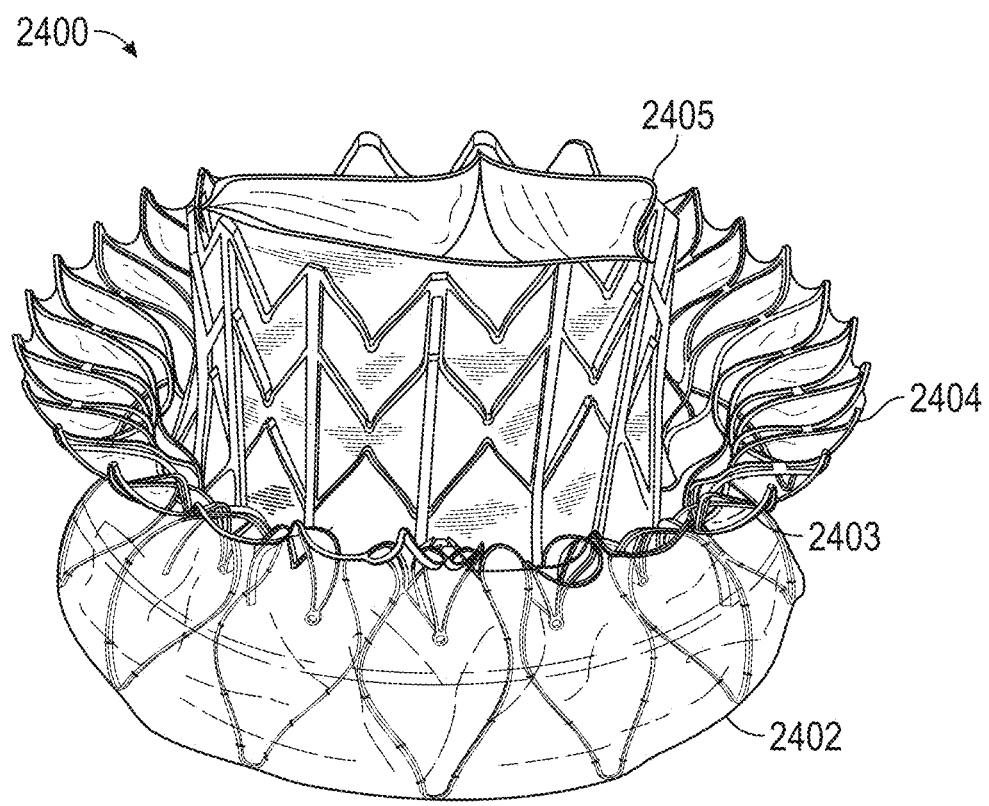
Figure 24C:
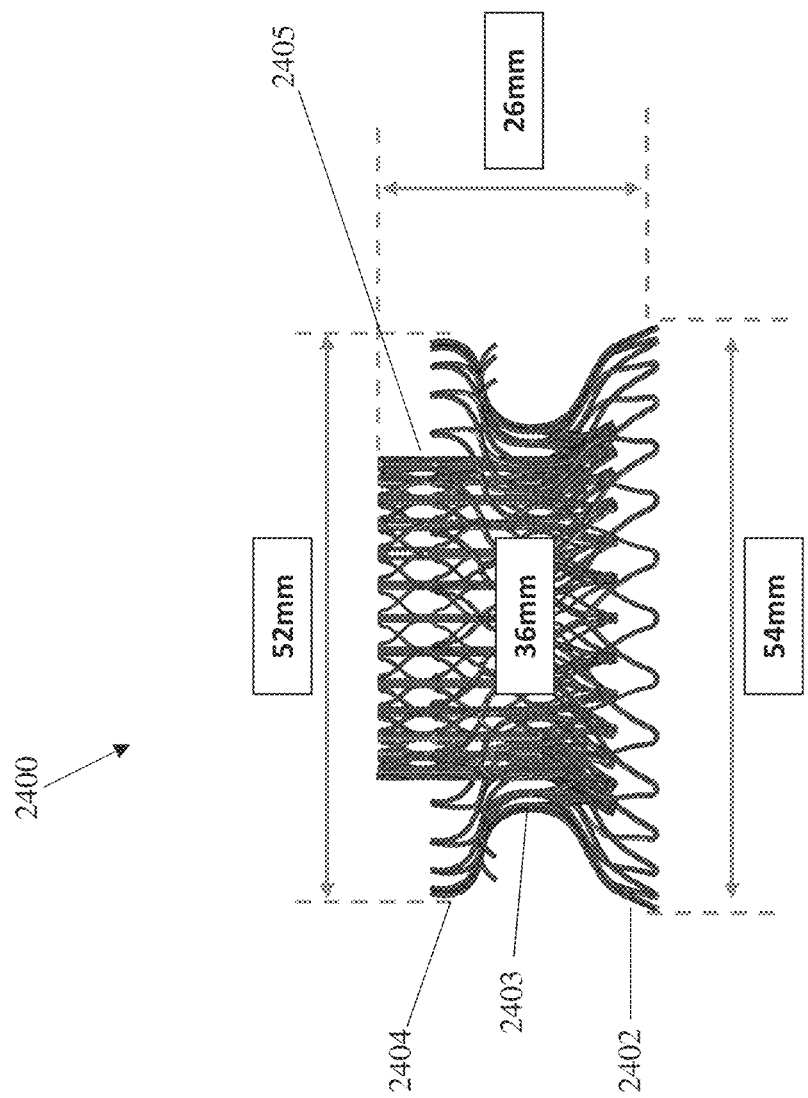
Figure 25A:
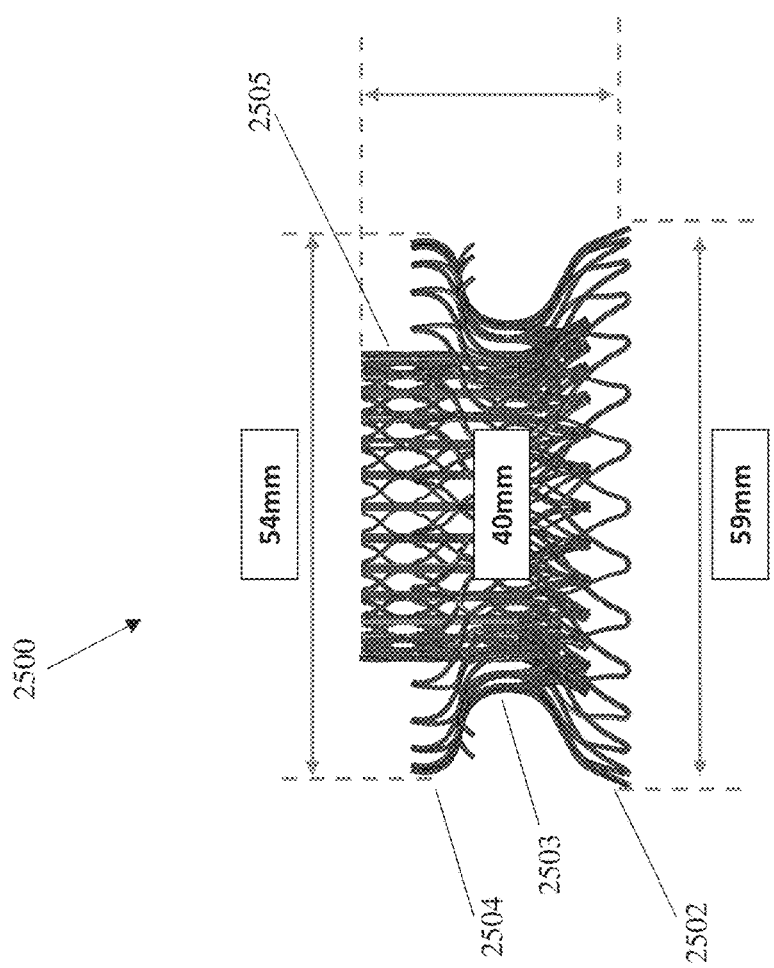
FIGS. 25A-25C show an exemplary mitral valve prosthesis with a second set of dimensions.
Figure 25B:
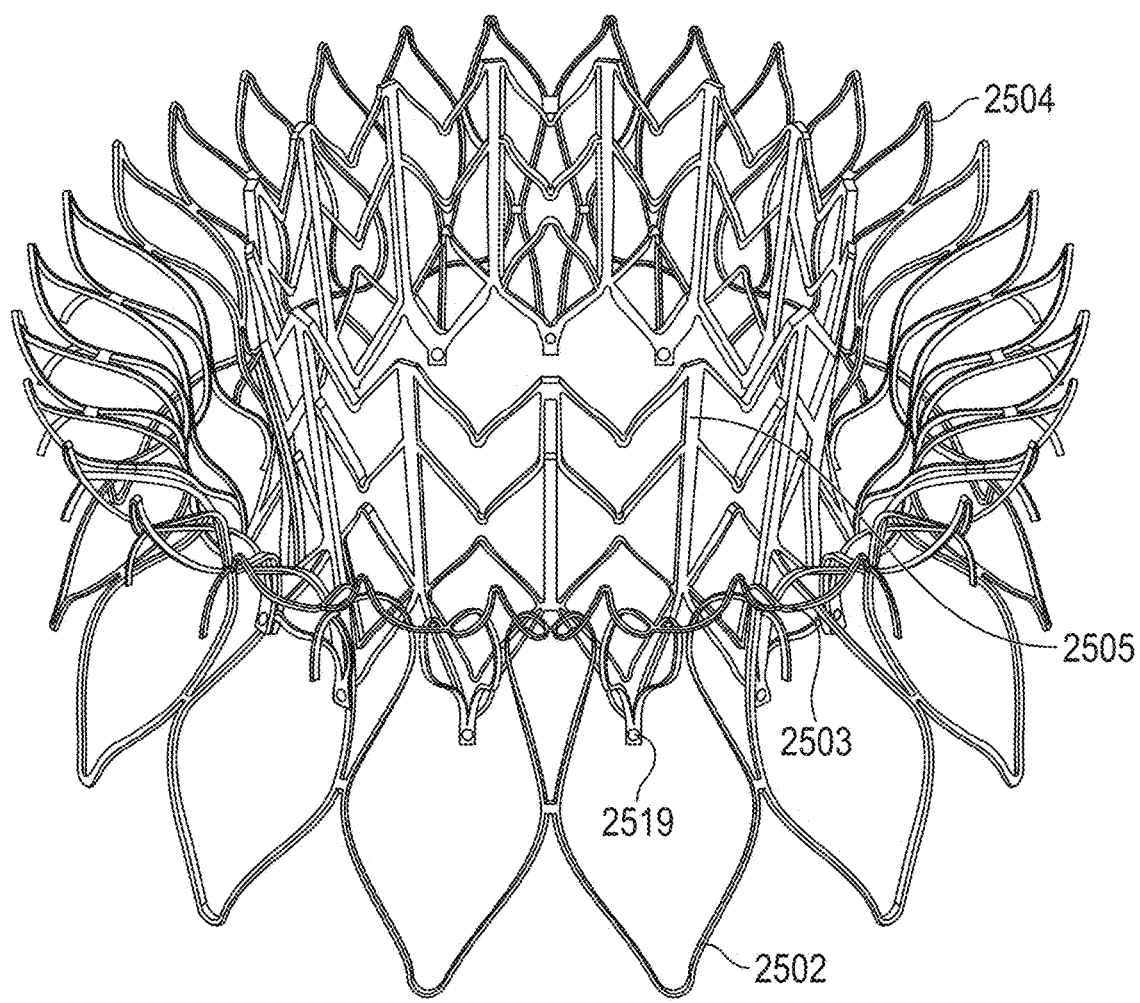
Figure 25C:
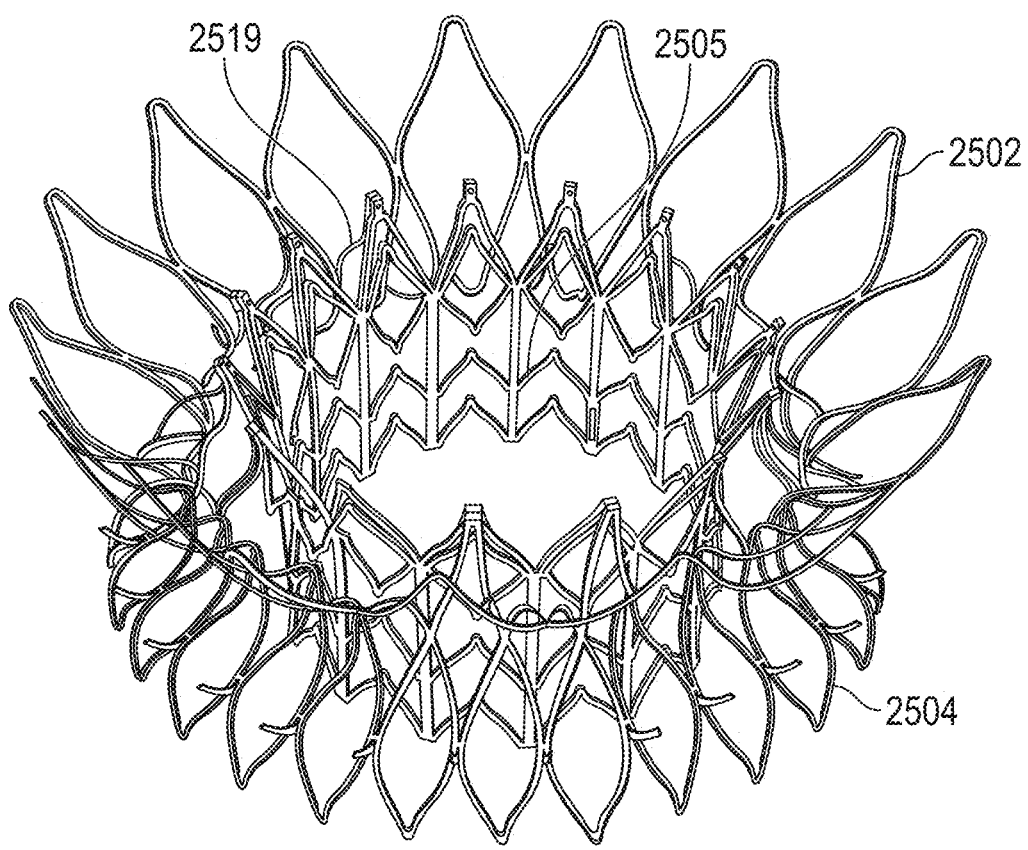

In some embodiments, the prostheses described herein can be made in a plurality of different sizes so as to fit within a range of native valve orifice sizes. For example, referring to FIGS. 24A-24C, in some embodiments, a valve prosthesis 2400 can have an atrial anchor 2402 with an outer diameter of 54 mm, a ventricular anchor 2404 with an outer diameter of 52 mm, and a central portion 2403 with an outer diameter of 36 mm. Further, the strut frame 2405 can have an inner diameter of 27 mm-30 mm, such as approximately 29 mm. A total height of the prosthesis 2400 can be, for example, 22-28 mm, such as 26 mm. In contrast, the valve prosthesis 2500 of FIGS. 25A-25C can have a larger diameter to fit within a larger native valve orifice. For example, the atrial anchor 2502 can have an outer diameter of 59 mm, the ventricular anchor can have an outer diameter of 54 mm, and the central portion 2503 can have an outer diameter of 40 mm. The strut frame 2505, like the strut frame 2405, can have an inner diameter of 27 mm-30 mm, such as 29 mm. To compensate for the increased diameter of the valve assembly 2501 relative to the strut frame 2505, the disconnected atrial apexes 2519 can be pulled further radially inwards (for example, the disconnected atrial apexes 2519 can be pulled downwards in an s-shape to reach further inwards). A total length of the expanded valve 2500 can be 28-29 mm. Further, in order to maintain low packing strain, the sheathed or packed length of the valve 2500 can be longer than the packed length of the valve 2400. For example, the packed length of valve 2400 can be 32 mm-35 mm while the packed length of valve 2500 can be 34 mm-37 mm.

Anchor assemblies 101-401, 801, 2001, 2401, and 2501 all foreshorten upon expansion (due to their cellular design). For example, the anchor assemblies can foreshorten by 20%-30%. In contrast, the corresponding strut frames 105-405, 805, 2005, 2405, and 2505 maintain substantially the same axial length.

In some embodiments, the prosthesis can be designed such that the entire prosthesis does not foreshorten during expansion. Having the prosthesis not foreshorten advantageously allows the packed length to be much shorter, such as less than 35 mm, such than 30 mm, or less than 25 mm.

Figure 5A:
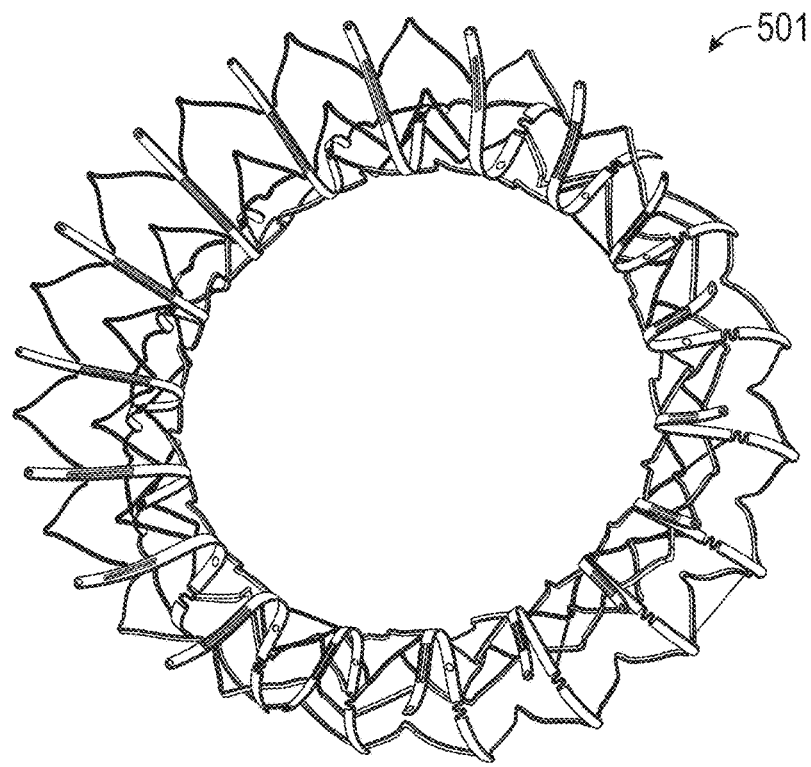
FIGS. 5A-5C show an exemplary nonforeshortening anchor assembly in the expanded configuration.
Figure 5B:
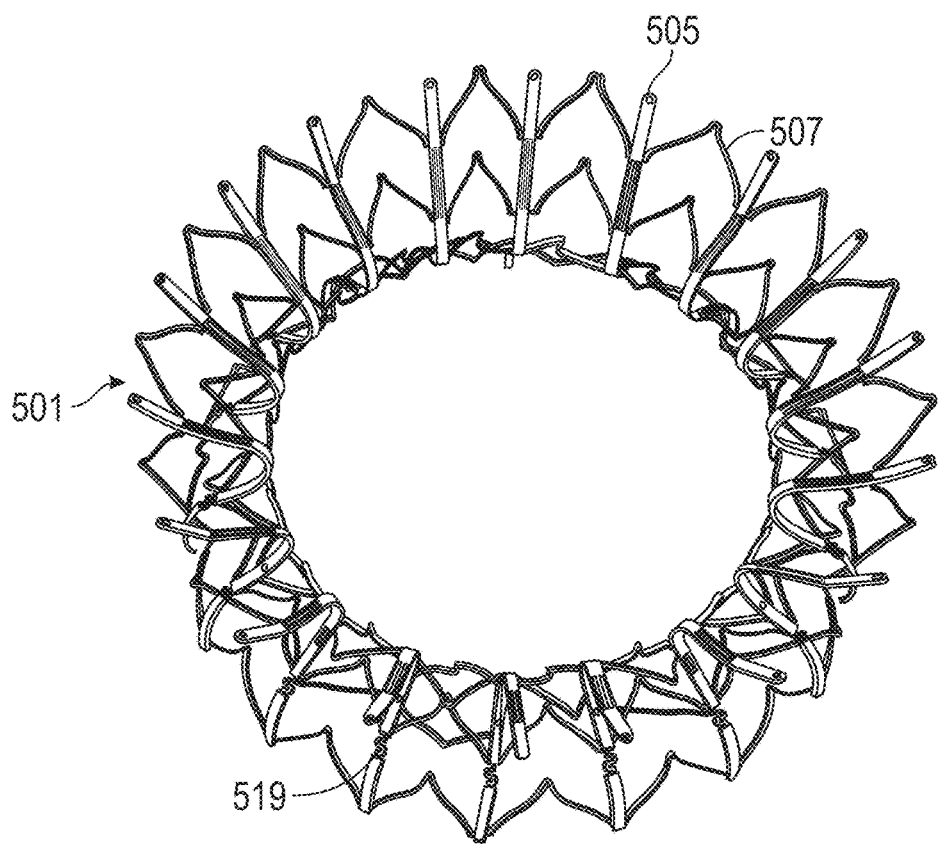
Figure 5C:
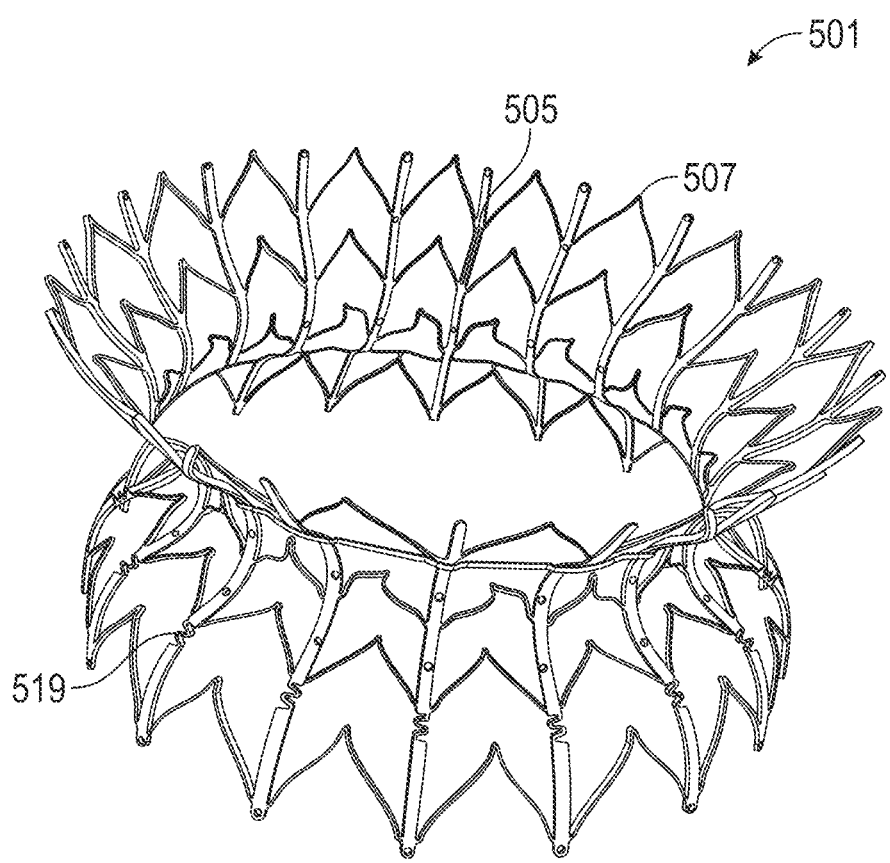

For example, FIGS. 5A-5C show an anchor assembly 501 that includes a plurality of struts 505 and circumferential v-shaped connectors 507 that do not substantially foreshorten upon expansion. The anchor assembly 501 forms a primarily hour-glass shape in the expanded configuration. Further, the atrial end includes flexible members 519 (e.g., zig-zag members) to aid in conforming to the native orifice.

Figure 6A:
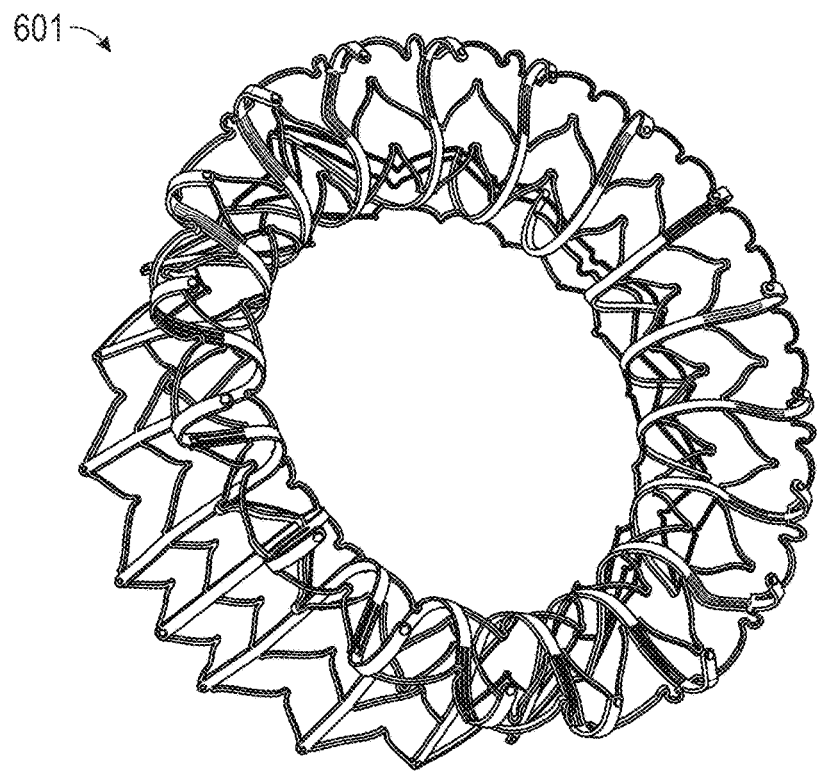
FIGS. 6A-6C show another exemplary nonforeshortening anchor assembly in the expanded configuration.
Figure 6B:
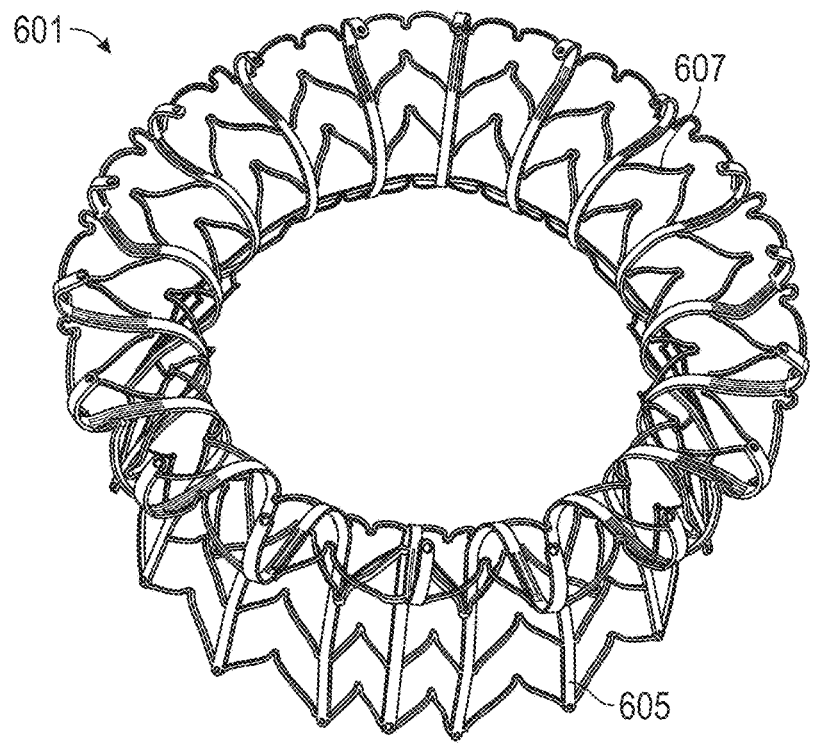
Figure 6C:
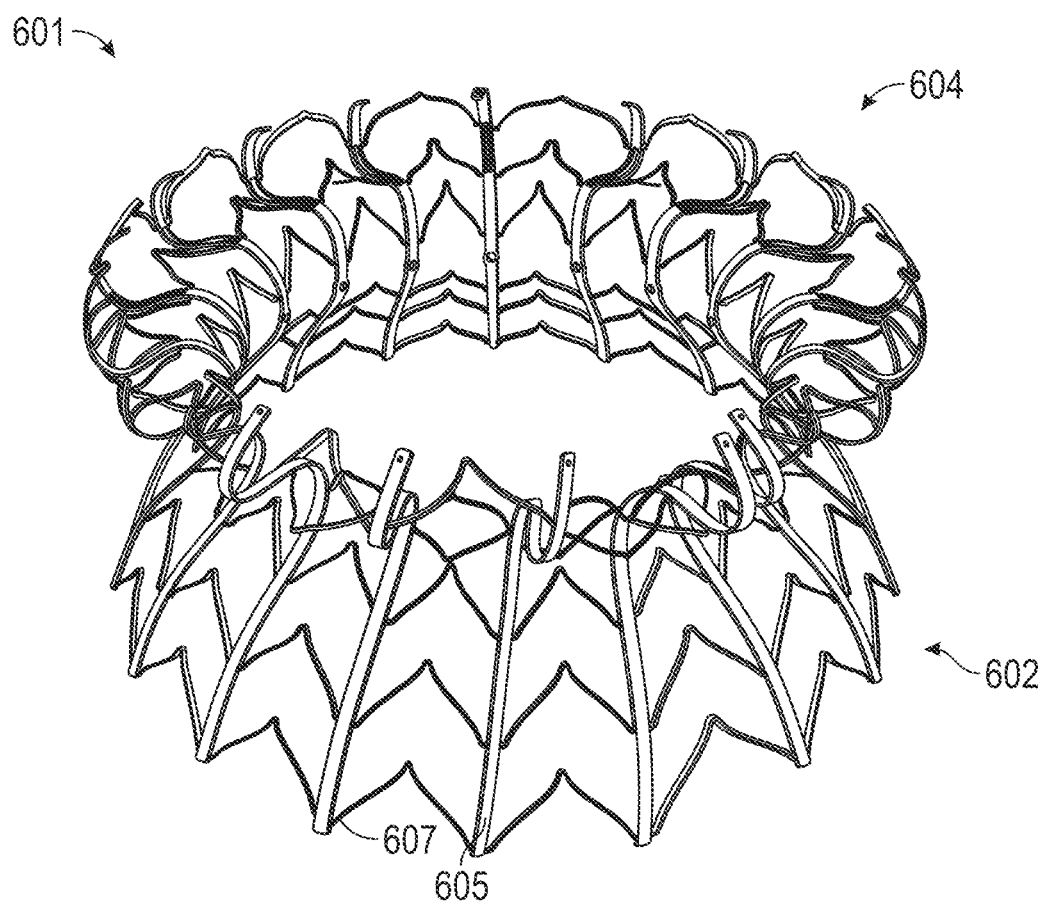

FIGS. 6A-6C show another exemplary nonforeshortening anchor assembly 601 with a plurality of struts 605 and circumferential v-shaped connectors 607. In this embodiment, the ventricular anchor 604 is curled inwards at the tips to minimize interaction with the native ventricular anatomy.

FIGS. 9A-9D show another exemplary nonforeshortening anchor assembly 901 with a plurality of struts 905 and circumferential v-shaped connectors 907. In this embodiment, there are 5 v-shaped connectors 907 extending between each set of struts 905. The ventricular ends of the ventricular anchor 904, like ventricular anchor 604, curl in at the tips to minimize interaction with the native anatomy. Further, the struts 905 each include a flexible portion 929 (e.g., zig-zag or serpentine section) that extends from the atrial tips to the central portion 903. The flexible portions 929 aid in conforming the atrial anchor 902 to the native orifice. In this embodiment, the strut frame (which can be any strut frame described herein) can be configured to attached mid-way along the atrial anchor 902, such as rivet location 939. Advantageously, by attaching the strut frame at the atrial anchor (i.e., rather than the ventricular anchor), the strut frame can be less prone to distortion that can occur when the ventricular anchor is expanded during delivery.

Various hook or barb mechanisms can be used with any of the valves described herein. For example, the barb or hook can be riveted to the anchor assembly, can be laser cut from the assembly, and/can be formed as part of a v-shaped feature of the anchor assembly. The hook or barb mechanisms can be designed such that they point radially outwards during deployment (i.e., not into the tissue) and do not engage with tissue until fully released, thereby preventing interference with the deployment. This can be achieved, for example, by using a hook having the proper radius of curvature to thickness ratio.

In some embodiments, the hooks can be on the ventricular most tips of the ventricular anchor, as shown in FIGS. 1A-1C. In other embodiments, the hooks can be in the valleys (i.e., between petals or tips, as shown in FIGS. 8A-8G and 20A-N). For example, the hooks can be placed in valleys on the ventricular anchor (e.g., from an apex of an interior diamond-shaped cell). When positioned between valleys on the ventricular anchor, the hooks can curve around and point in the atrial direction at an angle of 50°-80°, e.g., 60-65°, such as about 65° relative to the central axis of the device. This angle can advantageously allow the hooks to point in the atrial direction to dig into tissue. Further, each hook can have a ratio of radius of curvature to thickness of between 4:1 and 6:1. The radius of curvature can, for example, be between 3-4 mm, and the thickness of the hook can be between 0.8 mm and 1.6 mm. For example, in one embodiment, the radius of curvature is 3.5 mm and the thickness of the hook is between 0.8 mm and 1.6 mm.

Figure 7A:
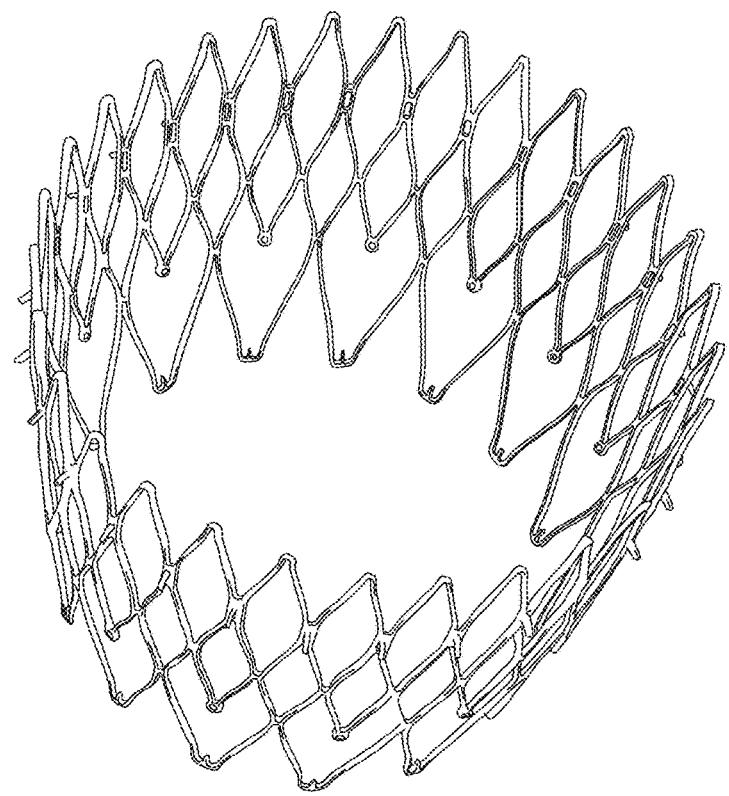
FIGS. 7A-7B show an exemplary anchor assembly before it is heat-set into an hour-glass shape.
Figure 7B:
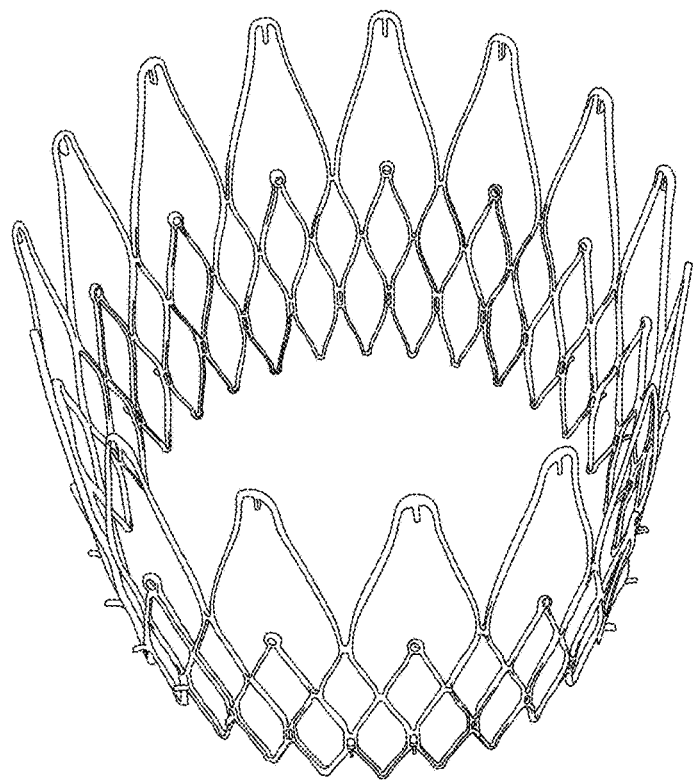
Figure 8A:
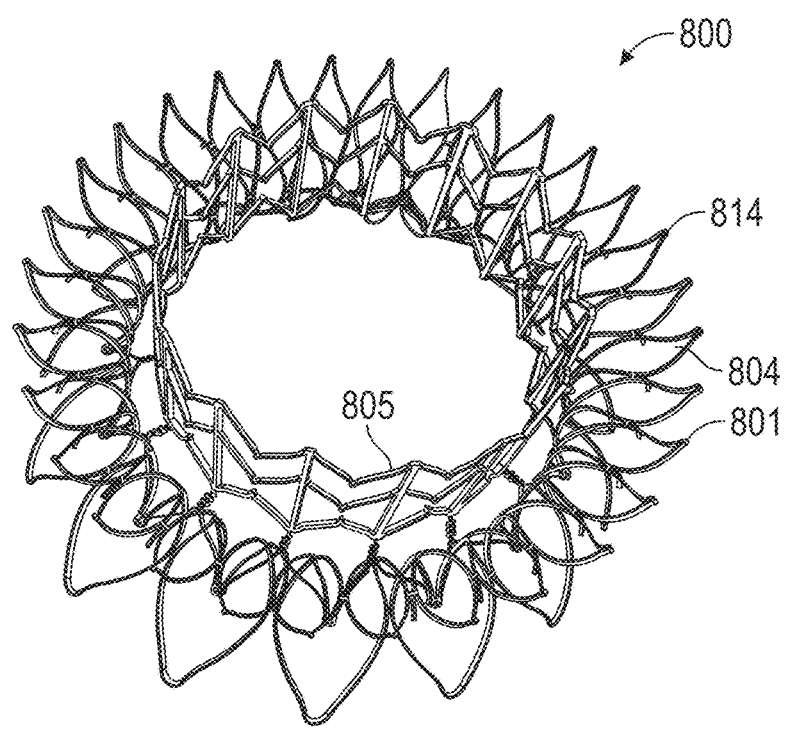
Figure 8B:
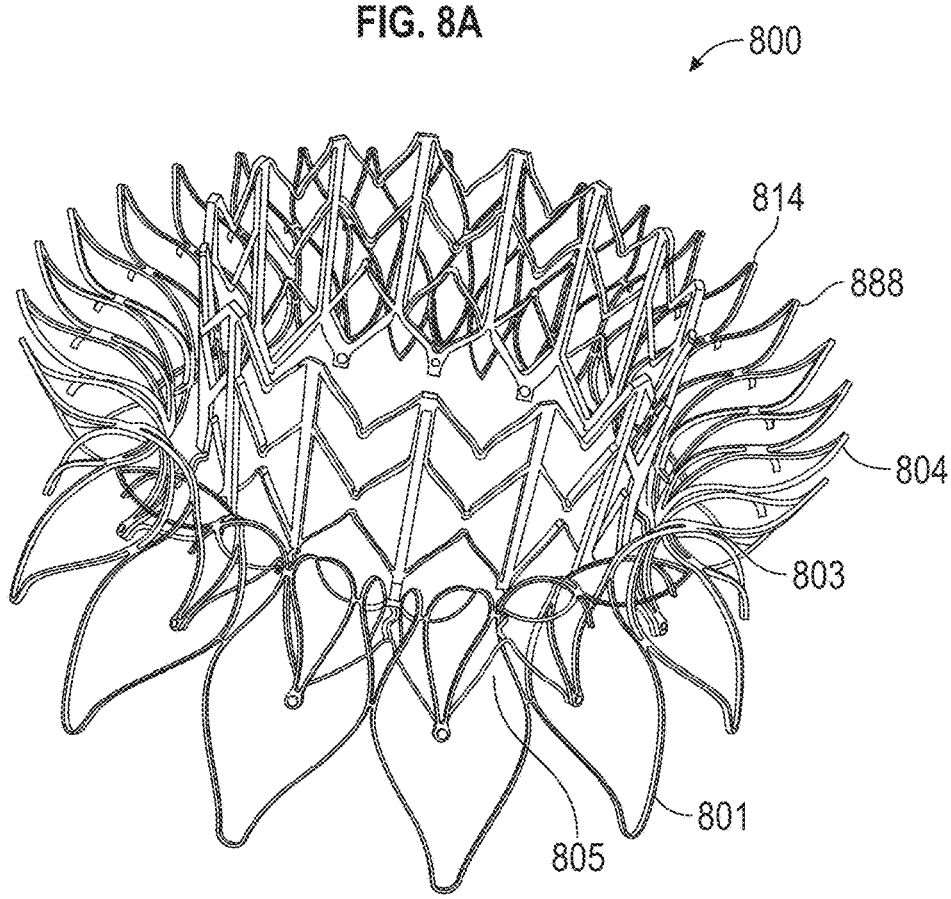
Figure 8C:
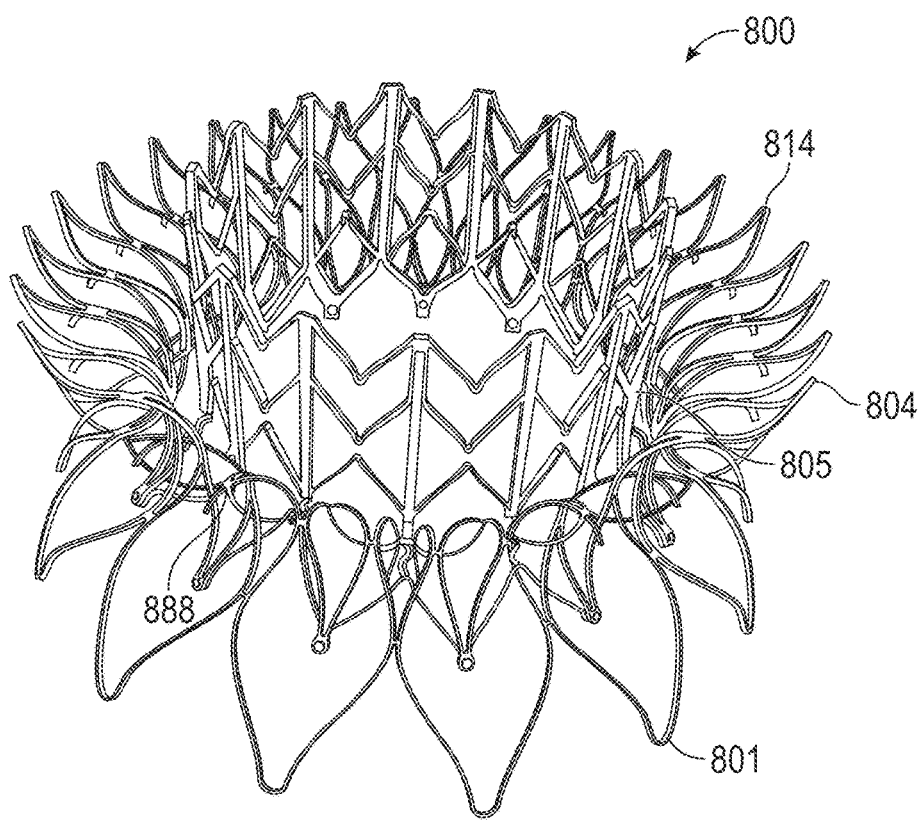
Figure 8D:
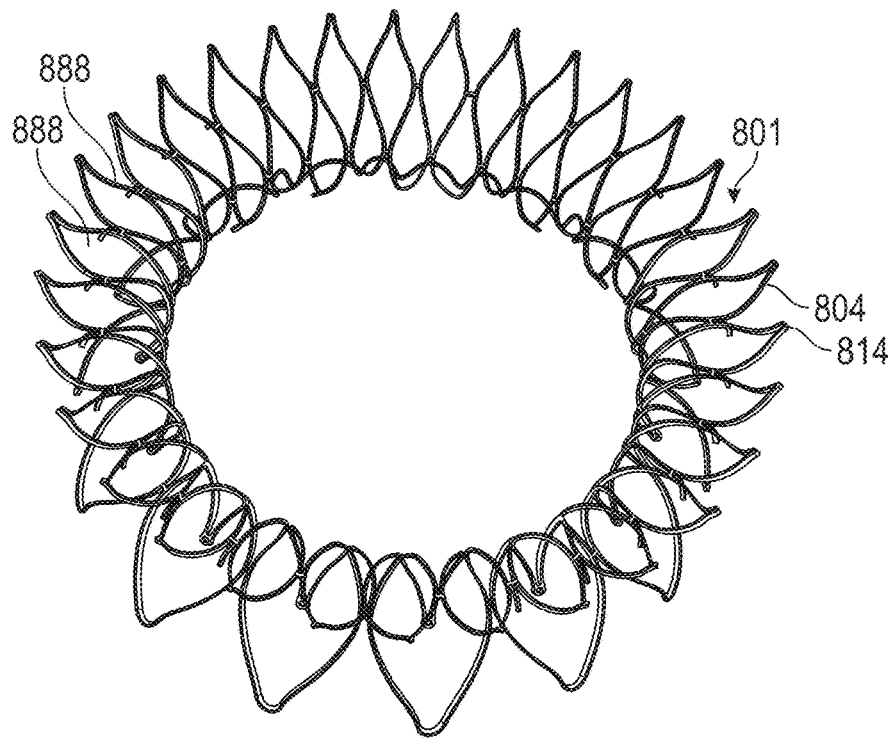
Figure 8E:
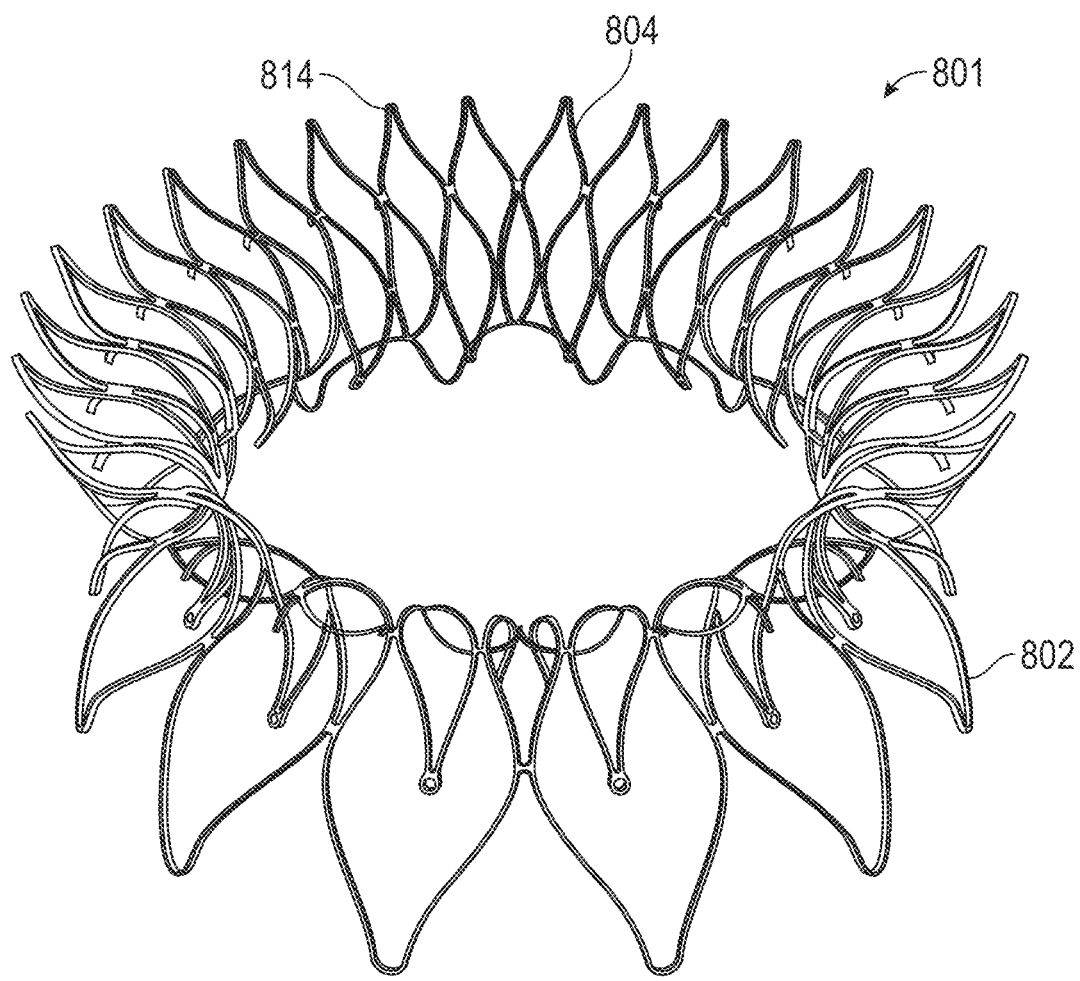
Figure 8G:
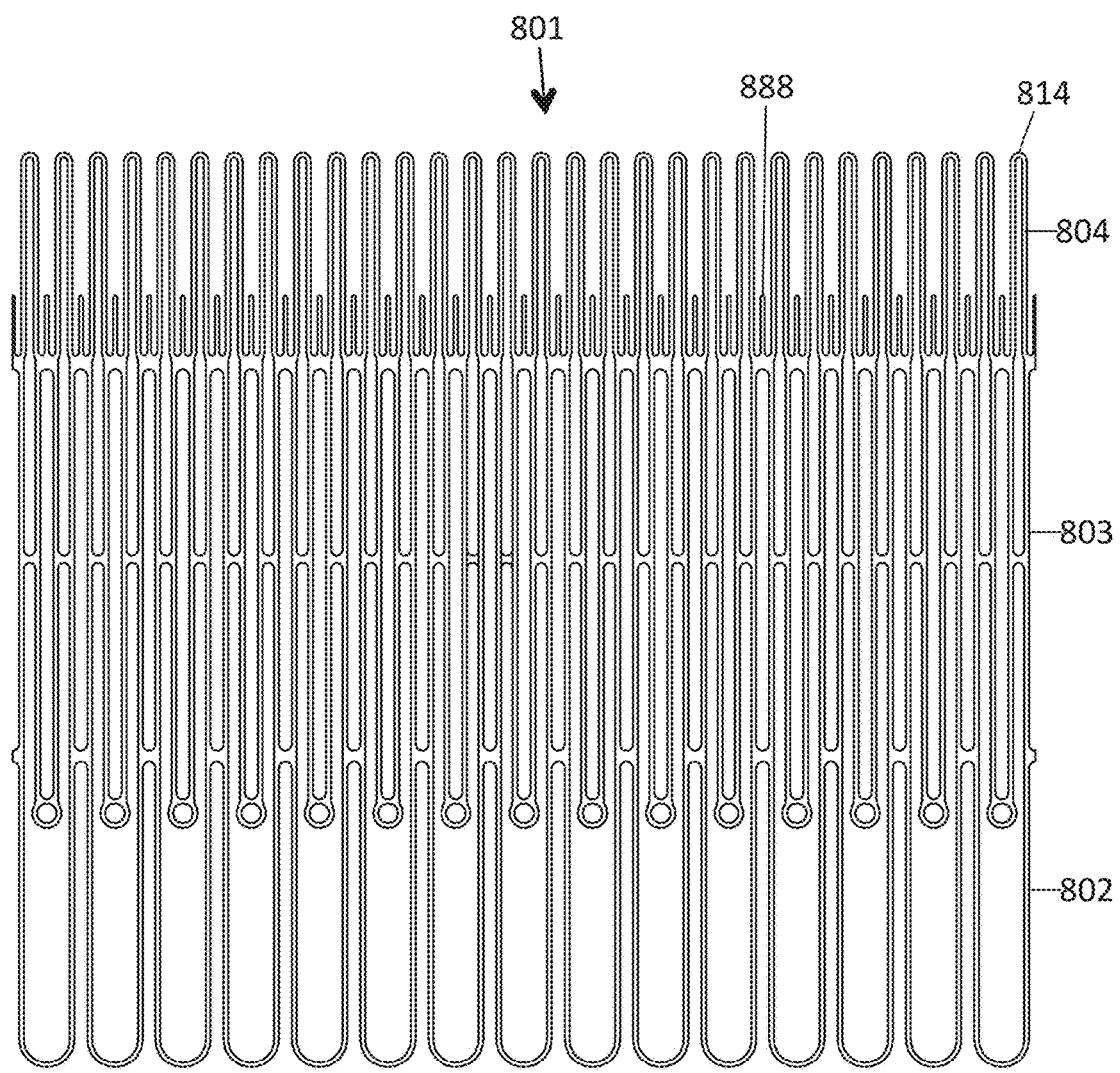
Figure 9A:
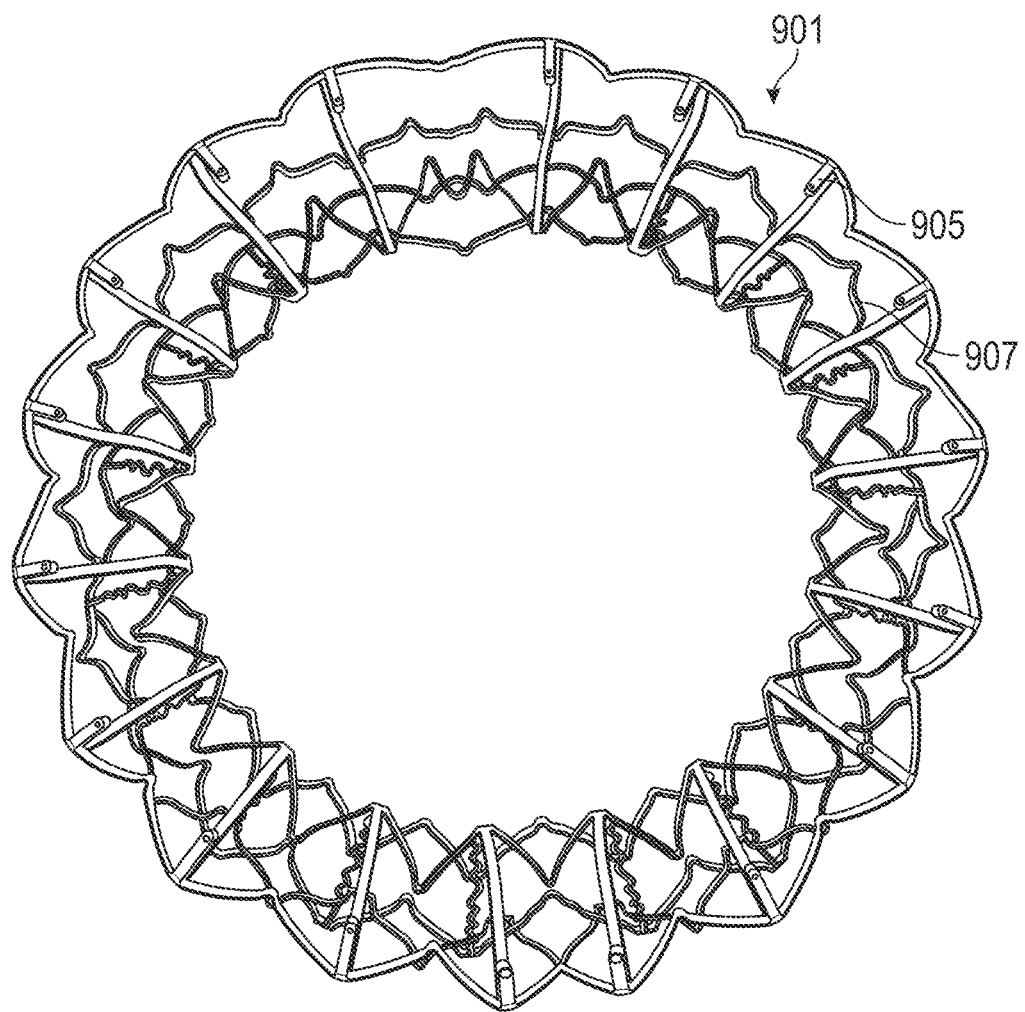
FIGS. 9A-9D show another exemplary nonforeshortening anchor assembly.
Figure 9B:
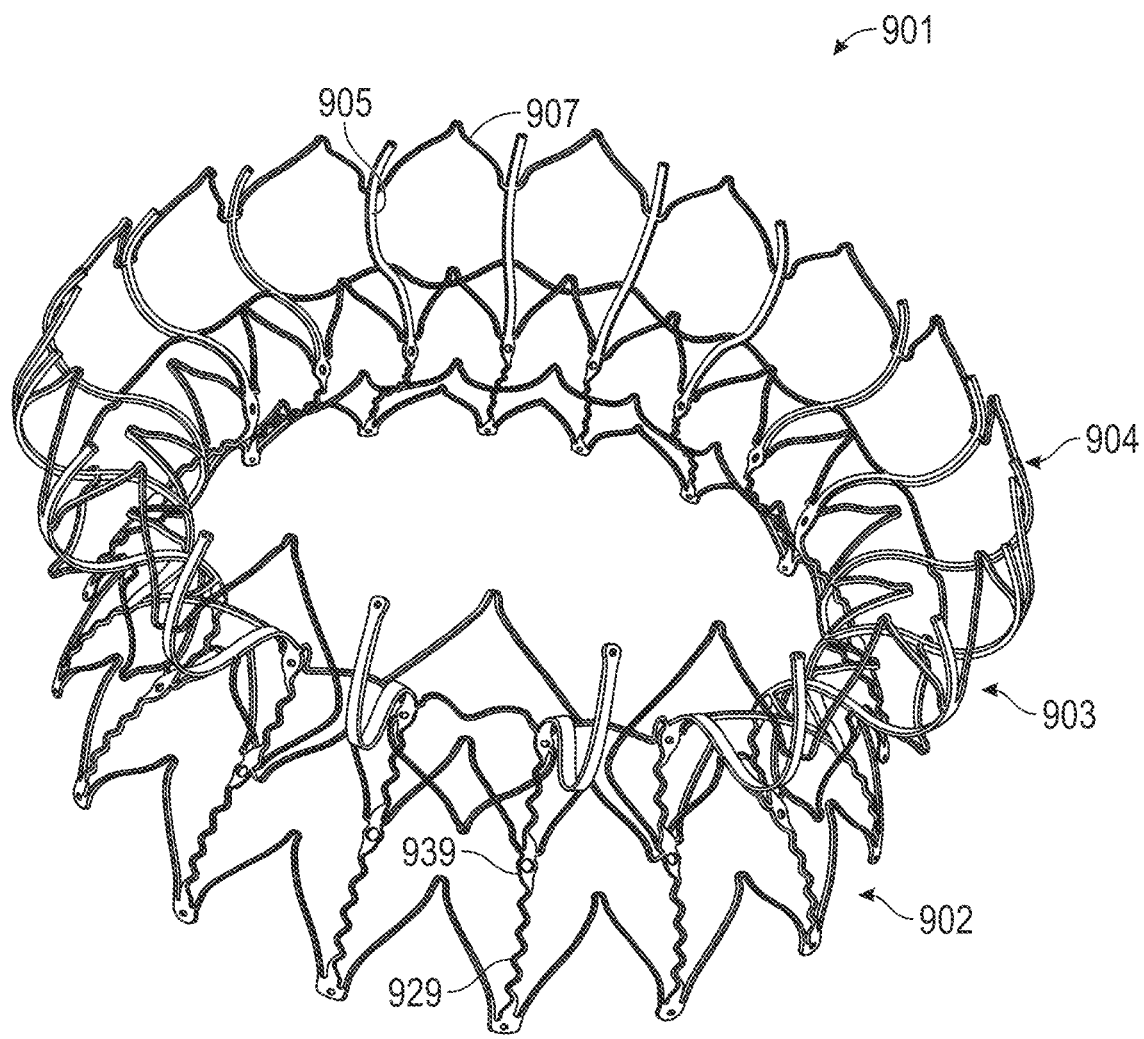
Figure 9C:
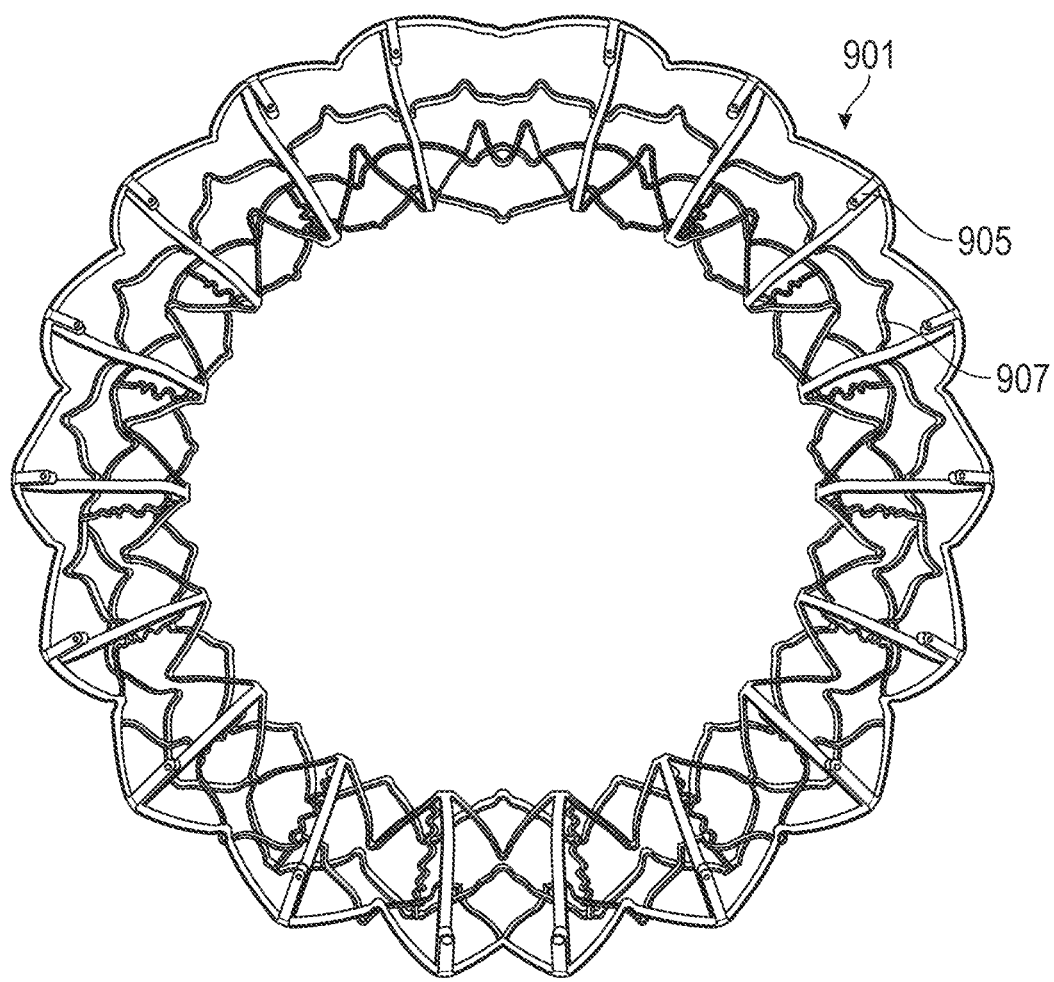
Figure 9D:
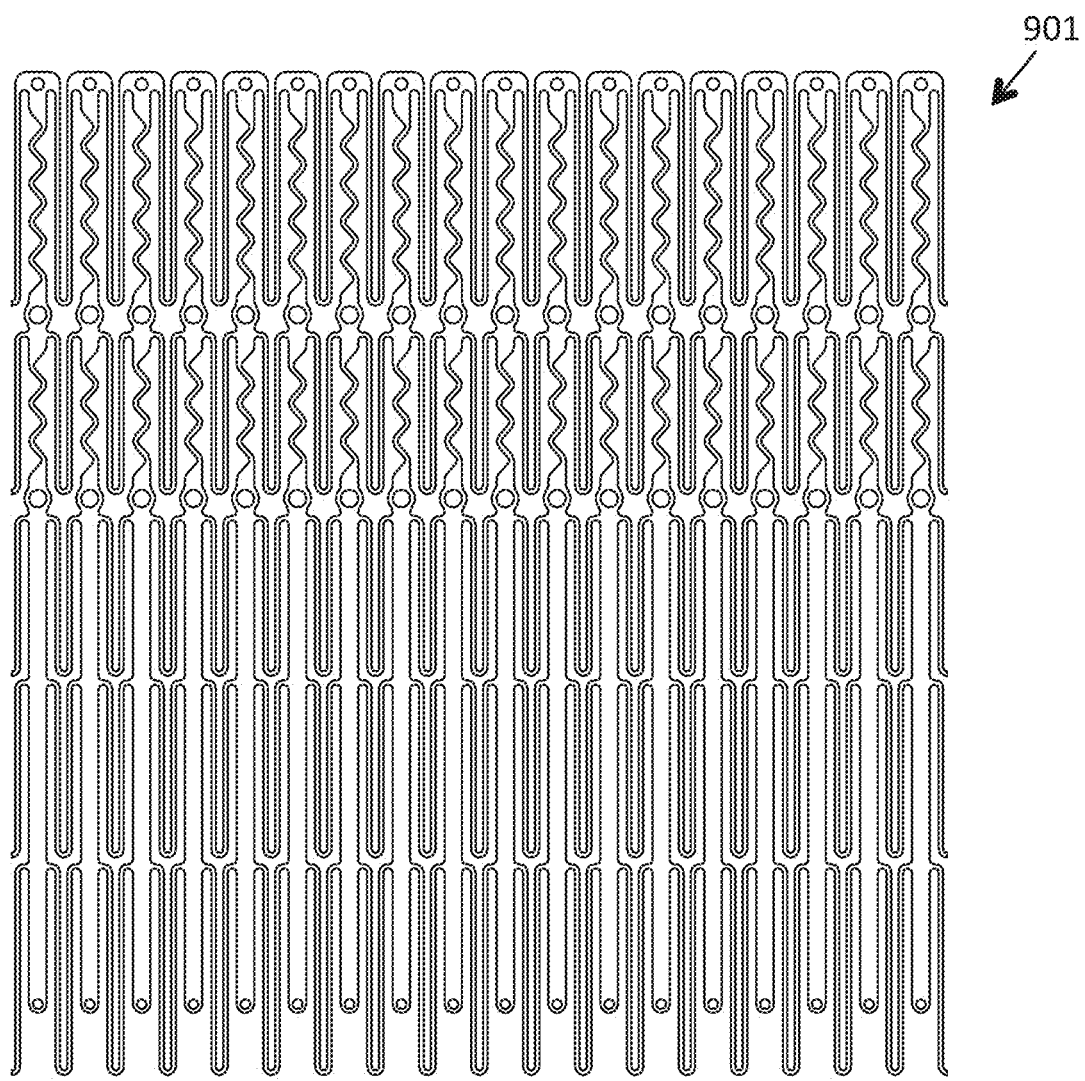

In some embodiments, the hooks can be riveted to the anchor assembly. In other embodiments (as shown in FIGS. 7A-7B), the hooks can be tabs that are flared out from the anchor assembly.

In some embodiments, as shown in FIGS. 9A-9D, a portion of the anchor assembly 901 can include a portion that is pointed radially outwards to act as a hook or barb in the tissue. For example, one set of the v-shaped circumferential members 907 can be bent to point outwards. The bent v-shaped members can be positioned, for example, on the inner diameter of the ventricular anchor 904 pointing towards the atrium.

Any of the valve prostheses described herein can include a fabric cover and/or skirt on one or more portions of the device. For example, referring to FIGS. 16A-16D (valve is shown in a holder for clarity), a covering or skirt 1616 can be sewn along the inner diameter of the atrial anchor 1616 and the flare of the strut frame 1605 and down the entire inner diameter of the strut frame 1605. This skirt 1616 can thus provide a smooth entrance for blood into the leaflets 1622. Further, the skirt 1616 can extend along the entire outer diameter of the anchoring assembly and then around the tips of the ventricular anchor 1604. In some embodiments, the skirt 1616 can be a single piece while in other embodiments, the skirt 1616 can be made of a plurality of pieces.

Figure 30:
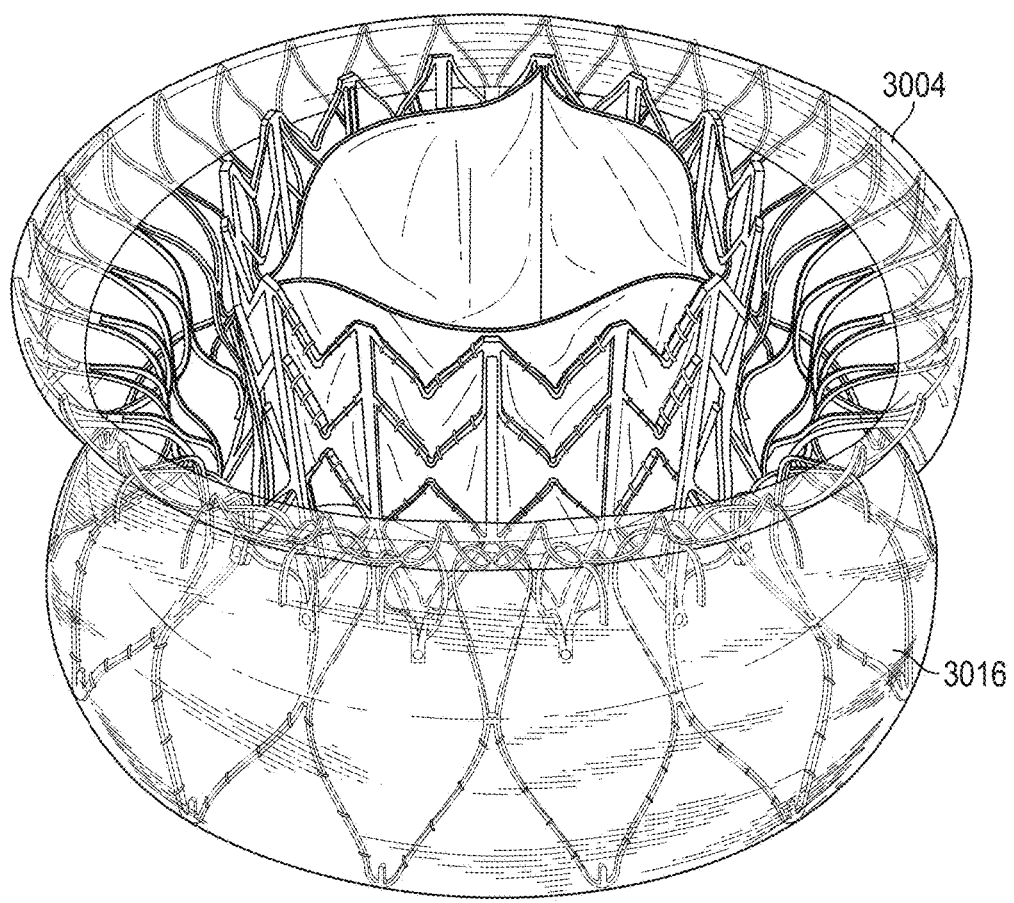
FIG. 30 shows another exemplary mitral valve prosthesis with a skirt thereon.

In some embodiments, as shown in FIG. 20A, the skirt 2016 can leave the ventricular tips of the ventricular anchor 2004 uncovered. In other embodiments, as shown in FIG. 30, the skirt 3006 can be wrapped fully around the ventricular tips of the ventricular anchor 3004.

In some embodiments, the skirt, or a portion of the skirt, can be knit in a three-dimensional shape, e.g., an hour glass shape, to help maintain a consistent seal of the skirt against the prosthesis and to help pack the skirt-covered prosthesis during delivery. For example, as shown in FIGS. 23A-23C, the skirt 2316 can be cut in an hour-glass shape and configured to cover all of the exposed sections of the valve on the atrial side (leaving only the ventricular side of the ventricular anchor and the outer diameter of the strut frame uncovered).

Figure 26:
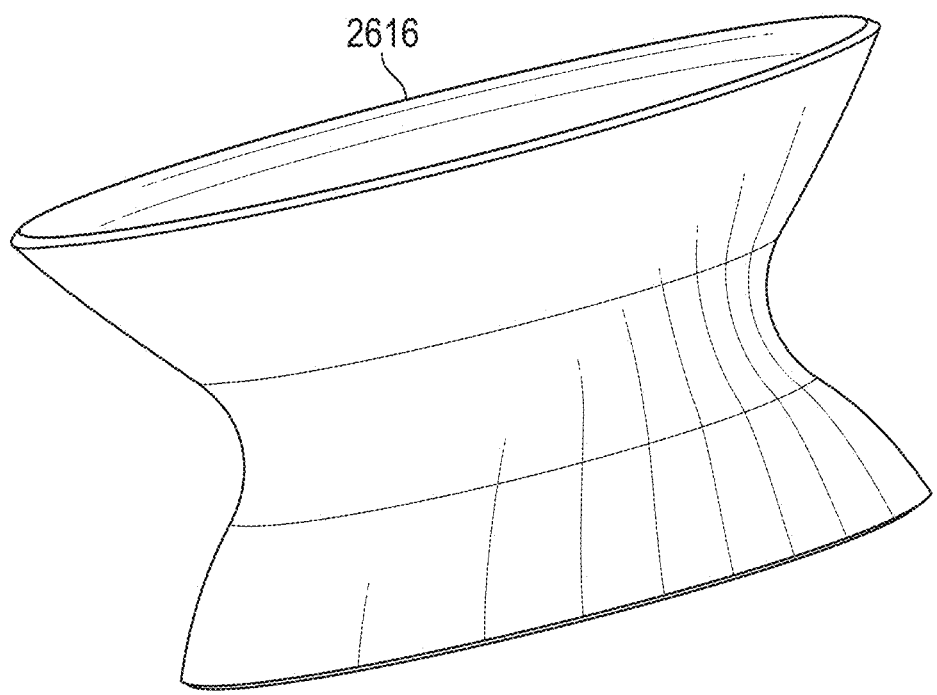
FIG. 26 shows an exemplary mandrel for shaping a skirt.

Referring to FIG. 26, if a skirt is knit or otherwise formed in a three-dimensional shape, an inner mandrel 2626 can be used (i.e., the skirt can be knit or formed over the mandrel). After the skirt has been formed around the mandrel 2626, the mandrel 2626 can dissolve or otherwise break apart to leave the formed skirt. In some embodiments, a woven fabric, such as a polyester weave, can be used to form the skirt over the mandrel 2626. In other embodiments, a polyurethane layer can be painted or otherwise applied over the mandrel 2626. The polyurethane can advantageously create fewer wrinkles than a woven fabric. If a polyurethane layer is used, a flap of material may be added in order to create some give in the skirt as the valve is packed and/or unpacked.

Figure 23A:
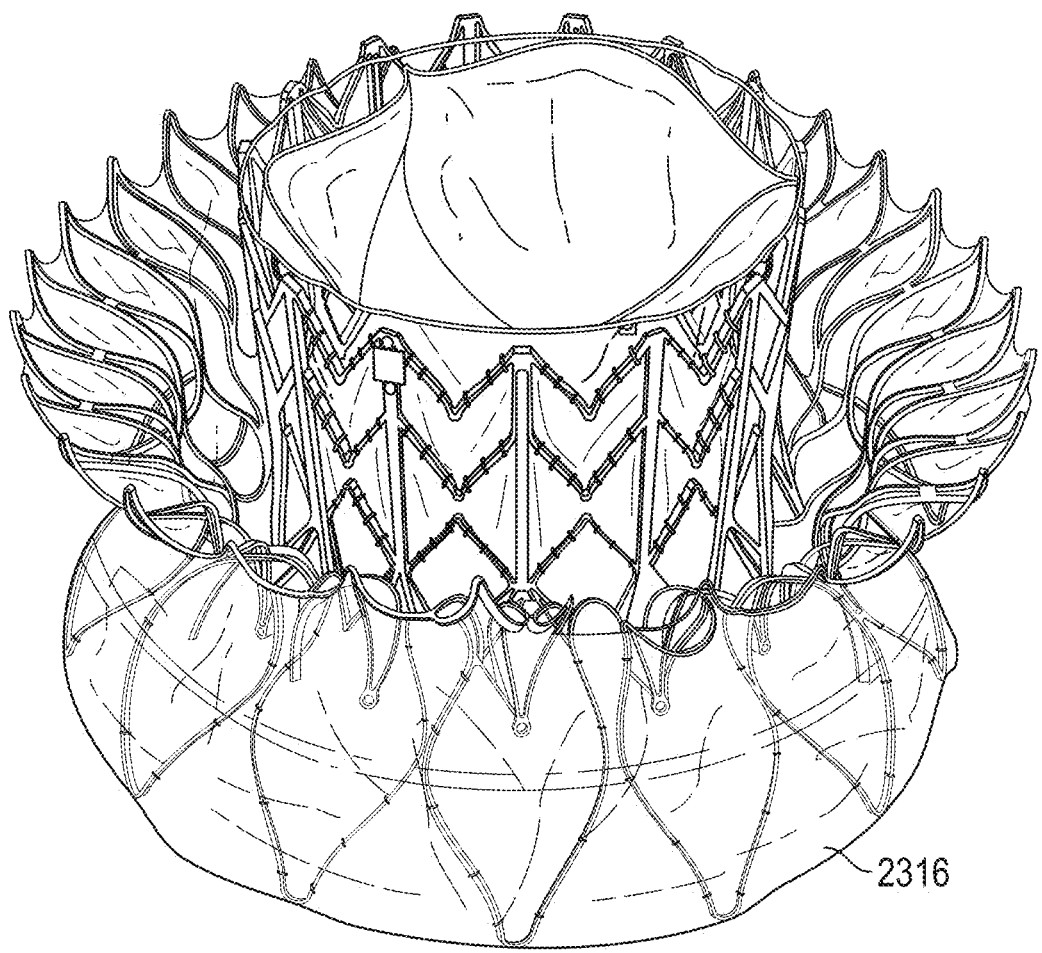
FIGS. 23A-23C show an exemplary mitral valve prosthesis with a skirt covering thereon.
Figure 23B:
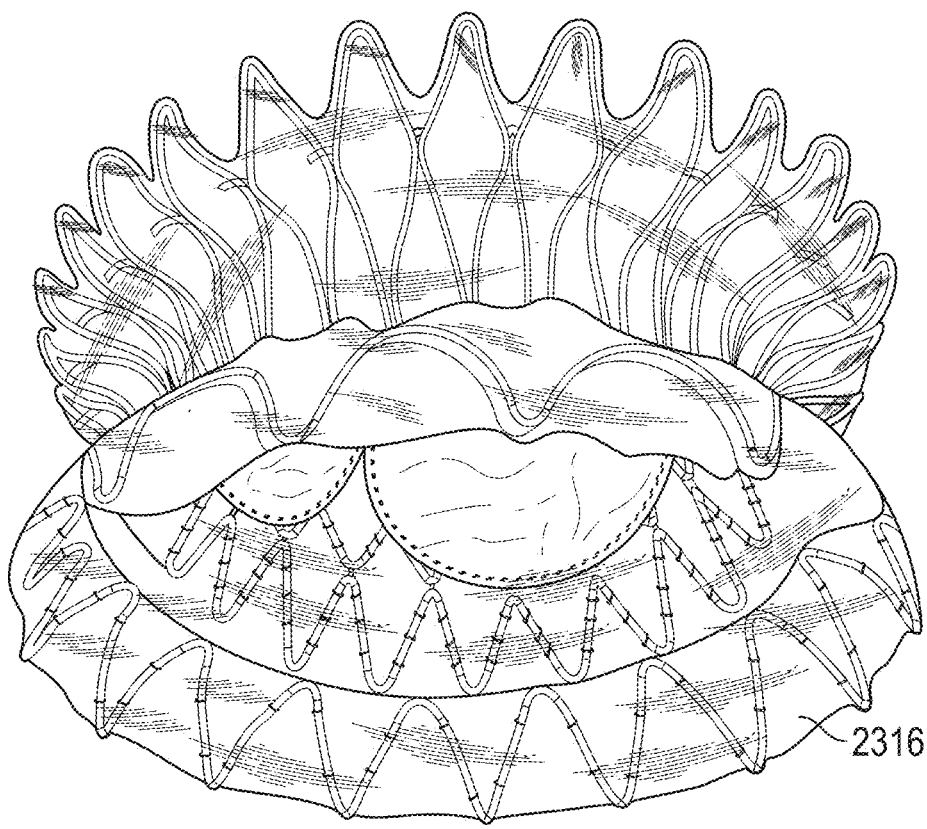
Figure 23C:
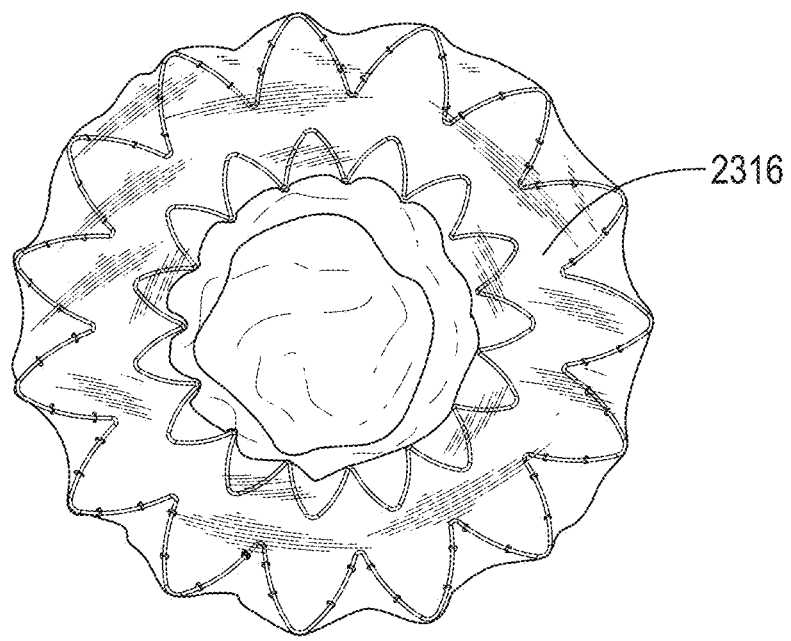

Further, in some embodiments, and as shown in FIGS. 23A-23C, the skirt 2316 can be cut in a saw-tooth pattern on the ventricular side to mimic the pattern of cells that extend to the outermost diameter of the ventricular anchor. Cutting the skirt in such a manner can help pack the ventricular anchor into the delivery device by reducing the packed diameter of the ventricular anchor.

The skirt can advantageously help block blood flow from one side of the valve over the other. The skirt can also help prevent the anatomy from having an adverse interaction with the frame itself.

In some embodiments, a coupler can be used to connect the strut frame to the anchor assembly. Rivets herein are an example of a coupler. The locations where components are secured to one another may be referred to as a coupling herein. Coupling also refers to the two components that are secured together. Riveting as used herein is an example of a method that plastically deforms a coupler to secure two or more components together at a coupling. Coupling and rivets are described further in U.S. patent application Ser. No. 14/677,334, filed Apr. 2, 2015, titled "REPLACEMENT CARDIAC VALVES AND METHODS OF USE AND MANUFACTURE," the entire contents of which are incorporated by reference herein.

Figure 10:
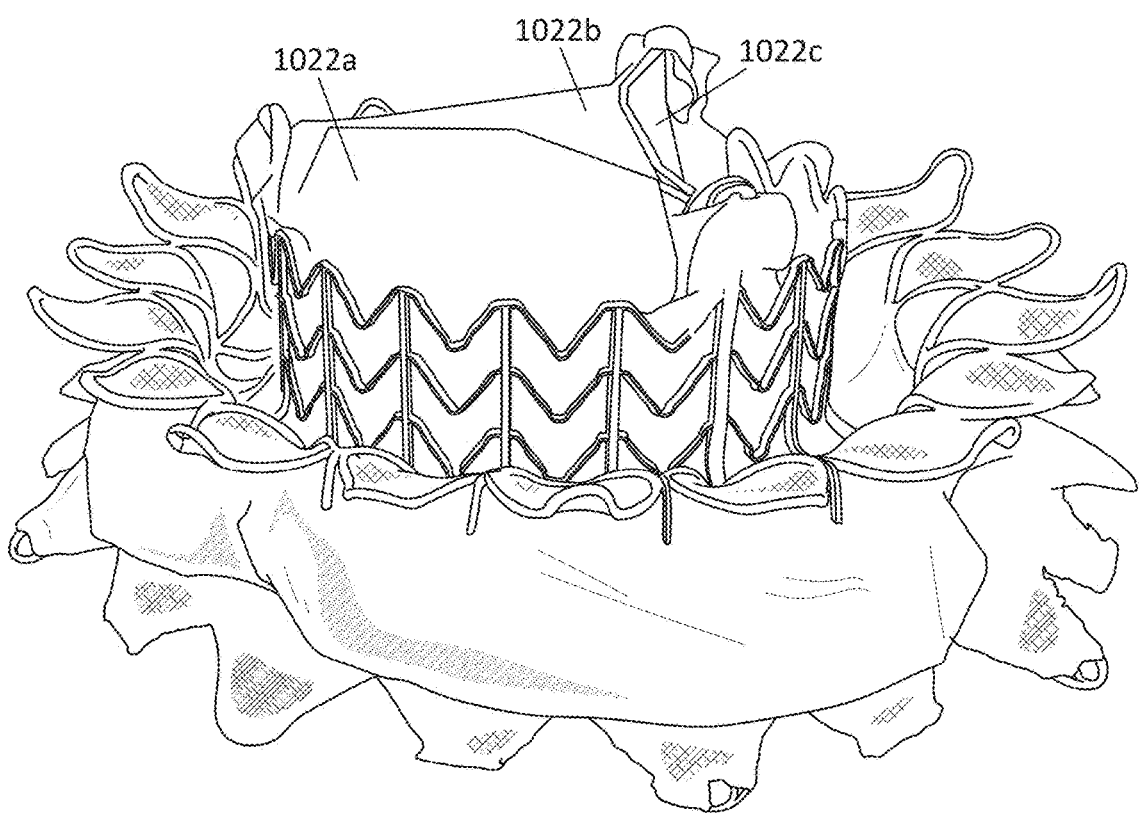
FIG. 10 shows an exemplary valve assembly including the anchor assembly, strut frame, skirt, and leaflets.
Figure 11A:
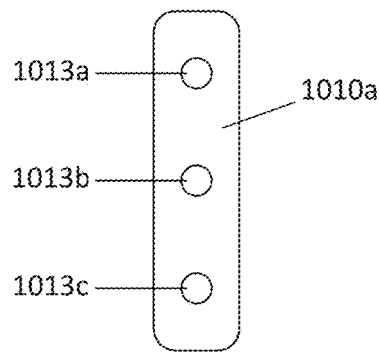
FIGS. 11A-11E show one exemplary mechanism of attaching leaflets to the strut frame.
Figure 11B:
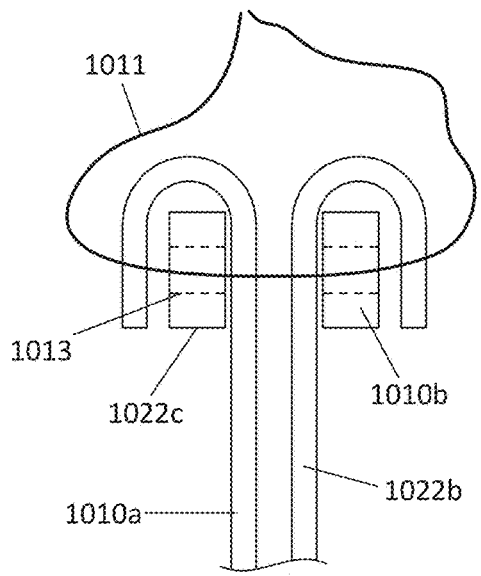
Figure 11C:
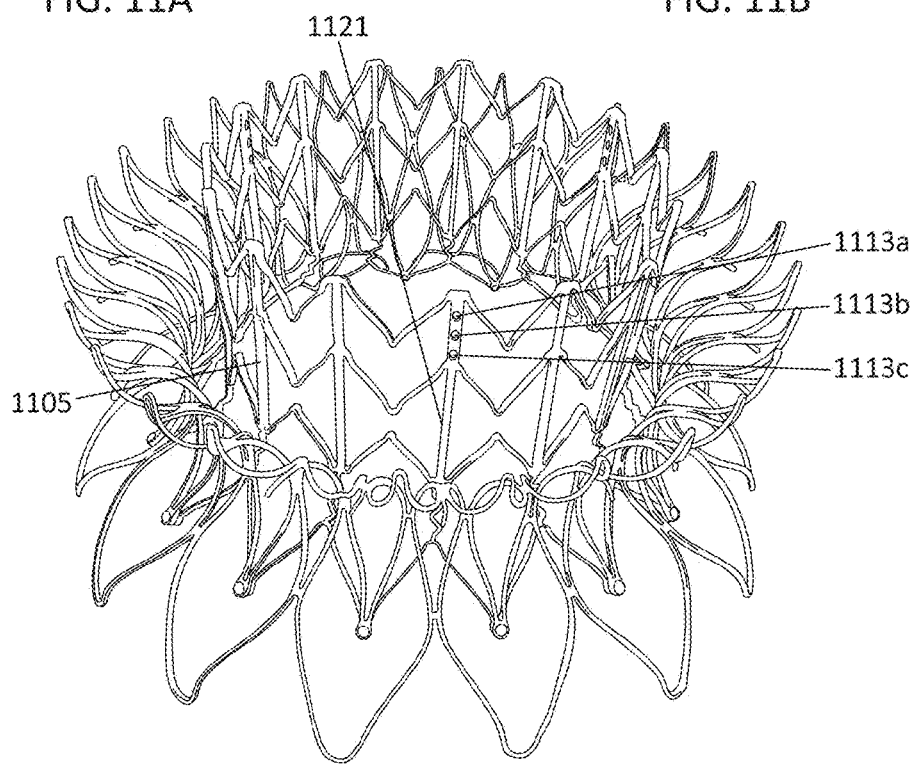
Figure 11D:
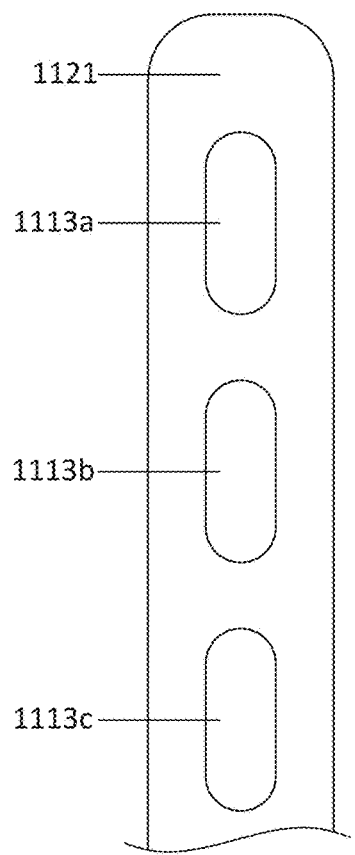
Figure 11E:
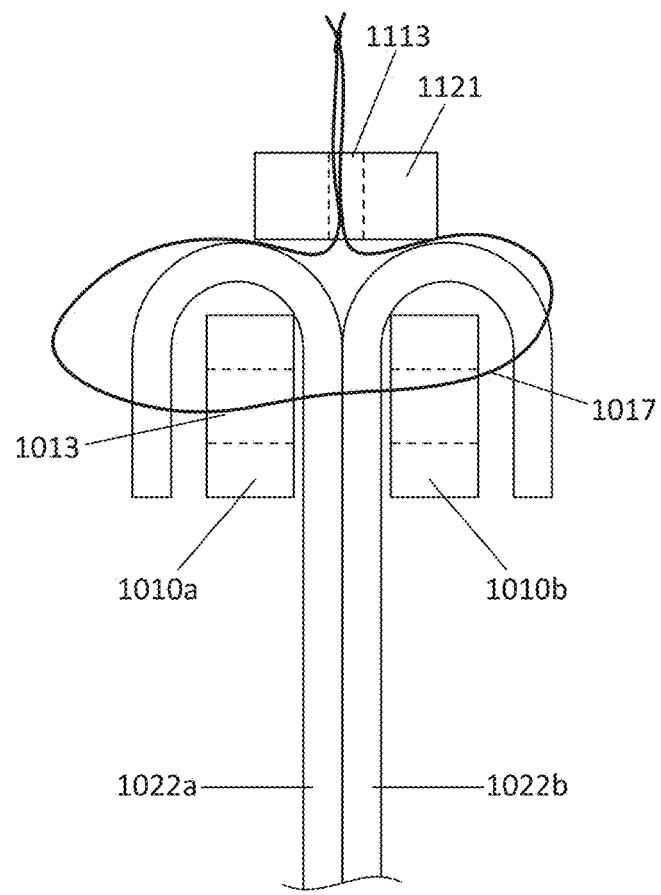
Figure 19:
FIG. 19 shows a method of sewing leaflets around the circumference of the strut frame.
Figure 21:
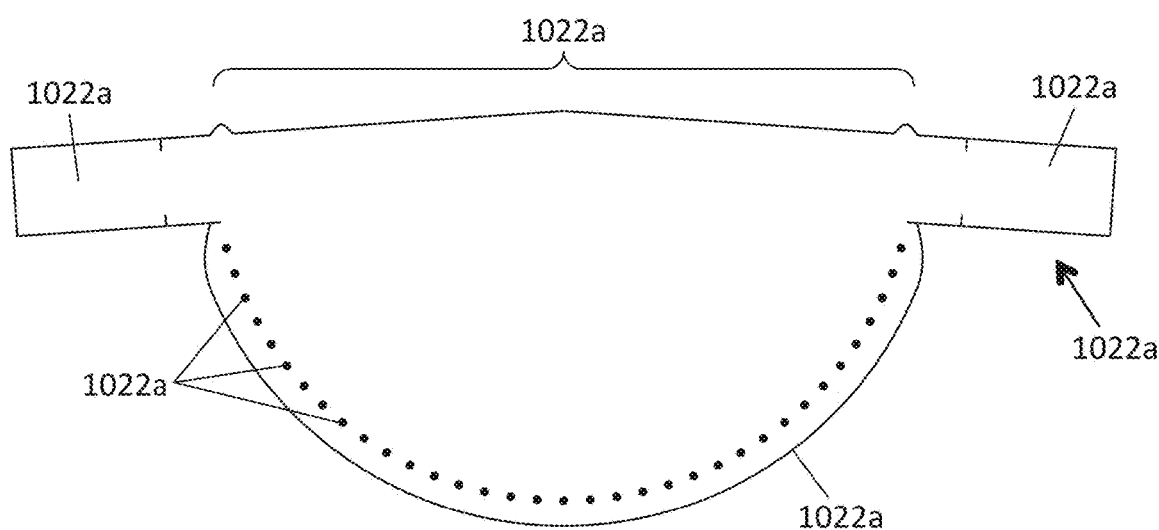
FIG. 21 shows an exemplary leaflet for use with the mitral valve prostheses described herein.

In some embodiments, the valve prostheses have been shown without leaflets for clarity. It is to be understood that each of the embodiments described herein can include replacement leaflets 1022*a,b,c* attached thereto, as shown in FIG. 10. An exemplary leaflet 2122 is shown in FIG. 21. The leaflet can include an outflow (or free) edge 2191 configured to float within the strut frame, an inflow edge 2193 configured to be sewn to the strut frame, and two arms 2195*a,b*. A plurality of sewing holes 2197 can provide for sewing of the leaflet 2122 to the strut frame. Thus, as shown in FIG. 19, the outer circumference of the leaflets at the inflow edges can be sewn to the strut frame and/or to the skirt covering the skirt frame. That is, while the commissures or edges of the leaflets can be attached as described above, the inflow edges of the leaflets can be sewn all around the circumference of the strut frame.

Further, the leaflets can be attached to any of the valve prosthesis designs in a variety of different ways.

For example, referring to FIGS. 11A-11F, two commissure plates 1010*a,b* can be used to sandwich the arms of the leaflets 1022*a,b* therebetween. The leaflets 1022*a,b* can then be sewn together (and to the plates 1010*a,b*) with one or more suture 1011 through holes 1013*a,bc*. After being sewn together, the joined leaflets and commissure plates can then be attached to the strut frame 1105 through, for example, a series of holes 1113*a,b,c* in one of the struts 1121 using a suture 1017 (which can be the same or different than suture 1011). The commissure plates 1010*a,b* can be made, for example, of stainless steel or plastic. Advantageously, the commissure plates 1010*a,b* can apply compression to the leaflets 1022*a,b* and distribute strains along the length of the commissure plates, thereby reducing tearing or strain propagation through the tissue.

Figure 12:
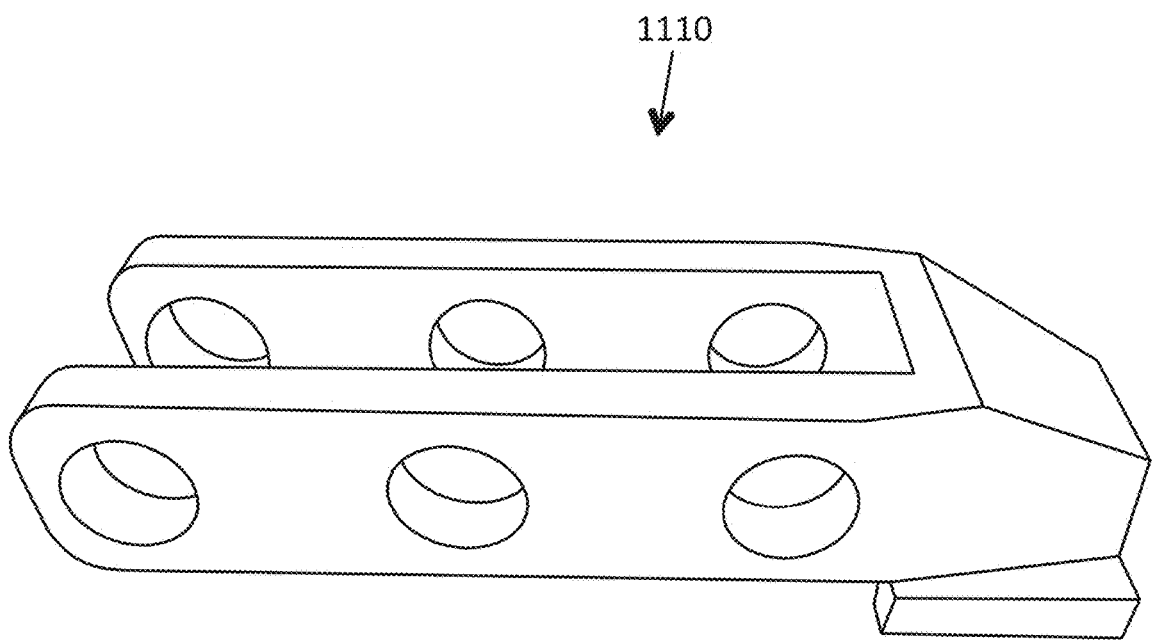
FIG. 12 shows another exemplary mechanism of attaching leaflets to the strut frame.

Another exemplary mechanism for leaflet attachment is shown in FIG. 12. Here, rather than using two commissure plates, a single u-shaped plate 1110 with a set of holes on either side can be used. In contrast to the commissure plates 1010*a,b*, the plate 1110 can place a fixed amount of compression on the leaflets that are sandwiched therebetween.

Figure 14:
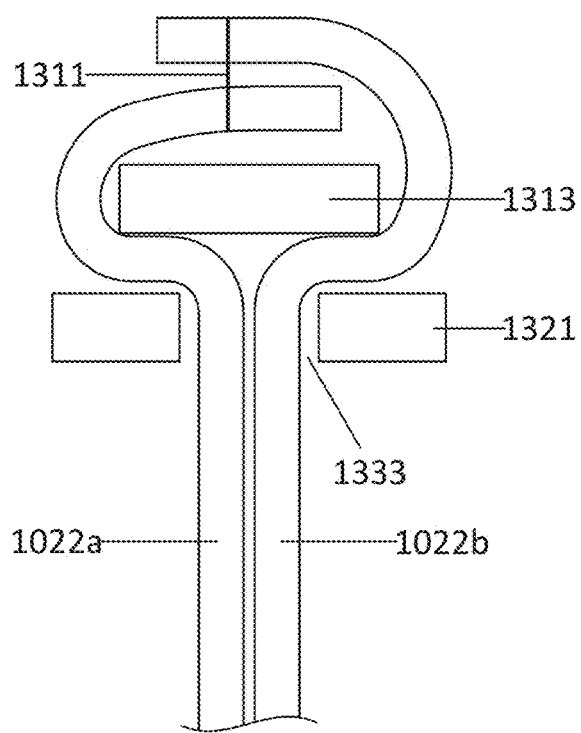
FIG. 14 is a cross-section showing another exemplary mechanism of attaching leaflets.
Figure 15A:
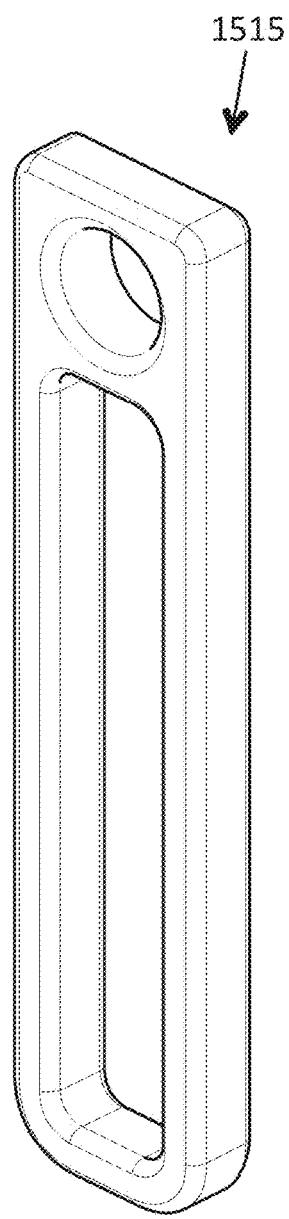
FIG. 15A-15C show another exemplary mechanism of attaching leaflets.
Figure 15B:
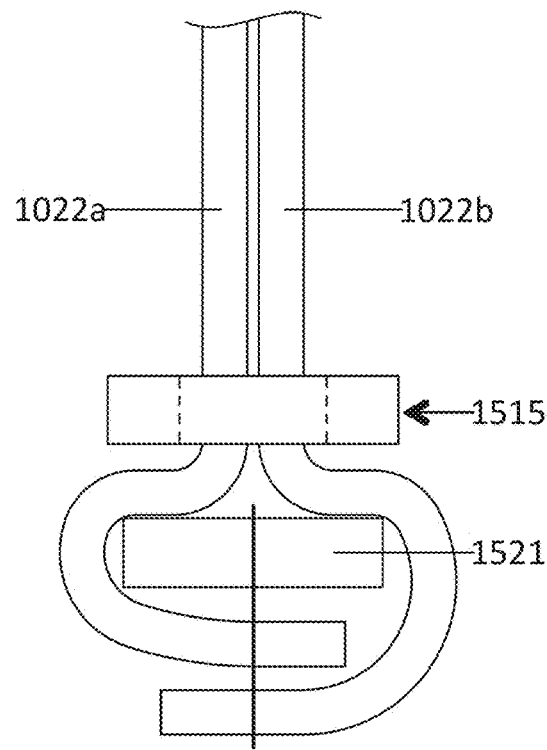
Figure 15C:
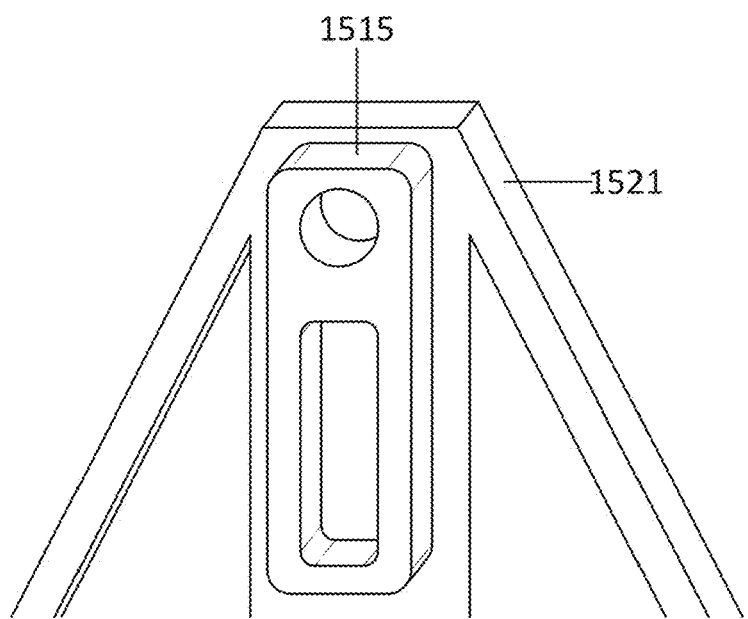
Figure 16A:
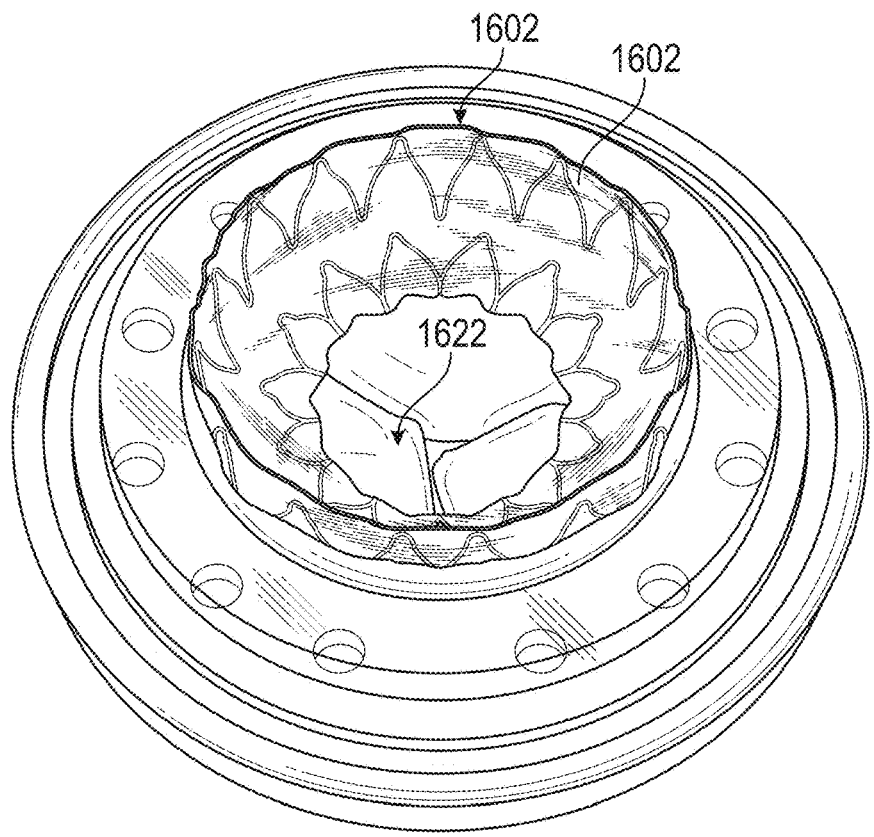
FIGS. 16A-16D show a holder including an exemplary mitral valve prosthesis with a skirt or covering.
Figure 16B:
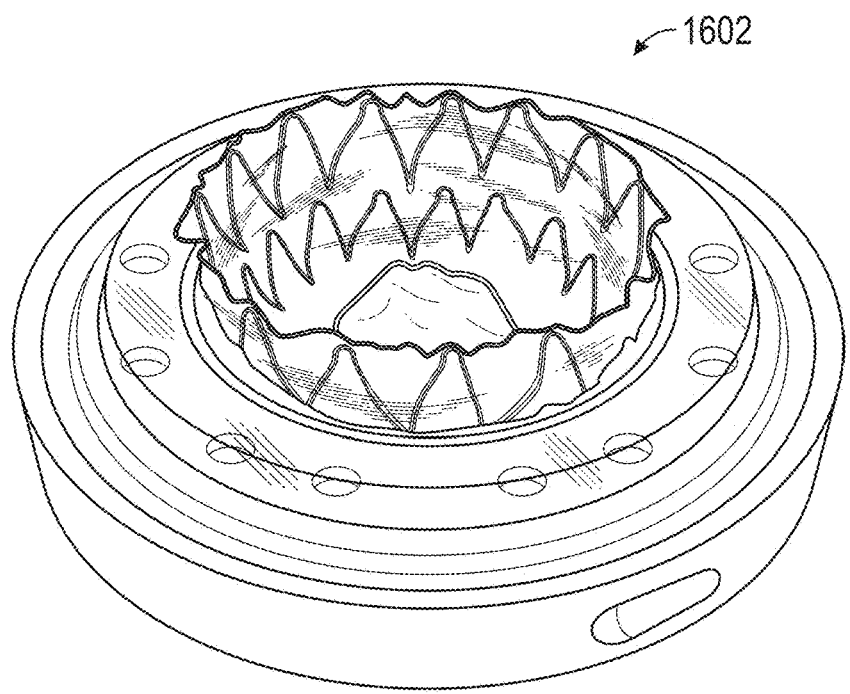
Figure 16C:
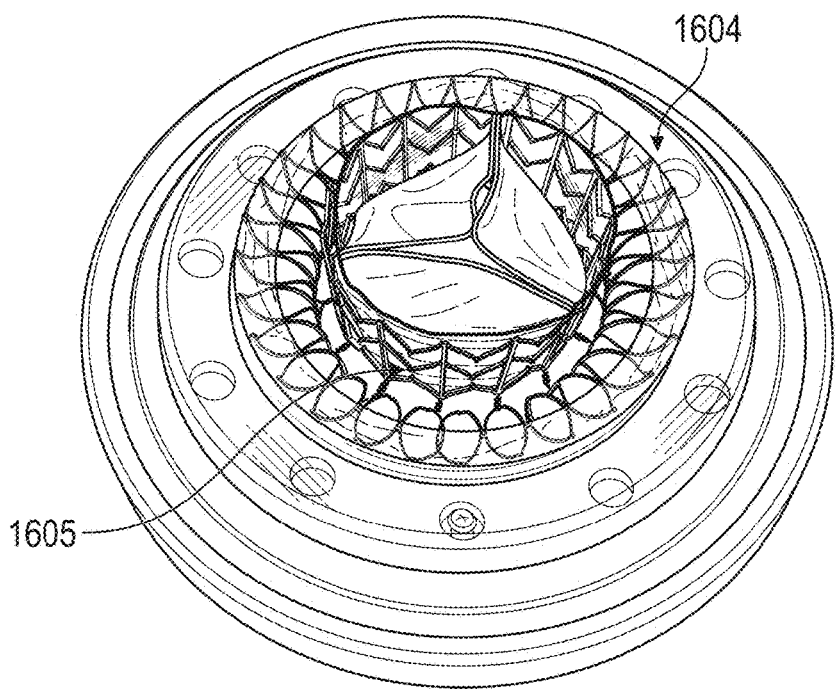
Figure 16D:
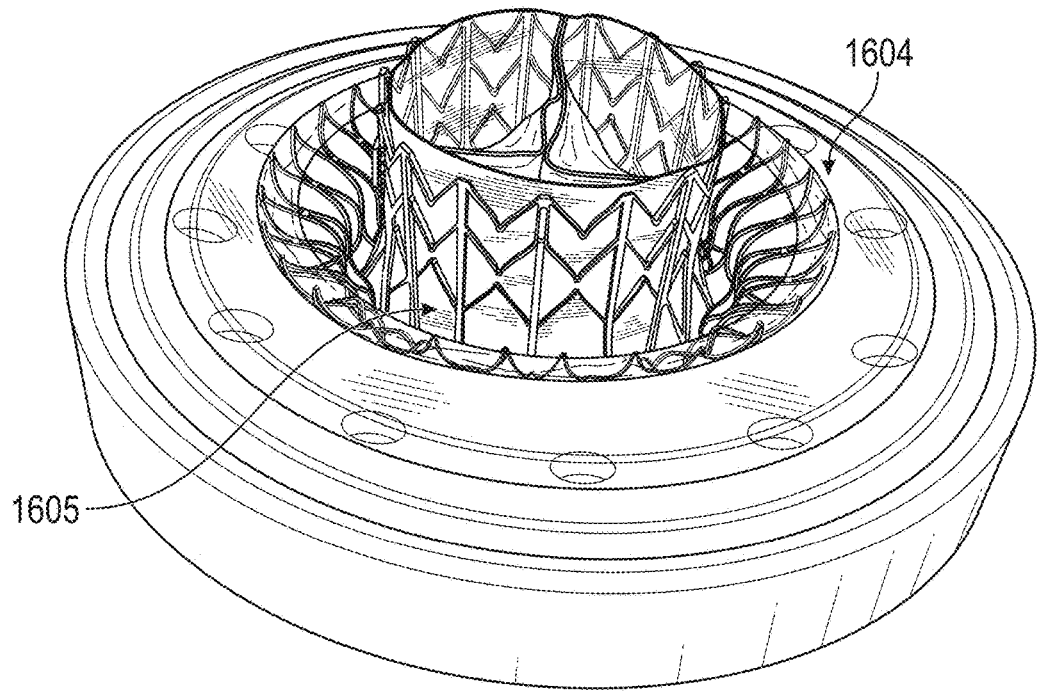
Figure 17A:
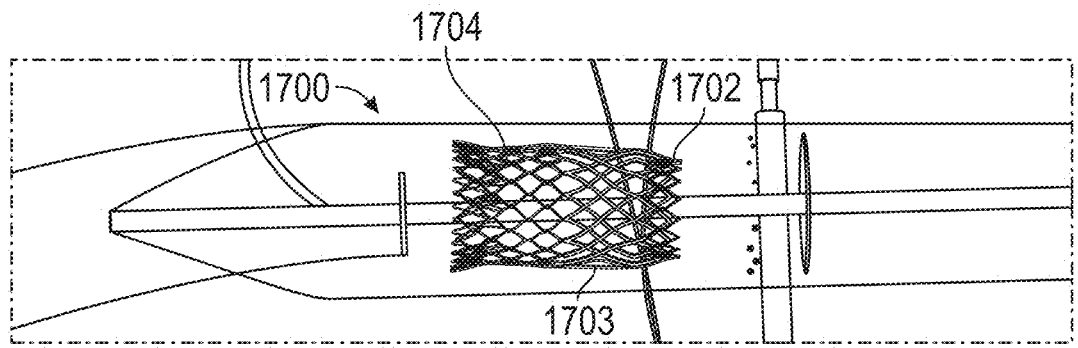
FIGS. 17A-17J show an exemplary method of deploying a valve prostheses.
Figure 17B:
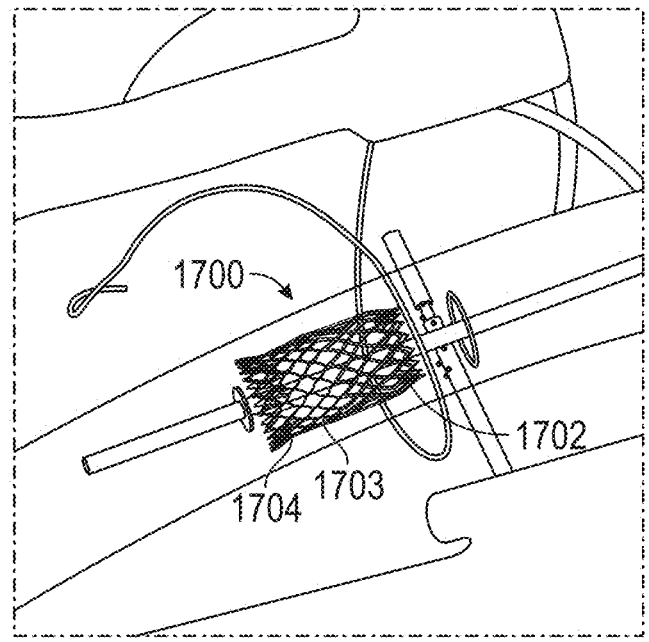
Figure 17C:
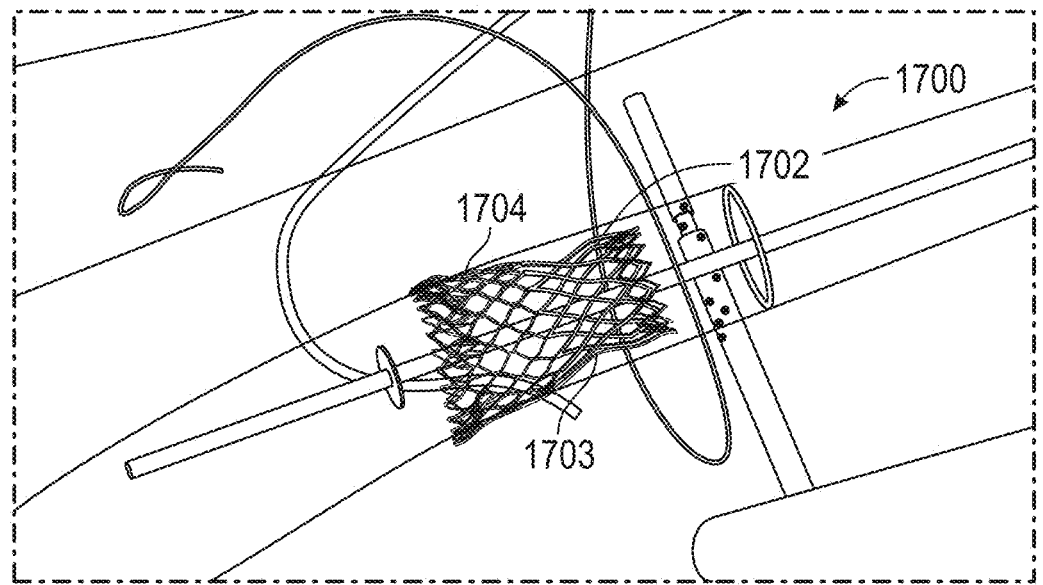
Figure 17D:
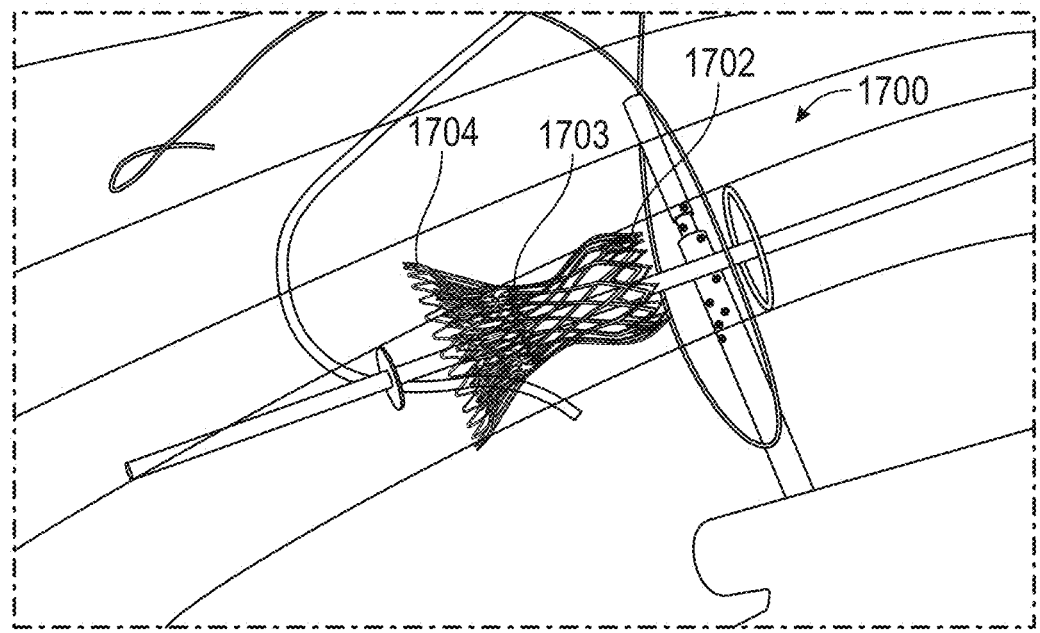
Figure 17E:
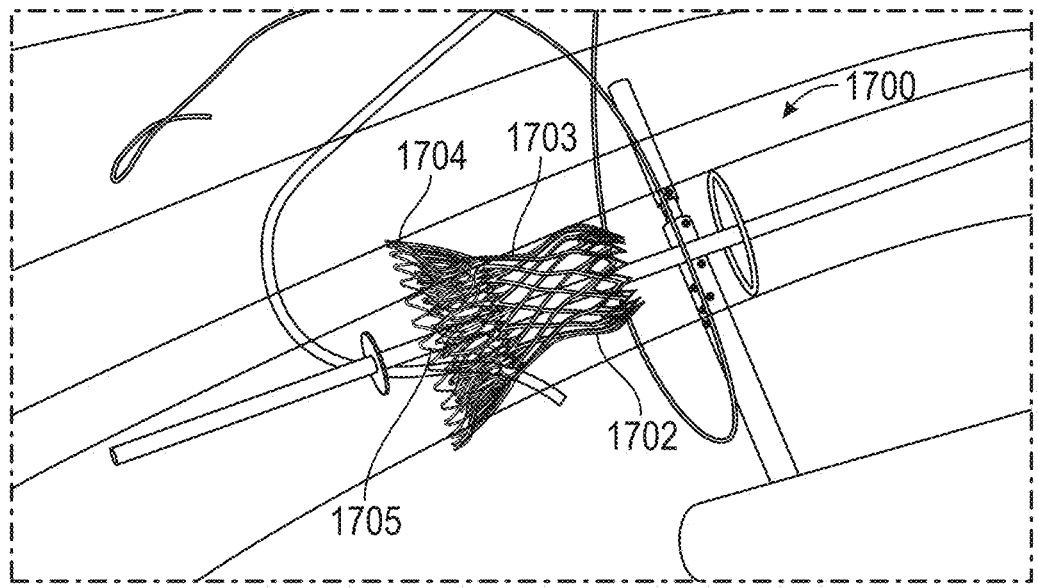
Figure 17F:
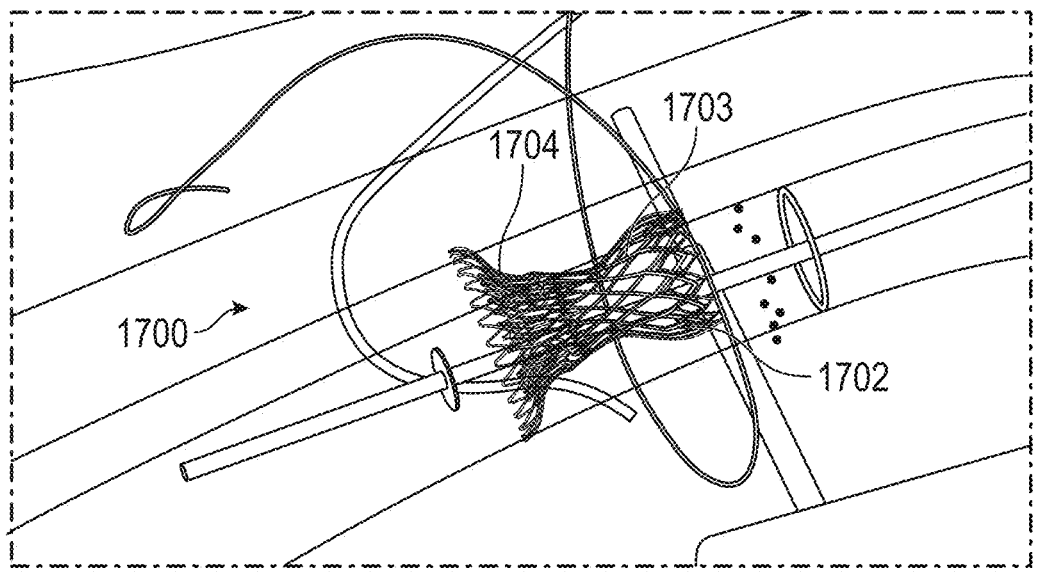
Figure 17G:
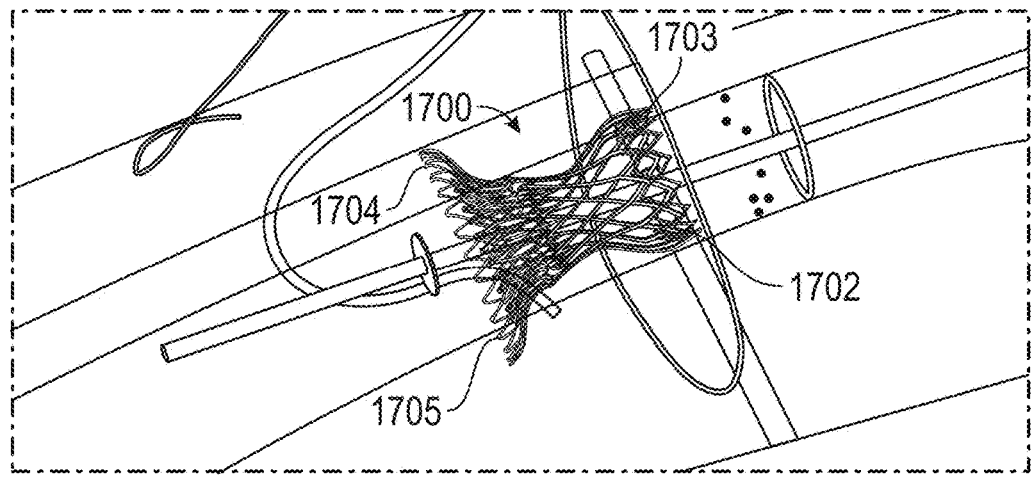
Figure 17H:
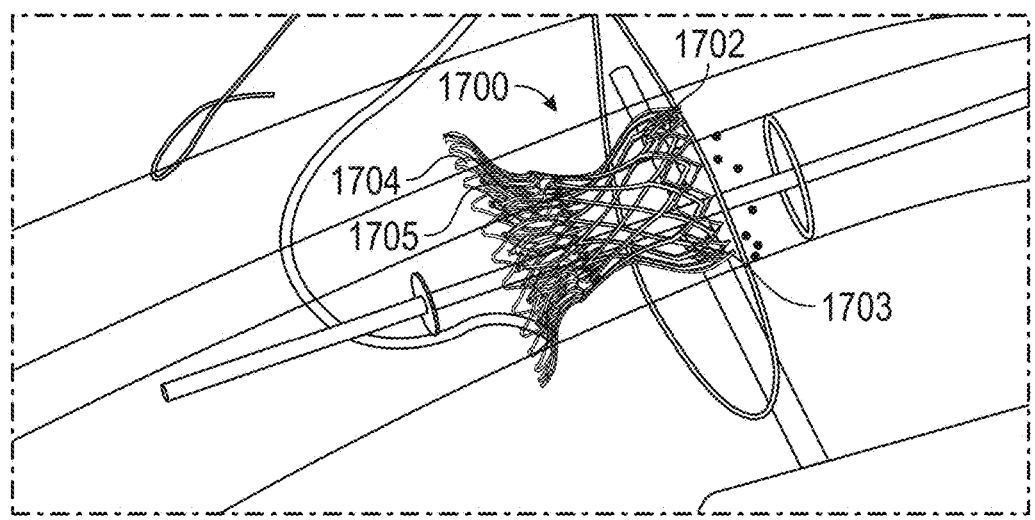
Figure 17I:
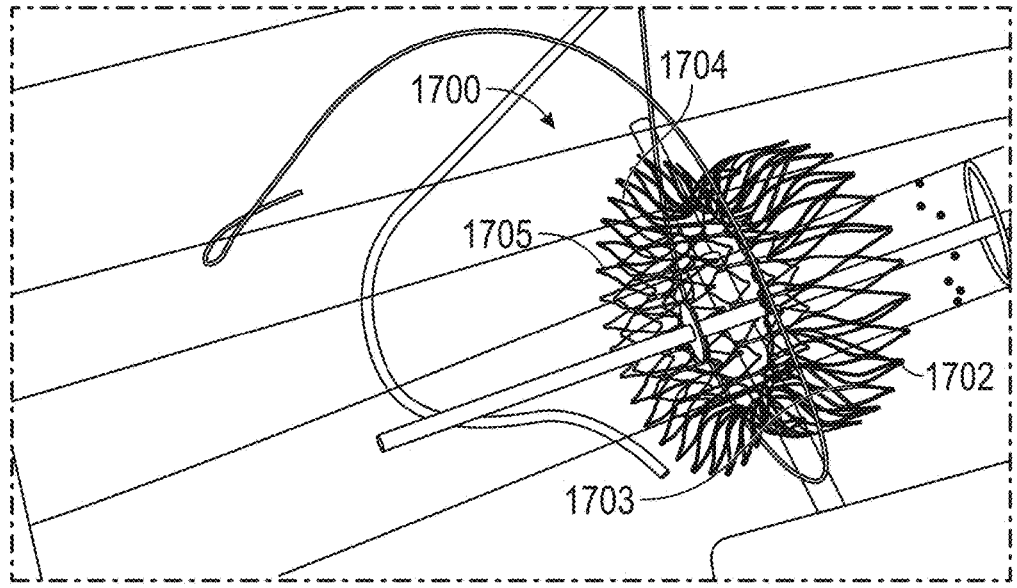
Figure 17J:
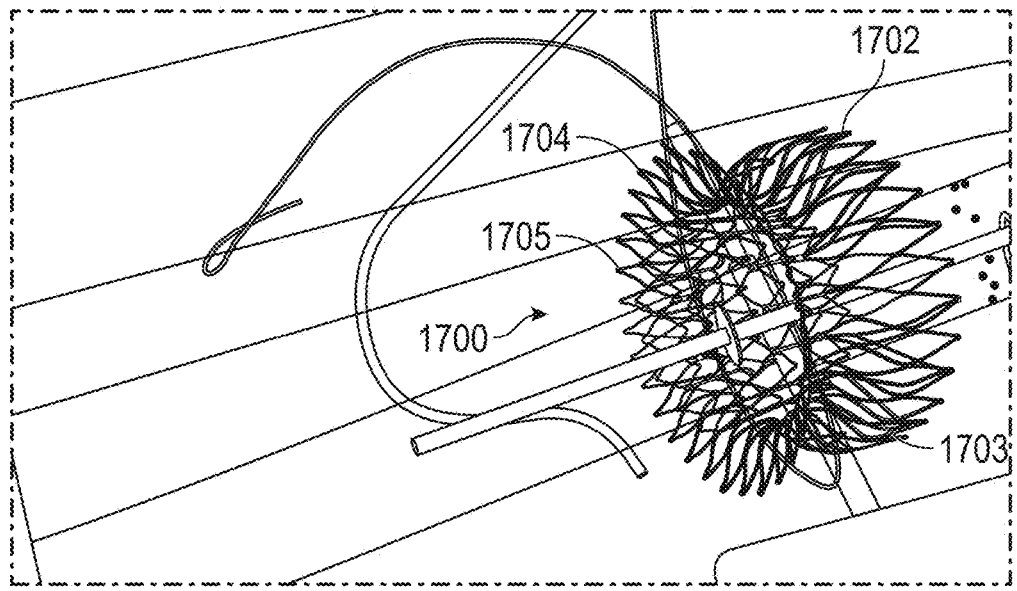
Figure 18A:
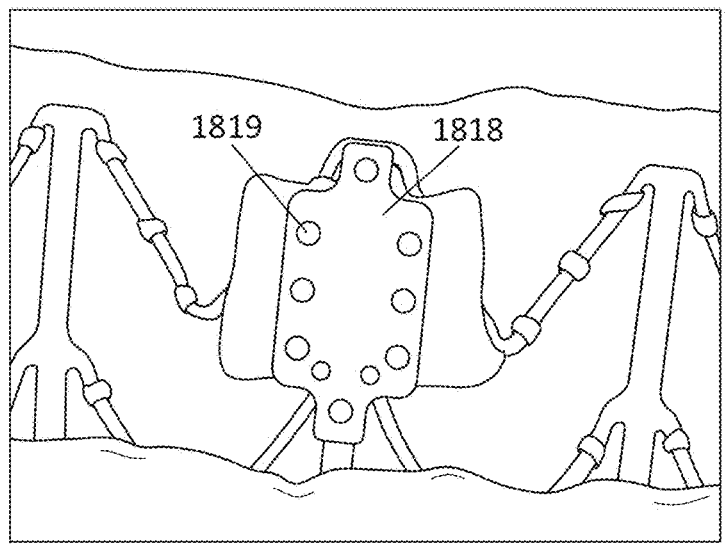
FIGS. 18A-18E show another exemplary mechanism of attaching leaflets to the strut frame.
Figure 18B:
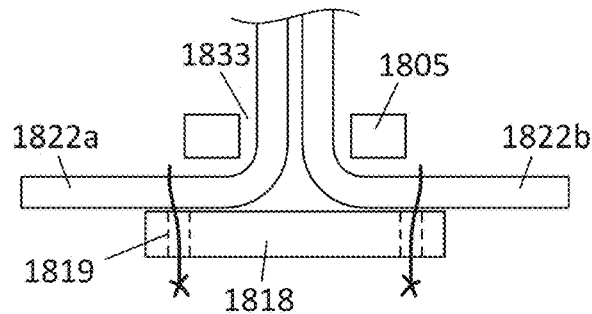
Figure 18C:
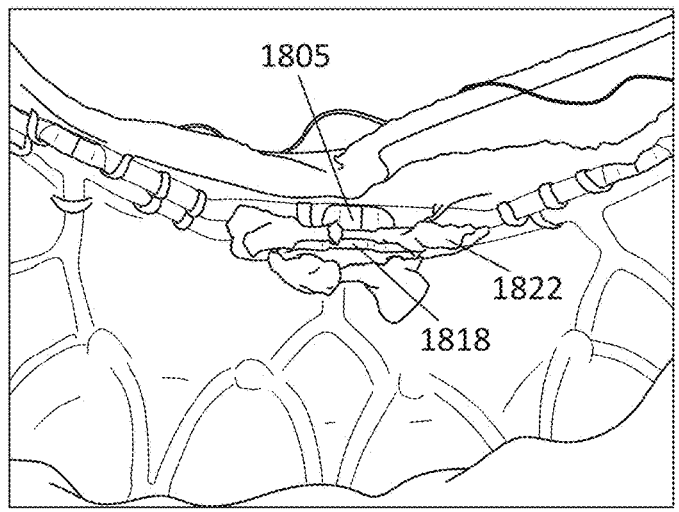
Figure 18D:
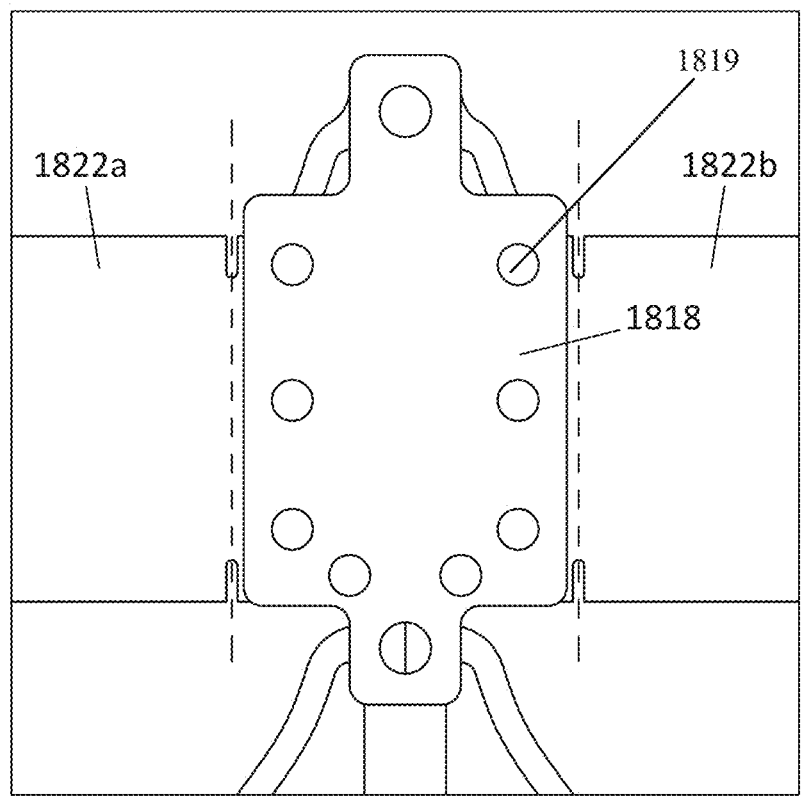
Figure 18E:
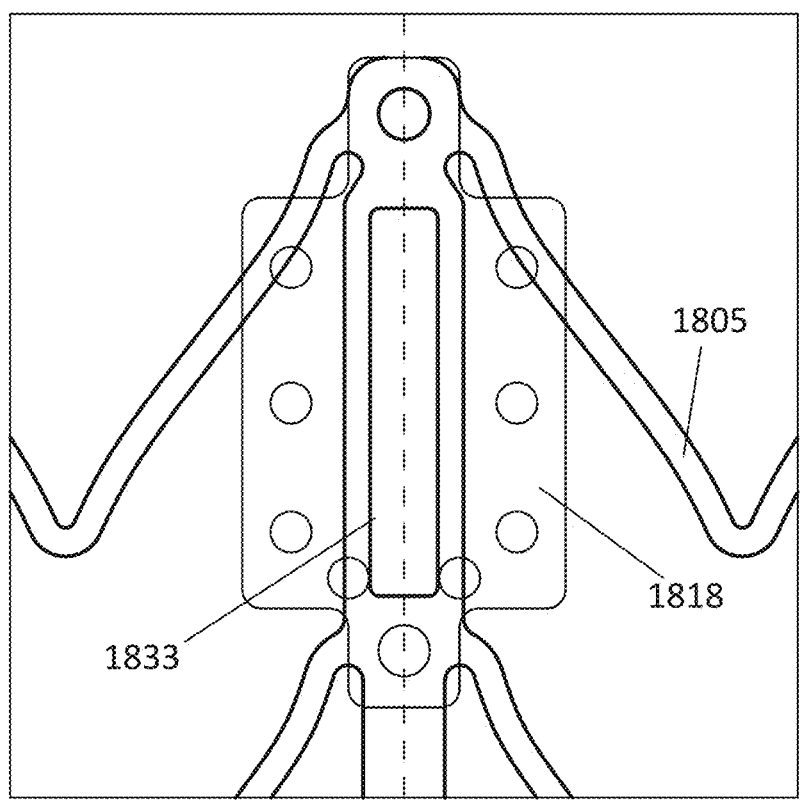

Additional exemplary mechanisms for leaflet attachment are shown in FIGS. 14 and 15A-15C. In the version of FIG. 14, the arms of two leaflets 1022*a,b* are pulled through a slot 1333 that is part of a strut 1321 of the strut frame. A secondary member 1313 having a width greater than the width of the slot 1313 is placed against both arms leaflets, and then the arms of the leaflets 1022*a,b* are wrapped around the secondary member 11313 and attached together with a suture 1311 or staple. The secondary member 1313 can be coupled to the strut frame, for example with a rivet. In a similar embodiment, shown in FIGS. 15A-15C, the leaflets 1022*a,b* can be passed through a slot in a secondary member 1515 and then wrapped around a strut 1521 of the strut frame. Advantageously, the mechanisms of FIGS. 14 and 15A-C evenly distribute high stress areas of leaflet along the length of strut 1312 or riveted slot 1321. The load distribution along the given length of these members decrease stresses in comparison to attachment methods where many stress concentrations are created i.e. sutures.

Another exemplary mechanism for leaflet attachment is shown in FIGS. 18A-18E. In this embodiment, a plate 1818 including a plurality of holes 1819 can be positioned on the outside of the strut frame 1805. Further, the strut frame 1805 can include a slot 1833 therethrough. The arms of the leaflets 1822*a,b* can then be extended through the slot 1833 and flattened against the outer surface of the strut frame 1805. The plate 1818 can be placed against the arms of the leaflets 1822*a,b* and then sutured to the arms of the leaflets, e.g., through the holes 1819. The arms of the leaflets 1822*a,b* can thus be sandwiched between the plate 1818 and the strut frame 1805. In some embodiments, the suture is attached to a skirt or fabric layer on the strut frame 1805 rather than directly to the strut frame.

Figure 27A:
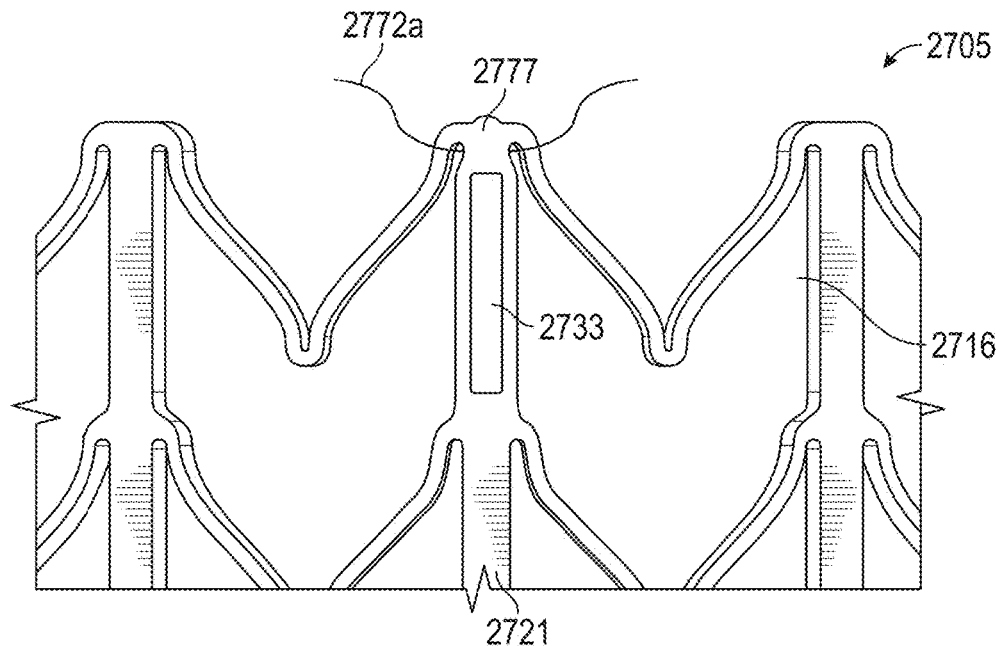
FIGS. 27A-27Q show another exemplary method of attaching leaflets to a mitral valve prosthesis.
Figure 27B:
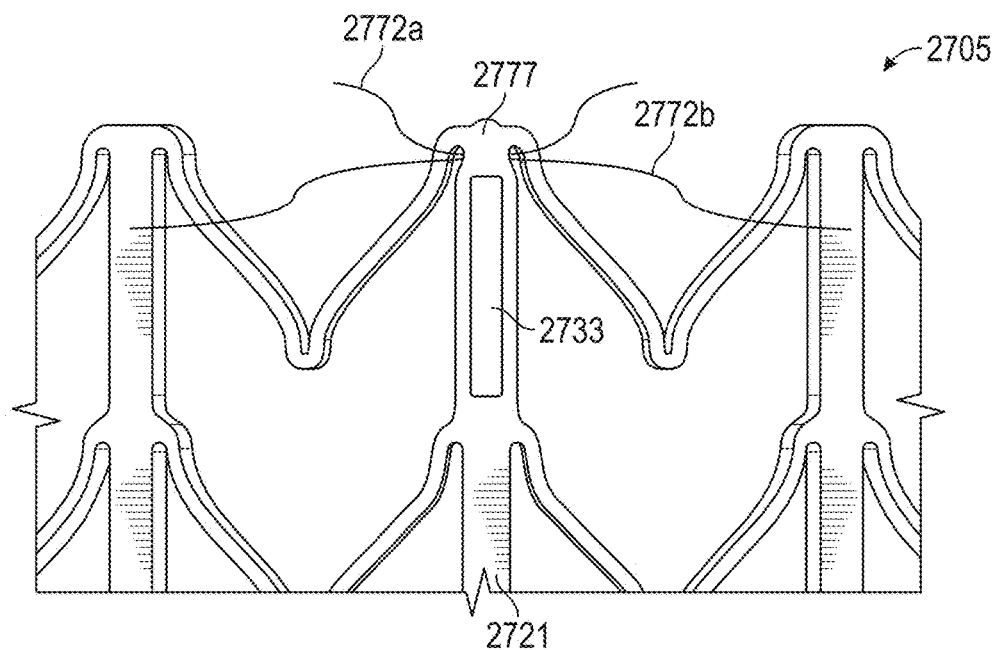
FIG. 27B shows a second suture positioned therearound.
Figure 27C:
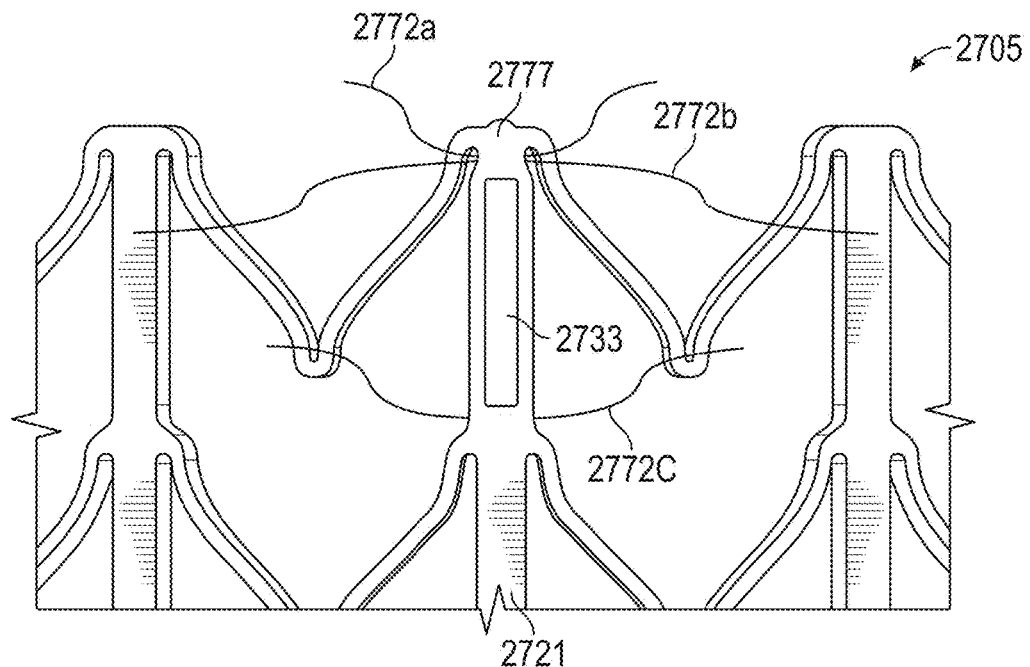
FIG. 27C shows a third suture positioned therearound.
Figure 27D:
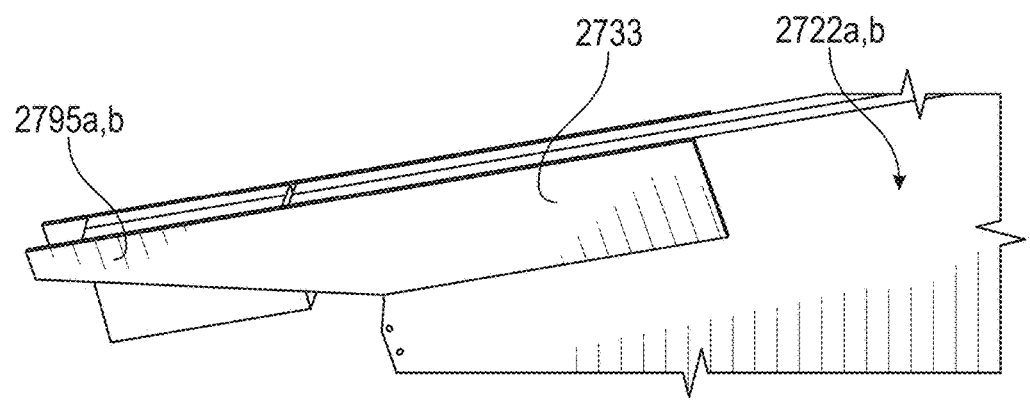
FIG. 27D shows the alignment of leaflet protectors.
Figure 27E:
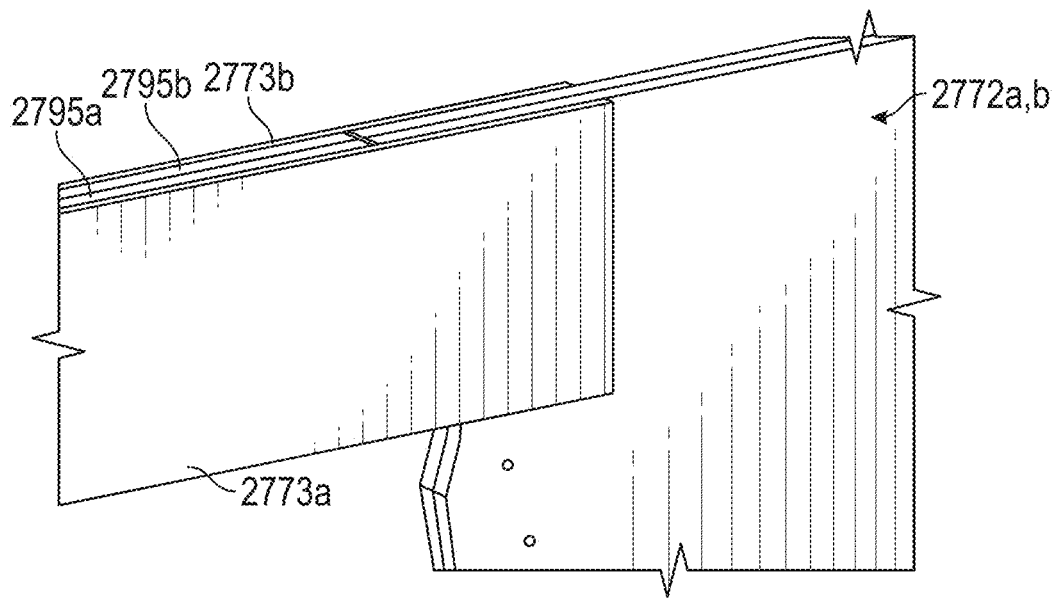
FIG. 27E shows the positioning of the leaflets such that they are flush with one another. FIGS.
Figure 27F:
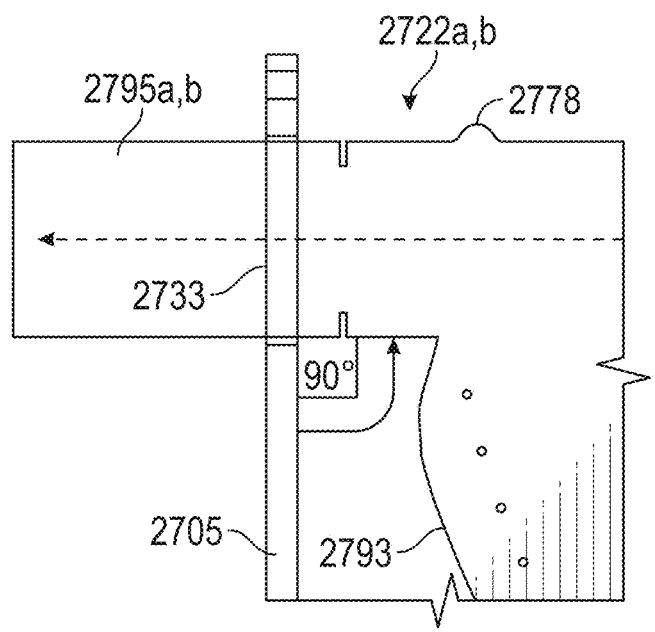
FIG. 27I shows separation of the two leaflets to attach at additional commissure points.
FIG. 27J shows an inflow view of the leaflets after they have been attached at the commissure attachment points.
FIG. 27K shows an outflow view of the leaflets after they have been attached at the commissure attachment points.
FIG. 27L shows the arms of the leaflets wrapped around the strut frame.
FIG. 27M shows the leaflet protectors wrapped inside of the strut frame.
FIG. 27N shows alignment of the leaflet arms with the strut frame.
FIG. 27O shows placement of the plate over the strut frame.
FIG. 27P shows wrapping of two sutures around the plate.
Figure 27G:
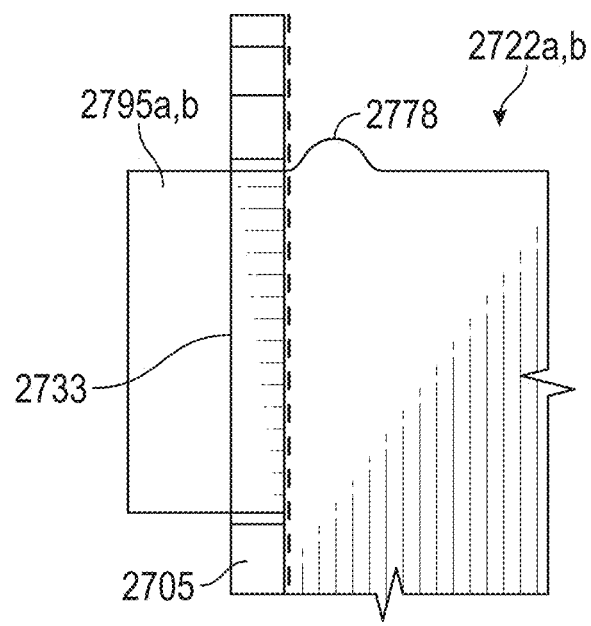
Figure 27H:
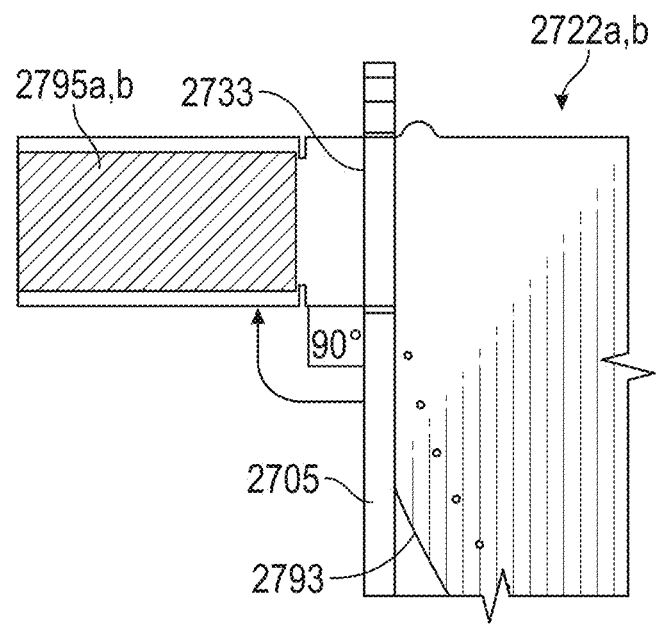
Figure 27I:
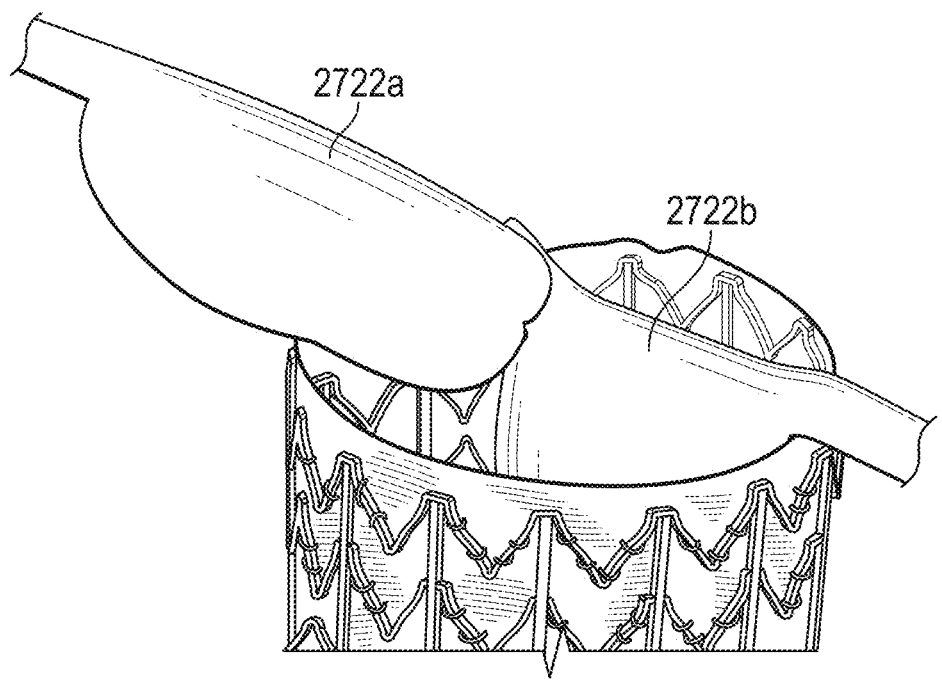
Figure 27L:
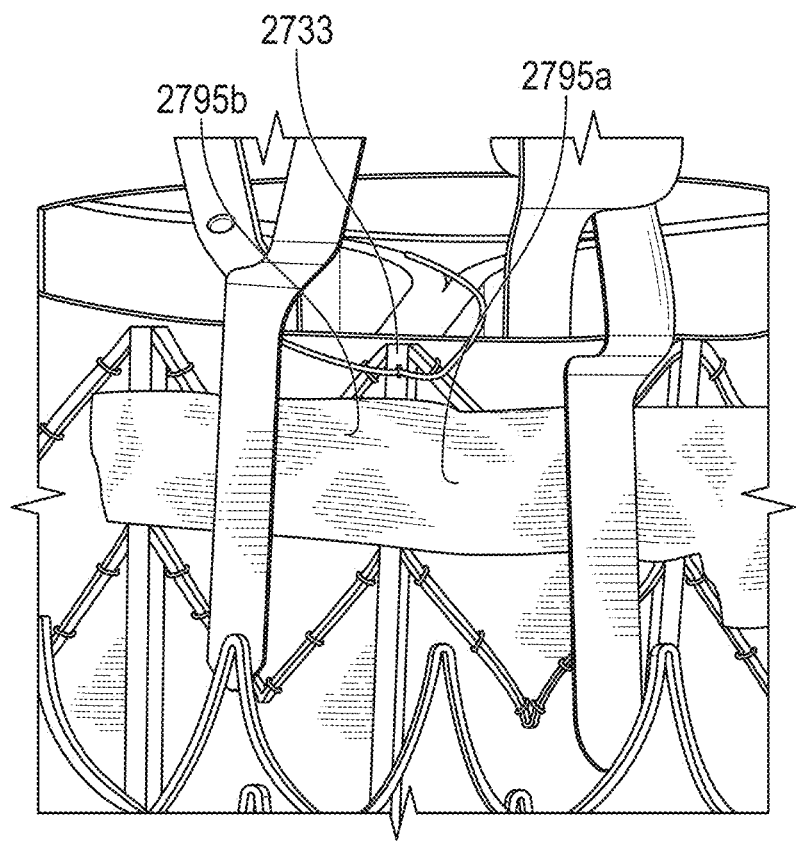
Figure 27J:
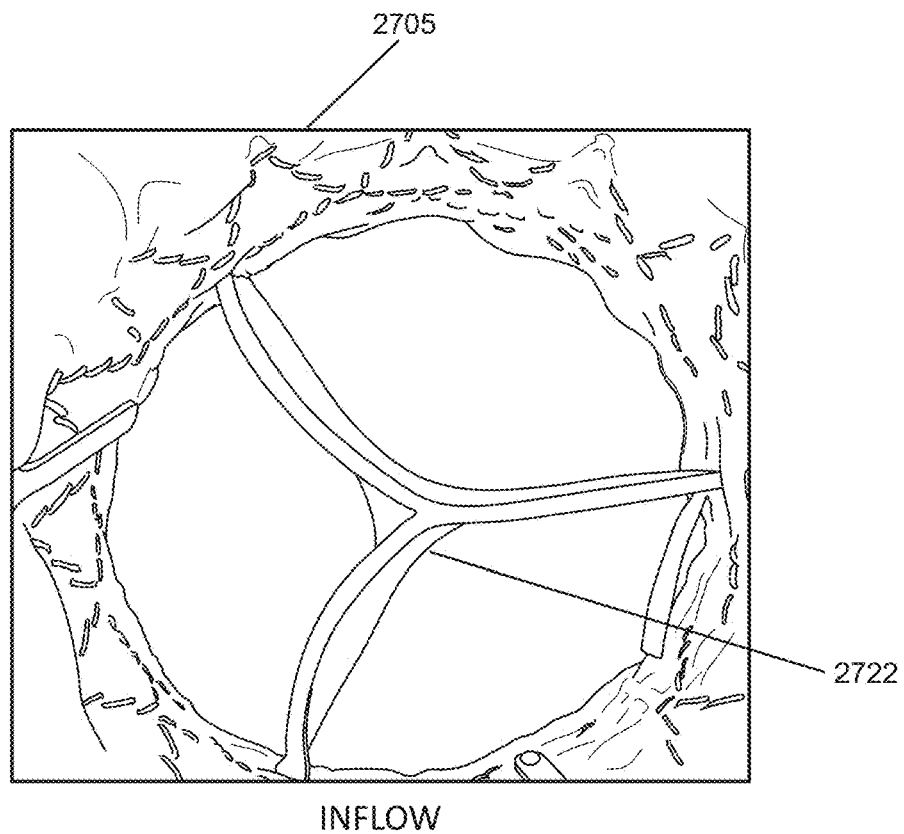
Figure 27K:
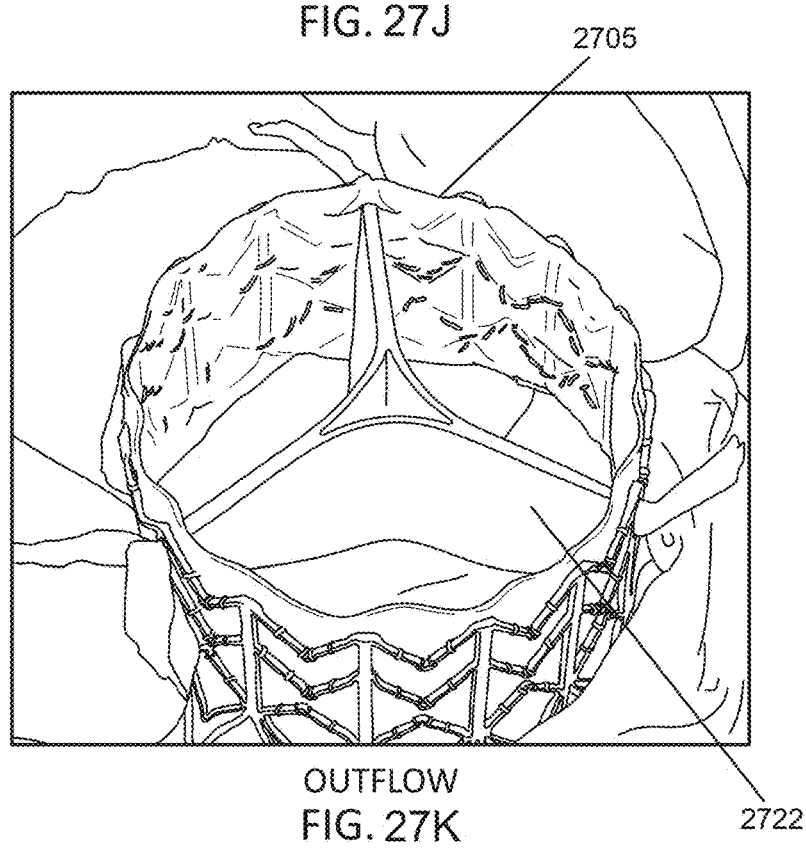
Figure 27M:
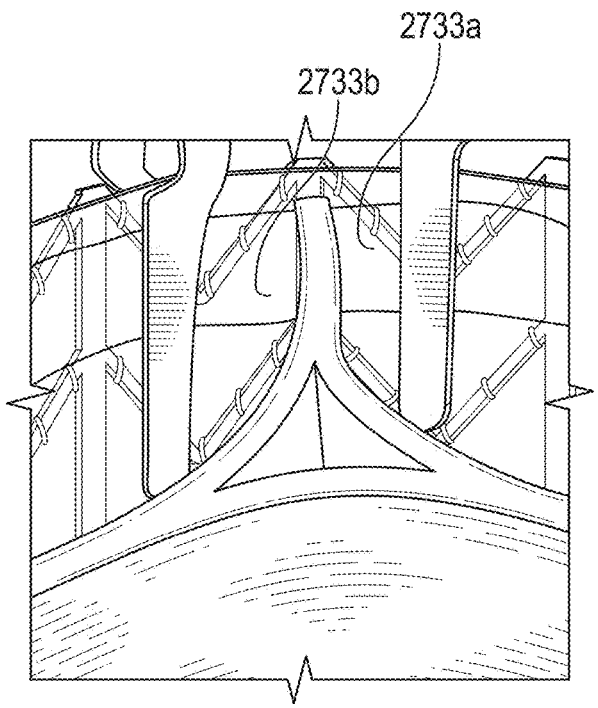
Figure 27N:
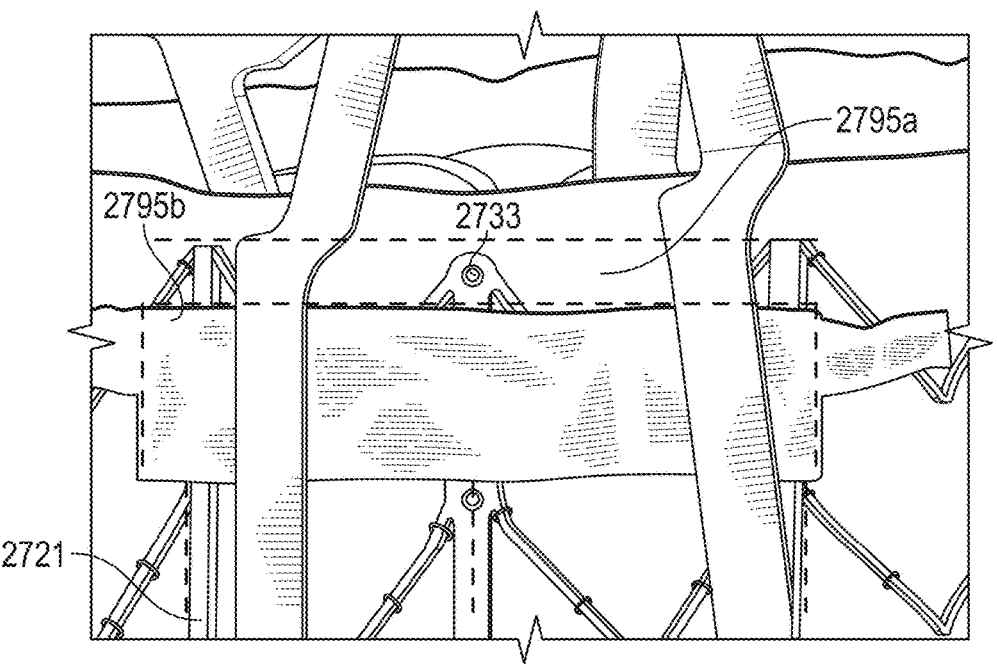
Figure 27O:
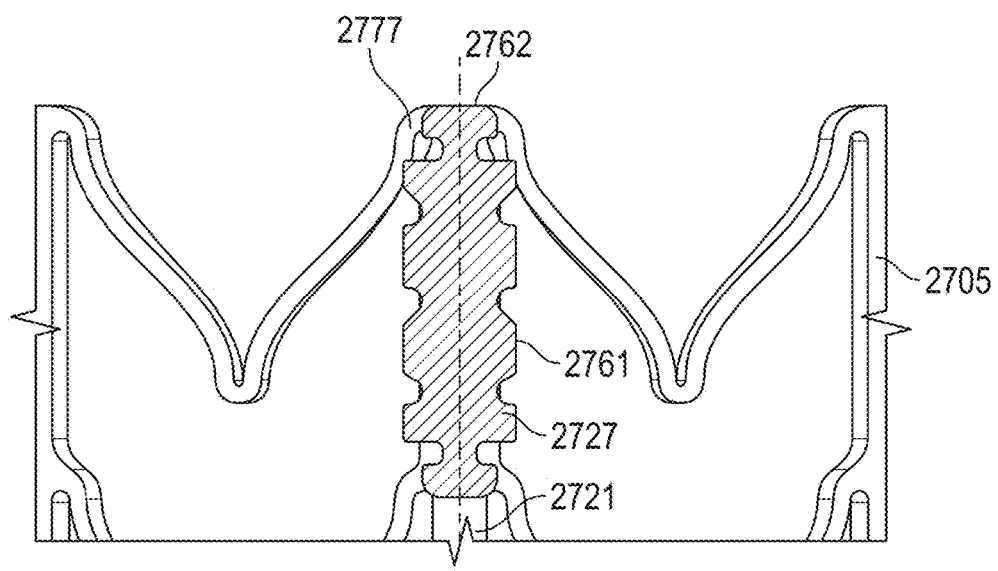
Figure 27P:
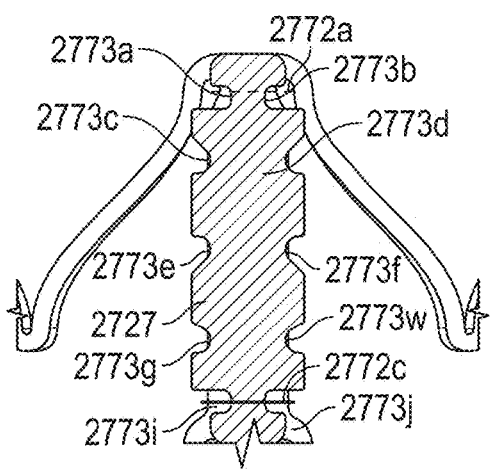
Figure 27Q:
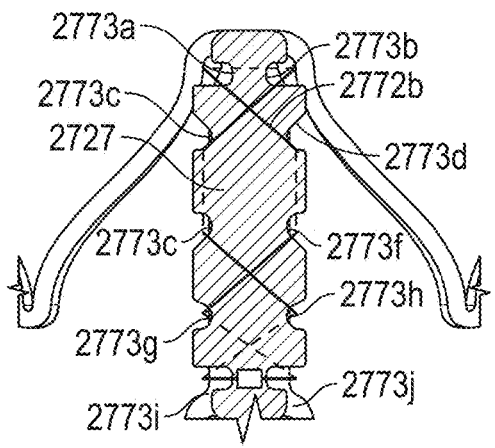

Another exemplary mechanism for leaflet attachment is shown in FIGS. 27A-27R. In this embodiment, a plate 2727 with a plurality of channels 2773 (or open slots or indents) in the sides thereof can be positioned on the outside of the strut frame 2705. The channels 2773 can extend diagonally towards the center of the plate 2727. There can be two or more channels 2773, such as between 6 and 12 channels 2773, such as ten channels 2773. Further, the frame 2705 can include three slots 2733 therethrough (one for each attachment point) that are positioned equidistant from one another around the circumference of the strut frame 2705. The slots 2733 can be positioned within a strut 2721 at the ventricular end. To attach the leaflets 2722a,b to the frame 2705, a first suture 2772a can first be threaded between the frame 2705 and skirt 2716 fabric and around the slot 2733. The first suture 2772a can then be slid distally towards the ventricular tips 2777 of the strut frame 2705 (FIG. 27A). At FIG. 27B, a second suture 2772b is threaded similarly to the first suture 2772a. At FIG. 27C, a third suture 2772c is pierced through the fabric just distal to the slot 2733 from the outside and back, wrapping the third suture 2772c around the frame 2705. At FIG. 27D, two leaflets 2722a,b can be aligned, and leaflet protectors 2773 (e.g., made of a lubricious fabric, such as a polyester weave) can be placed along the outward-facing side of each arm 2795a,b of the leaflets 1022a,b. At FIG. 27E, the arms 2795a,b and leaflet protectors 2773a,b of the leaflets 1022a,b can remain flush. As shown in FIGS. 27G-I, the leaflet arms 2795a,b can be slid through the slot 2733. As shown in FIG. 27F, the arms 2795a,b can be positioned at approximately a 90 degree angle relative to the slot 2733. As shown at FIG. 27G, each arm 2795a,b can be slid through the slot 2733 until the beginning of the bump 2778 on the arm 2795a,b is flush with the inside of the slot 2733 (to do so, the inflow edges 2793 can be folded inward towards one another and the central axis. At FIG. 27H, the arms 2795a,b can be at approximately 90 degrees relative to the slot 2733 after being pulled therethrough. At FIG. 27I, the two leaflets 2722a,b can be separated, and, at FIGS. 27J and 27K, the process can be repeated for each of the other slots and attachment points (e.g., two additional slots/leaflet attachment points). As shown at FIGS. 27L and 27M, the leaflet arms 2795a,b can be folded away from one another, and the leaflet protectors 2773a,b can be folded away from one another. As shown at FIG. 27N, the edges of each arm 2795a,b can be placed horizontal to the outflow plane and the side/vertical edges can be parallel with the strut members 2721. At FIG. 27O, the plate 2727 can be placed onto the leaflet arms and aligned with the slot 2733. The vertical edges 2761 of the retaining plate 2727 can be aligned parallel with the vertical strut members 2721. The top 2762 of the retaining plate 2727 can be aligned with the outflow tips 2777 of the strut frame 2705. The center of the retaining plate 2727 can be aligned with the center of the slot 2733. At FIG. 27P, the first suture 2772a can be wound around the top set of indents 2773a,b in the plate 2727 and the third suture 2772c can be wound around the bottom set of indents 2773i,j. At FIG. 27Q, the second suture 2772b can be woven around the plate 2727 into the remaining indents 2773c-h in a crisscross pattern (dotted lines represent suture on the backside of the plate 2727). The process can be repeated at each of the commissure attachment points. The sutures can advantageously help prevent translation of the plate 2727 relative to the slot 2733 and frame 2705. Further, the plate 2727 and slot 2733 can advantageously securely attach the leaflets 2722 to the frame 2705 without damaging the frame 2705, leaflets 2722a,b, and/or skirt 2716.

Figure 22:
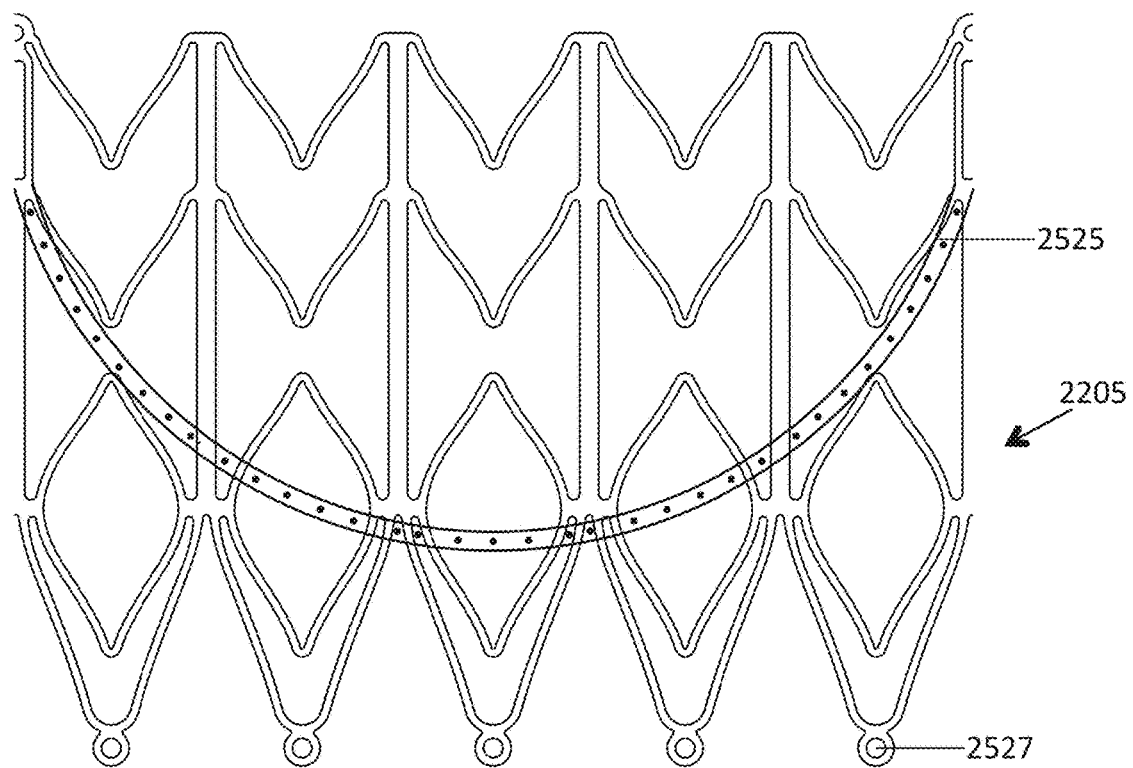
FIG. 22 shows the inflow edges of the leaflets sewn to the strut frame

In some embodiments, referring to FIG. 22, once the arms of the leaflets 2222 are attached to the strut frame 2205, the inflow edges can be sewn to the strut frame 2205. An exemplary sewing line 2525 (close to the rivets 2527 at the atrial end of the strut frame 2205) is shown in FIG. 22.

In some embodiments, a valve prosthesis as described herein can include a delivery system attachment mechanism. For example, as shown in FIGS. 2A-2B, the atrial tips 212 can each have a pin 215 extending therefrom (e.g., in the ventricular direction) around which tethers from a delivery system can be wound.

Figure 29A:
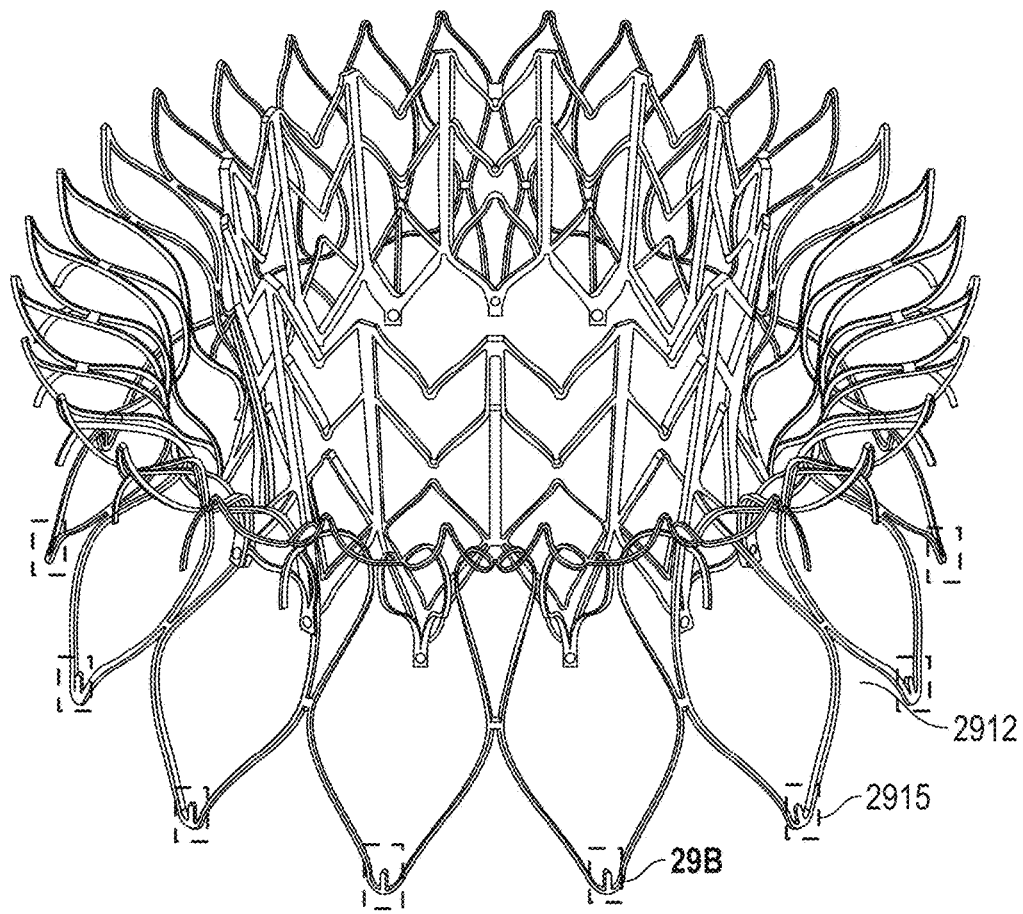
FIGS. 29A-29E show a mitral valve prosthesis with a delivery system attachment mechanism.
Figure 29B:
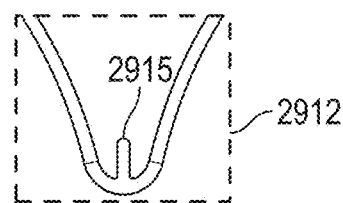
Figure 29C:
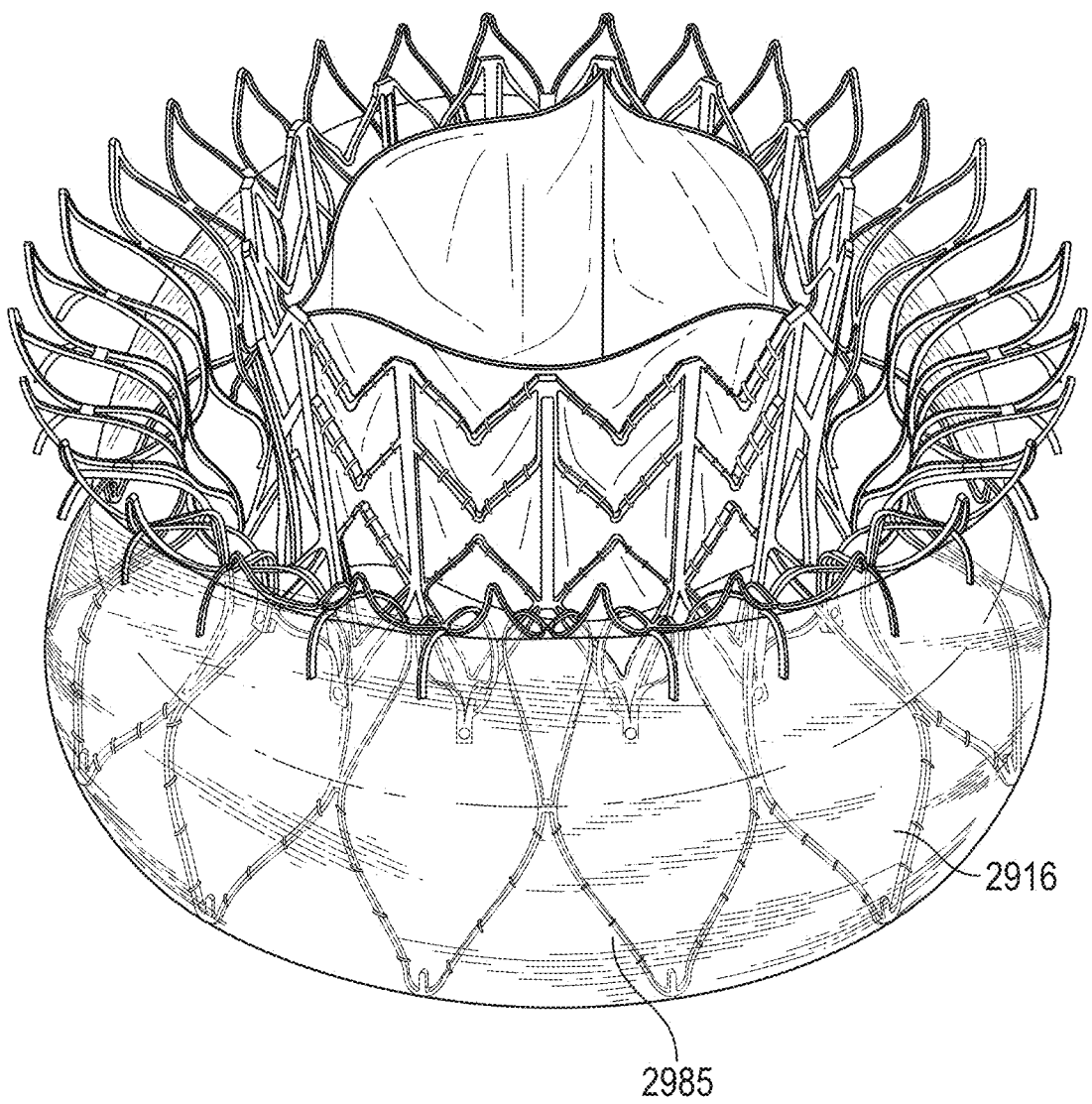
Figure 29D:
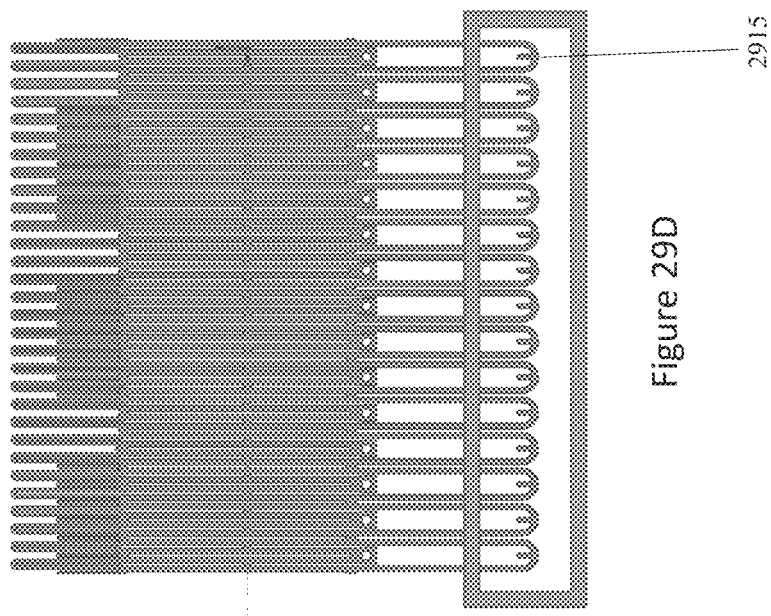
Figure 29E:
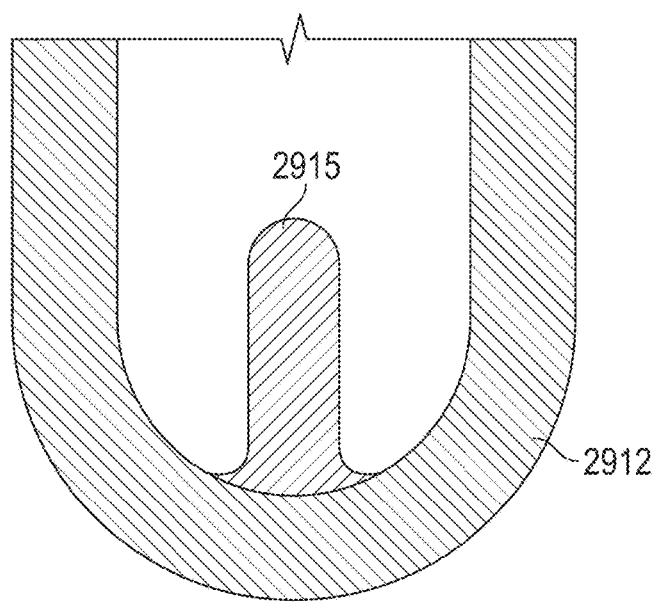

Another delivery system attachment mechanism is shown in FIGS. 29A-29E. The atrial tips 2912 each have a pin 2915 extending therefrom (e.g., in the ventricular direction). Each pin can be, for example, 0.030 inches long and approximately 0.012 inches thick. Further, as shown in FIG. 29E, the skirt 2916 can have slots 2985 therein that are aligned with the pins 2915. The slots 2985 can allow for the passage of the tethers therethrough (i.e., to provide access to the pins 2195).

An exemplary method of delivering a valve prosthesis 1700 (which can be any of the valves prostheses described herein) after attachment to the tethers of the delivery system is shown in FIGS. 17A-17J. At FIGS. 17A and 17B, the valve is packed inside of a sheath such that the tips of the ventricular anchor 1704 point towards the ventricular end (i.e., away from the central portion 1703) and the tips of the atrial anchor 1702 point towards the atrial end (i.e., away from the central portion 1703). The valve 1700 can be delivered, e.g., transseptally, to the native annulus in this packed positioned. At FIGS. 17C-E, the ventricular anchor 1704 is partially deployed, i.e., to allow the ventricular anchor 1704 to begin to flare outwards. In this embodiments, barbs on the device point radially outwards rather than towards the atrium during the initial deployment steps. At FIGS. 17F and G, the valve is pulled 1-3 cm towards the atrium to seat the ventricular anchor 1704 on the ventricular side of the annulus. At FIG. 17H, the ventricular anchor 1704 is fully deployed, allowing the barbs to extend into the tissue. At this point, the strut frame 1705 (holding leaflets) is also fully exposed. At FIG. 17I, the atrial anchor 1702 is partially released to allow the anchor 1702 to drop against the wall of the atrium. At FIG. 17J, the atrial anchor 1702 is fully released, and the valve 1700 is seated in place.

The valve prostheses described herein can advantageously pack to a very low packing length, such as less than 4 cm, less than 3.8 cm, less than 3.6 cm, less than 3.2 cm, or less than 3.0 cm for delivery with a 32 French catheter. This low axial packing length advantageously allows the prostheses to be delivered transseptally, e.g., be easily maneuvered around the bend through the septum.

Figure 13A:
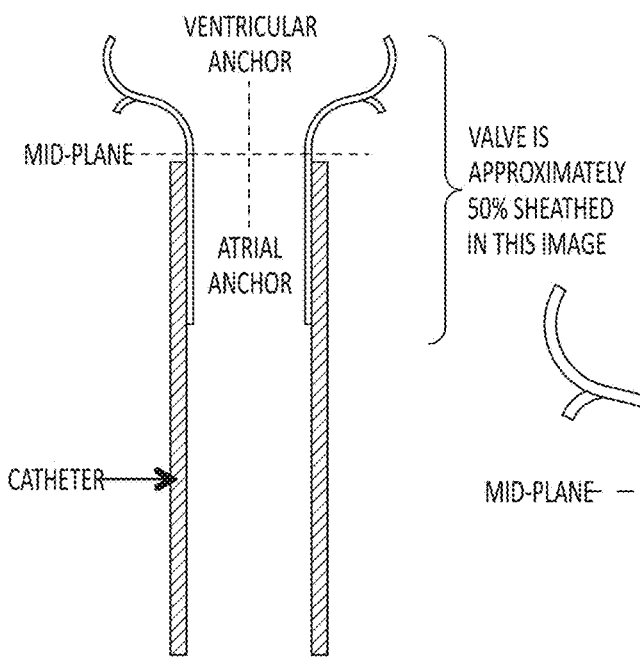
FIGS. 13A-13B show deployment of a ventricular anchor of an exemplary mitral valve prosthesis out of a sheath.
Figure 13B:
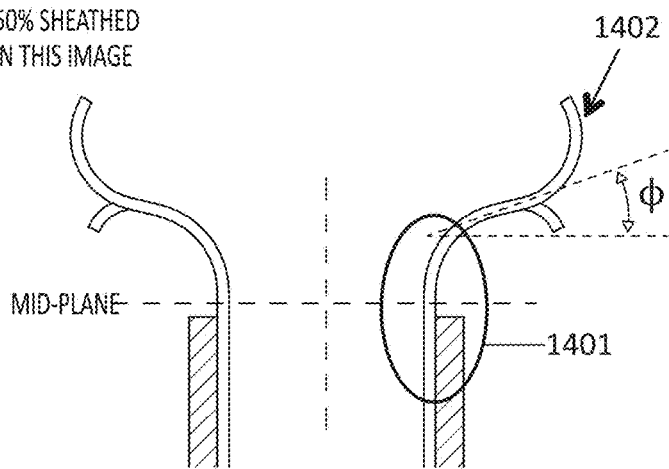

Further, the cells and/or v-shaped patterns of the valve prostheses described herein can be specifically designed so as to ensure that the ventricular side doesn't flare out when delivered. For example, by making the atrial anchor flexible (e.g., with flexible members), the ventricular anchor is less likely to hook around when delivered. As another example, the radius of the valve (the anchor or the strut frame) can be tuned and/or the valve can be made more flexible in specific areas (of the anchor or the strut frame) so as to ensure that the valve is less prone to hooking/flaring out when delivered. That is, referring to FIGS. 13A and 13B, in one embodiment, a change in the radius of curvature in region 1401 will yield a change in the deployment angle ø of the ventricular anchor in region 1402. Decreasing the curvature in region 1401 will make the frame less prone to wrapping around the catheter tip when the ventricular anchor is exposed from the catheter. In another embodiment, by making region 1401 flexible, but leaving the remaining portions of the ventricular and atrial anchors relatively stiff, the deployment angle ø in region 1402 is less prone to wrapping around the catheter tip when the ventricular anchor is exposed from the catheter tip.

The valve prostheses described herein can advantageously avoid interference with blood flow through the valve. For example, the skirting and shape of the nitinol on the inflow (or atrial) portion of the valve can be contoured to provide smooth approach to the valve orifice. This helps decrease the risk of any turbulent flow or pockets of stagnant blood. As another example, the attachment point between the inner strut and the outer frame can be adjusted longitudinally to change the relative obstruction of the inner strut with blood flow and the ventricular sub-valvular apparatus. As yet another example, the skirting can be selectively applied to areas only in which there is a risk of blood escaping between the prosthesis and the anatomy. By allowing some cells to be open, particularly on the ventricular anchoring member, there is less impedance to flow.

Any of the valve features or structural details of any device embodiment described herein can be incorporated or combined with any of the other embodiments herein. For example, the central members described herein are not limited in use with the anchor assemblies and strut frames in the specific embodiment, but can be replaced with any of the features described in any other embodiment.

In use, when the devices described herein can be used as mitral valve replacements. In some embodiments, when the replacement heart valve has been delivered near the mitral valve, the ventricular anchor can be deployed first in a cardiac chamber, such as the ventricle, and retracted to a seated position against the valve orifice, such as the mitral valve orifice. Then the center portion and atrial anchor portion may be deployed in another cardiac chamber, such as the atrium, wherein the expansion and reconfiguration of the atrial anchor and the central portion sandwiches the valve orifice securely between the anchors that have been deployed on either side of the annulus. Other exemplary aspects of the methods of delivery described in U.S. Pat. No. 8,870,948, issued Oct. 28, 2014, in International Patent Application No. PCT/US2016/032546, filed May 13, 2016, titled "CARDIAC VALVE DELIVERY DEVICES AND SYSTEMS," and in U.S. Provisional Patent Application Nos. 62/424,021 and 62/424,051, both filed Nov. 18, 2016 and titled "CARDIAC VALVE DELIVERY DEVICES AND SYSTEMS" all of which are incorporated by reference in their entireties.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A prosthetic mitral valve comprising:
   an anchor assembly comprising a ventricular anchor, an atrial anchor, and a central portion therebetween, wherein the ventricular anchor and the atrial anchor are configured to flare radially outwards relative to the central portion;
   an annular strut frame disposed radially within the anchor assembly, the annular strut frame attached to the anchor assembly at a plurality of attachment locations that are positioned between the central portion and an atrial-most edge of the anchor assembly; and
   a plurality of replacement leaflets secured to the annular strut frame;
   wherein the central portion is configured to align with a native valve orifice and the ventricular anchor and the atrial anchor are configured to compress native cardiac tissue therebetween.

2. The prosthetic mitral valve of claim 1, wherein an atrial end of the strut frame is attached to the anchor assembly.

3. The prosthetic mitral valve of claim 1, wherein atrial tips of the strut frame are attached to the anchor assembly.

4. The prosthetic mitral valve of claim 1, wherein an atrial end of the strut frame is flared radially outwards, the flared atrial end being radially inward of the atrial anchor.

5. The prosthetic mitral valve of claim 4, wherein a flare of the strut frame is configured to substantially conform to a flare of the atrial anchor.

6. The prosthetic mitral valve of claim 1, wherein a ventricular end of the strut frame is spaced away from the anchor assembly.

7. The prosthetic mitral valve of claim 6, wherein the ventricular end of the strut frame is spaced away from the anchor assembly by a radial distance of 1-15 mm.

8. The prosthetic mitral valve of claim 1, wherein the anchor assembly and the strut frame are configured to self-expand from a constrained configuration to an expanded configuration.

9. The prosthetic mitral valve of claim 1, wherein the strut frame is attached to the anchor assembly with a plurality of rivets.

10. The prosthetic mitral valve of claim 9, wherein each of the plurality of attachment locations is radially aligned with tips of the atrial anchor.

11. The prosthetic mitral valve of claim 1, wherein the plurality of attachment locations are each part of the anchor assembly that extends further radially inwards than a remaining portion of the anchor assembly.

12. The prosthetic mitral valve of claim 1, wherein the anchor assembly comprises a plurality of diamond-shaped cells.

13. The prosthetic mitral valve of claim 12, wherein the plurality of attachment locations are positioned at a midpoint of the outermost atrial diamond-shaped cells.

14. The prosthetic mitral valve of claim 1, wherein the strut frame includes a plurality of linear struts and v-shaped connectors therebetween.

15. The prosthetic mitral valve of claim 1, wherein the anchor assembly forms a substantially hour-glass shape.

16. A prosthetic mitral valve comprising:
    an anchor assembly comprising a ventricular anchor, an atrial anchor, and a central portion therebetween, wherein the ventricular anchor and the atrial anchor are configured to flare radially outwards relative to the central portion, further wherein the anchor assembly comprises a plurality of diamond-shaped cells;
    an annular strut frame disposed radially within the anchor assembly, the annular strut frame attached to the anchor assembly at a plurality of attachment locations that are positioned at a mid-point of the outermost atrial diamond-shaped cells between the central portion and an atrial-most edge of the anchor assembly; and
    a plurality of replacement leaflets secured to the annular strut frame.

17. The prosthetic mitral valve of claim 16, wherein an atrial end of the strut frame is attached to the anchor assembly.

18. The prosthetic mitral valve of claim 16, wherein atrial tips of the strut frame are attached to the anchor assembly.

19. The prosthetic mitral valve of claim 16, wherein an atrial end of the strut frame is flared radially outwards, the flared atrial end being radially inward of the atrial anchor.

20. The prosthetic mitral valve of claim 19, wherein a flare of the strut frame is configured to substantially conform to a flare of the atrial anchor.

21. The prosthetic mitral valve of claim 16, wherein a ventricular end of the strut frame is spaced away from the anchor assembly.

22. The prosthetic mitral valve of claim 21, wherein the ventricular end of the strut frame is spaced away from the anchor assembly by a radial distance of 1-15 mm.

23. The prosthetic mitral valve of claim 16, wherein the anchor assembly and the strut frame are configured to self-expand from a constrained configuration to an expanded configuration.

24. The prosthetic mitral valve of claim 16, wherein the strut frame is attached to the anchor assembly with a plurality of rivets.

25. The prosthetic mitral valve of claim 16, wherein each of the plurality of attachment locations is radially aligned with tips of the atrial anchor.

26. The prosthetic mitral valve of claim 16, wherein the plurality of attachment locations are each part of the anchor assembly that extends further radially inwards than a remaining portion of the anchor assembly.

27. The prosthetic mitral valve of claim 16, wherein the strut frame includes a plurality of linear struts and v-shaped connectors therebetween.

28. The prosthetic mitral valve of claim 16, wherein the anchor assembly forms a substantially hour-glass shape.

* * * * *